US010889610B2

(12) United States Patent
Zetterberg et al.

(10) Patent No.: US 10,889,610 B2
(45) Date of Patent: *Jan. 12, 2021

(54) ALPHA-D-GALACTOSIDE INHIBITORS OF GALECTINS

(71) Applicant: GALECTO BIOTECH AB, Copenhagen (DK)

(72) Inventors: Fredrik Zetterberg, Askim (SE); Ulf Nilsson, Lund (SE); Hakon Leffler, Lund (SE)

(73) Assignee: GALECTO BIOTECH AB, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/313,628

(22) PCT Filed: Jul. 9, 2017

(86) PCT No.: PCT/EP2017/067181
§ 371 (c)(1),
(2) Date: Dec. 27, 2018

(87) PCT Pub. No.: WO2018/011094
PCT Pub. Date: Jan. 18, 2018

(65) Prior Publication Data
US 2019/0315793 A1 Oct. 17, 2019

(30) Foreign Application Priority Data
Jul. 12, 2016 (EP) ..................................... 16179070

(51) Int. Cl.
C07H 19/056 (2006.01)
A61K 31/7056 (2006.01)
C07H 19/12 (2006.01)

(52) U.S. Cl.
CPC ....... C07H 19/056 (2013.01); A61K 31/7056 (2013.01); C07H 19/12 (2013.01)

(58) Field of Classification Search
None
See application file for complete search history.

(56) References Cited

U.S. PATENT DOCUMENTS

| 7,700,763 | B2 * | 4/2010 | Leffler | C07H 19/056 536/123.13 |
| 8,703,720 | B2 * | 4/2014 | Leffler | C07H 15/22 514/23 |
| 9,243,021 | B2 * | 1/2016 | Sethi | A61M 15/00 |
| 9,580,456 | B2 * | 2/2017 | Nilsson | A61M 15/00 |
| 9,699,713 | B2 * | 7/2017 | Zhou | H04L 47/26 |
| 10,253,059 | B2 * | 4/2019 | Leffler | C07H 19/056 |
| 10,464,964 | B2 * | 11/2019 | Zetterberg | C07H 3/04 |
| 2015/0320782 | A1 * | 11/2015 | Panjwani | A61K 38/17 206/364 |
| 2017/0349619 | A1 * | 12/2017 | Brimert | C07H 15/207 |
| 2018/0221400 | A1 * | 8/2018 | Gelovani | A61K 31/7016 |
| 2018/0327440 | A1 * | 11/2018 | Zetterberg | A61P 27/02 |
| 2019/0225638 | A1 * | 7/2019 | Zetterberg | C07H 17/02 |
| 2019/0359643 | A1 * | 11/2019 | Brimert | C07H 15/26 |

FOREIGN PATENT DOCUMENTS

| WO | 2005/113569 A1 | 12/2005 |
| WO | 2010/126435 A1 | 11/2010 |
| WO | 2016/120403 A1 | 8/2016 |

OTHER PUBLICATIONS

U.S. Appl. No. 16/200,464, filed Nov. 2018, Leffler et al.*
Brewer, "Thermodynamic binding studies of galectin-1,-3 and -7", in Glycoconjugate Journal 19, 2004, p. 459-465; 7 pages.
Scott et al., "Galectin-1: A bifunctional regulator of cellular proliferation", in Glycoconjugate Journal 19, 2004, p. 467-477; 11 pages.
Horie et al., "Galectin-1 plays essential roles in adult mammalian nervous tissues. Roles of oxidized galectin-1", in Glycoconjugate Journal 19, 2004, p. 479-489; 11 pages.
Lipkowitz et al., "Galectin 9 is the sugar-regulated urate transporter/channel UAT", in Glycoconjugate Journal 19, 2004, p. 491-498; 8 pages.
Patterson et al., "Understanding the biochemical activities of galectin-1 and galectin-3 in the nucleus", in Glycoconjugate Journal 19, 2004, p. 499-506; 8 pages.
Hsu et al., "Regulation of cellular homeostasis by galectins", in Glycoconjugate Journal 19, 2004, p. 507-515; 9 pages.
Zick et al., "Role of galectin-8 as a modulator of cell adhesion and cell growth", in Glycoconjugate Journal 19, 2004, p. 517-526; 10 pages.
Ochieng et al., "Extracellular functions of galectin-3", in Glycoconjugate Journal 19, 2004, p. 527-535; 9 pages.
Brûle et al., "Expression of galectins in cancer: A critical review", in Glycoconjugate Journal 19, 2004, p. 537-542; 6 pages.
Takenaka et al., "Galectin-3 and metastasis", in Glycoconjugate Journal 19, 2004, p. 543-549; 7 pages.
Grassadonia et al., "90K (Mac-2 BP) and galectins in tumor progression and metastasis", in Glycoconjugate Journal 19, 2004, p. 551-556, 6 pages.
Bidon-Wagner et al., "Human galectin-8 isoforms and cancer", in Glycoconjugate Journal 19, 2004, p. 557-563; 7 pages.
Rabinovich et al., "Shedding light on the immunomodulatory properties of galectins: Novel regulators of innate and adaptive immune responses", in Glycoconjugate Journal 19, 2004, p. 565-573; 9 pages.
Almkvist et al., "Galectins as inflammatory mediators", in Glycoconjugate Journal 19, 2004, p. 575-581; 7 pages.

(Continued)

Primary Examiner — Eric Olson
(74) Attorney, Agent, or Firm — Maier & Maier, PLLC

(57) ABSTRACT

The present invention relates to a compound of the general formula (1). The compound of formula (1) is suitable for use in a method for treating a disorder relating to the binding of a galectin, such as galectin-3 to a ligand in a mammal, such as a human. Furthermore, the present invention concerns a method for treatment of a disorder relating to the binding of a galectin, such as galectin-3 to a ligand in a mammal, such as a human.

20 Claims, No Drawings

(56) References Cited

OTHER PUBLICATIONS

Sato et al., "Seeing strangers or announcing "danger": Galectin-3 in two models of innate immunity", in Glycoconjugate Journal 19, 2004, p. 583-591; 9 pages.
Hirashima et al., "Galectin-9 in physiological and pathological conditions", in Glycoconjugate Journal 19, 2004, p. 593-600; 8 pages.
Young et al., "Galectins in parasite infection and allergic inflammation", in Glycoconjugate Journal 19, 2004, p. 601-606; 6 pages.
Pace et al., "Insect galectins: Roles in immunity and development", in Glycoconjugate Journal 19, 2004, p. 607-614; 8 pages.
Watt et al., "The involvement of galectin-1 in skeletal muscle determination, differentiation and regeneration", in Glycoconjugate Journal 19, 2004, p. 615-619; 5 pages.
Hughes, "Galectins in kidney development", in Glycoconjugate Journal 19, 2004, p. 621-629; 9 pages.
International Search Report and Written Opinion of the International Searching Authority dated Aug. 21, 2017 in corresponding International application No. PCT/EP2017/067181; 12 pages.
Giguère et al., "Inhibitory potential of chemical substitutions at bioinspired sites of β-d-galactopyranose on neoglycoprotein/cell surface binding of two classes of medically relevant lectins", Bioorganic & Medicinal Chemistry, Mar. 9, 2011, vol. 19, No. 10, p. 3280-3287; 8 pages.
Rajput et al., "Synthesis and evaluation of iminocoumaryl and coumaryl derivatized glycosides as galectin antagonists", Bioorganic & Medicinal Chemistry Letters, Jun. 9, 2014, vol. 24, No. 15, p. 3516-3520; 5 pages.
Almkvist et al., "Lipopolysaccharide-Induced Gelatinase Granule Mobilization Primes Neutrophils for Activation by Galectin-3 and Formylmethionyl-Leu-Phe", in Infection and Immunity, vol. 69, No. 2, Feb. 2001, p. 832-837; 6 pages.
Barondes et al., "Galectins", in The Journal of Biological Chemistry, vol. 269, No. 33, Aug. 19, 1994, p. 20807-20810; 4 pages.
Blois et al., "A pivotal role for galectin-1 in fetomaternal tolerance", in Nature Medicine, vol. 13, No. 12, Dec. 2007, p. 1450-1457; 9 pages.
Chen et al., "Targeting Galectin-1 and Galectin-3 Attenuates VEGF-A-induced Angiogenesis", in Molecular Biology Cell (suppl), Abstract, No. 2695, 2012; 1 page.
Cumpstey et al., "Synthesis of a phenyl thio-β-D-galactopyranoside library from 1,5-difluoro-2,4-dinitrobenzene: discovery of efficient and selective monosaccharide inhibitors of galectin-7", in Org. Biomol. Chem., vol. 3, 2005, p. 1922-1932; 11 pages.
Cumpstey et al., "C2-Symmetrical thiodigalactoside bis-benzamido derivatives as high-affinity inhibitors of galectin-3: Efficient lectin inhibition through double arginine-arene interactions", in Angew. Chem. Int., Ed. 44, 2005, p. 5110-5112; 3 pages.
Cumpstey et al., "Double Affinity Amplification of Galectin-Ligand Interactions through Arginine-Arene Interactions: Synthetic, Thermodynamic, and Computational Studies with Aromatic Diamido Thiodigalactosides", in Chem. Eur. J., vol. 14, 2008, p. 4233-4245; 13 pages.
Dam et al., "Effects of Clustered Epitopes in Multivalent Ligand-Receptor Interactions", in Biochemistry, vol. 47, 2008, p. 8470-8476; 7 pages.
Delacour et al., "Apical Sorting by Galectin-3-Dependent Glycoprotein Clustering", in Traffic, vol. 8, 2007, p. 379-388; 10 pages.
Delaine et al., "Galectin-Inhibitory Thiodigalactoside Ester Derivatives Have Antimigratory Effects in Cultured Lung and Prostate Cancer Cells", in J. Med. Chem., vol. 51, 2008, p. 8109-8114; 6 pages.
Demotte et al., "A Galectin-3 Ligand Corrects the Impaired Function of Human CD4 and CD8 Tumor-Infiltrating Lymphocytes and Favors Tumor Rejection in Mice", in Cancer Research, vol. 70, 2010, p. 7476-7488; 14 pages.
Farkas et al., "Synthesis of 1,2-trans-glycopyranosyl chlorides using the dichloromethyl methyl ether-boron trfliuoride etherate reagent", in Carbohydrate Research, vol. 48, 1976, p. 136-138; 3 pages.

Garner et al., "Galectin-glycan lattices regulate cell-surface glycoprotein organization and signalling", in Biochemical Society Transactions, vol. 36, Part 6, 2008, p. 1472-1477; 6 pages.
Giguère et al., "Carbohydrate triazoles and isoxazoles as inhibitors of galectine-1 and -3", in Chem. Commun., 2006, p. 2379-2381; 3 pages.
Glinsky et al., "Inhibition of Human Breast Cancer Metastasis in Nude Mice by Synthetic Glycoamines", in Cancer Research, vol. 56, Dec. 1, 1996, p. 5319-5324; 6 pages.
Glinsky et al., "Synthetic Galectin-3 Inhibitor Increases Metastatic Cancer Cell Sensitivity to Taxol-Induced Apoptosis In Vitro and In Vivo", in Neoplasia, vol. 11, No_ 9, Sep. 2009, p. 901-909; 9 pages.
Huflejt et al., "Galectin-4 in normal tissues and cancer", in Glycoconjugate Journal 20, 2004, p. 247-255; 9 pages.
Ingrassia et al., "A Lactosylated Steroid Contributes in Vivo Therapeutic Benefits in Experimental Models of Mouse Lymphoma and Human Glioblastoma", in J. Med. Chem., vol. 49, 2006, p. 1800-1807; 8 pages.
John et al., "Truncated Galectin-3 Inhibits Tumor Growth and Metastasis in Orthotopic Nude Mouse Model of Human Breast Cancer", in Clinical Cancer Research, vol. 9, Jun. 2003, p. 2374-2383; 10 pages.
Kouo et al., "Galectin-3 Shapes Antitumor Immune Responses by Suppressing CD8 T Cells via LAG-3 and Inhibiting Expansion of Plasmacytoid Dendritic Cells", in Cancer Immunology Research, vol. 3, No. 4, Apr. 2015, p. 412-423; 13 pages.
Lau et al., "N-Glycans in cancer progression", in Glycobiology, vol. 18, No. 10, 2008, p. 750-760; 11 pages.
Lau et al., "Complex N-Glycan Number and Degree of Branching Cooperate to Regulate Cell Proliferation and Differentiation", in Cell 129, Apr. 6, 2007, p. 123-134; 12 pages.
Leffler et al., "Specificity of Binding of Three Soluble Rat Lung Lectins to Substituted and Unsubstituted Mammalian 3-Galactosides", in The Journal of Biological Chemistry, vol. 261, No. 22, Aug. 5, 1986, p. 10119-10126; 8 pages.
Leffler, "Galectins Structure and Function—A Synopsis", in Results and Problems in Cell Differentiation, vol. 33, 2001, p. 57-83; 27 pages.
Leffler et al., "Introduction to galectins", in Glycoconjugate Journal 19, 2004, p. 433-440; 8 pages.
Chiariotti et al., "Galectin genes: Regulation of expression", in Glycoconjugate Journal 19, 2004, p. 441-449; 9 pages.
Lin et al., "Galectin-3 Targeted Therapy with a Small Molecule Inhibitor Activates Apoptosis and Enhances Both Chemosensitivity and Radiosensitivity in Papillary Thyroid Cancer", in Mol. Cancer Res., vol. 7, No. 10, Oct. 2009, p. 1655-1662; 8 pages.
Mackinnon et al., "Regulation of Alternative Macrophage Activation by Galectin-3", in The Journal of Immunology, vol. 180, 2008, p. 2650-2658; 9 pages.
Mackinnon et al., "Regulation of Transforming Growth Factor-β1-driven Lung Fibrosis by Galectin-3", in Am. J. Resp. Crit. Care Med., vol. 185, 2012, p. 1-11; 11 pages.
Massa et al., "L-29, an Endogenous Lectin, Binds to Glycoconjugate Ligands with Positive Cooperativity", in Biochemistry, vol. 32, 1993, p. 260-267; 8 pages.
Melero et al., "Evolving synergistic combinations of targeted immunotherapies to combat cancer", in Nature Reviews, vol. 15, Aug. 2015, p. 457-472; 16 pages.
Partridge et al., "Regulation of Cytokine Receptors by Golgi N-Glycan Processing and Endocytosis", in Science, vol. 306, Oct. 1, 2004, p. 120-124; 6 pages.
Perone et al., "Suppression of Autoimmune Diabetes by Soluble Galectin-1", in The Journal of Immunology, vol. 182, Sep. 15, 2017, p. 2641-2653; 14 pages.
Pienta et al., "Inhibition of Spontaneous Metastasis in a Rat Prostate Cancer Model by Oral Administration of Modified Citrus Pectin", in J. Natl. Cancer Inst., vol. 87, No. 5, Mar. 1, 1995, p. 348-353; 6 pages.
Ramos-Soriano et al., "Synthesis, Biological Evaluation, WAC and NMR Studies of S-Galactosides and Non-Carbohydrate Ligands of Cholera Toxin Based on Polyhydroxyalkylfuroate Moieties", in Chem. Eur. J., vol. 19, 2013, p. 17989-18003; 15 pages.

(56) References Cited

OTHER PUBLICATIONS

Ruvolo, "Galectin 3 as a guardian of the tumor microenvironment", in Biochimica et Biophysica Acta, Apr. 8 2015; http://dx.doi.org/10.1016/j.bbamcr.2015.08.008; 11 pages.

Saegusa et al., "Galectin-3 is critical for the development of the allergic inflammatory response in a mouse model of atopic dermatitis", in Am J Pathol, vol. 174, No. 3, Mar. 2009, p. 922-931; 10 pages.

Salameh et al., "3-(1,2,3-Triazol-1-yl)-1-thio-galactosides as small, efficient, and hydrolytically stable inhibitors of galectin-3", in Bioorg. Med. Chem. Lett., vol. 15, 2005, p. 3344-3346; 3 pages.

Salameh et al., "1H-1,2,3-Triazol-1-yl thiodigalactoside derivatives as high affinity galectin-3 inhibitors", in Bioorg Med Chem, vol. 18, 2010, p. 5367-5378; 13 pages.

Salomonsson et al., "Monovalent interactions of galectin-1", in Biochemistry, vol. 49, 2010, p. 9518-9532; 15 pages.

Sörme et al., "Low micromolar inhibitors of galectin-3 based on 3'-derivatization of N-acetyllactosamine", in ChemBioChem, vol. 3, 2002, p. 183-189; 7 pages.

Sörme et al., "Fluorescence polarization to study galectin-ligand interactions", in Meth. Enzymol., vol. 362, 2003, p. 504-512; 9 pages.

Sörme et al., "Design and synthesis of galectin inhibitors", in Meth. Enzymol., vol. 363, 2003b, p. 157-169; 13 pages.

Sörme et al., "Fluorescence polarization as an analytical tool to evaluate galectin-ligand interactions", in Anal. Biochem., vol. 334, 2004, p. 36-47; 12 pages.

Thijssen et al., "Galectins in the tumor endothelium: opportunities for combined cancer therapy", in Blood, vol. 110, 2007, p. 2819-2827; 10 pages.

Toscano et al., "Differential glycosylation of TH1, TH2 and TH-17 effector cells selectively regulates susceptibility to cell death", in Nat Immunol, vol. 8, No. 8, Aug. 2007, p. 825-834; 10 pages.

Ogawa et al., "The speciation of conger eel galectins by rapid adaptive evolution", in Glycoconjugate Journal 19, 2004, p. 451-458; 8 pages.

\* cited by examiner

ALPHA-D-GALACTOSIDE INHIBITORS OF GALECTINS

TECHNICAL FIELD

The present invention relates to novel compounds, the use of said compounds as medicament and for the manufacture of a medicament for the treatment of inflammation; fibrosis; scarring; keloid formation; aberrant scar formation; surgical adhesions; septic shock; cancers; autoimmune diseases; metabolic disorders; heart disease; heart failure; pathological angiogenesis; eye diseases; atherosclerosis; metabolic diseases; asthma and other interstitial lung diseases; and liver disorders in mammals. The invention also relates to pharmaceutical compositions comprising said novel compounds.

BACKGROUND ART

Galectins are proteins with a characteristic carbohydrate recognition domain (CRD) (Leffler et al., 2004). This is a tightly folded β-sandwich of about 130 amino acids (about 15 kDa) with the two defining features 1) a β-galactose binding site and 2) sufficient similarity in a sequence motif of about seven amino acids, most of which (about six residues) make up the β-galactose binding site. However, sites adjacent to the β-galactose site are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004).

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Lepur et al., 2012). These were the first discovered galectins and are abundant in many tissues.

There are now over 5700 publications on galectins in PubMed, with most, as mentioned above, about galectins-1 (>1400) and -3 (>2800). Strong evidence suggests roles for galectins in e.g. inflammation and cancer, and development (Blidner et al., 2015, Ebrahim et al., 2014).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004; Arthur et al., 2015). They can also function in all these compartments; for galectin-3, solid evidence published in well respected journals support roles in RNA splicing in the nucleus, inhibition of apoptosis in the cytosol, accumulation around disrupted vesicles, association with microtubule organizing center of cilia, and a variety of extracellular effects on cell signaling and adhesion (Elola et al. 2015, Funasaka et al., 2014, Aits et al., 2015, Clare et al., 2014). Other galectins also may act in the cytosol by enhancing apoptosis and regulating the cell cycle and differentiation in certain cells. Most galectins act also extracellularly by cross-linking glycoproteins (e.g. laminin, integrins, and IgE receptors) possibly forming supramolecular ordered arrays (Elola et al., 2015) and may thereby modulate cell adhesion and induce intracellular signals. Related to this, recent years have seen the emergence of a molecular mechanism of these galectin functions involving a formation of microdomains (lattices) within membranes, (Elola et al., 2015) which in turn affects intracellular trafficking and cell surface presentation of glycoprotein receptors. This has been documented in cell culture, in null mutant mice, and animals treated with galectin or galectin inhibitors.

Potential therapeutic use of galectin-3 inhibitors Galectin-3 has been implicated in diverse phenomena and, hence, inhibitors may have multiple uses (Blanchard et al., 2014). It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation

A pro-inflammatory role of galectin-3 is indicated by its induction in cells at inflammatory sites, a variety of effects on immune cells (e.g. oxidative burst in neutrophils and chemotaxis in monocytes), and decrease of the inflammatory response, mainly in neutrophils and macrophages, in null mutant mice (Blidner et al., 2015, Arthur et al., 2015). Importantly, recent studies have identified galectin-3 as a key rate-limiting factor in macrophage M2 differentiation and myofibroblast activation, which influences the development of fibrosis (Mackinnon et al., 2008; Mackinnon et al., 2012, Li et al., 2014).

Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of certain receptors (Elola et al., 2015), such as the TGF-ß receptor (MacKinnon, 2012), which in turn regulates alternative macrophage differentiation into M2 macrophages and myofibroblast activation.

Hence, as galectin-3 is a good candidate for being an endogenous enhancer of TGF-ß signaling and alternative macrophage differentiation and myofibroblast activation, galectin-3 inhibitors may be very useful in treating fibrosis and adverse tissue remodeling.

Treatment of Cancer

A large number of immunohistochemical studies show changed expression of certain galectins in cancer (Thijssen et al, 2015; Ebrahim et al., 2014) and for example galectin-3 is now an established histochemical marker of thyroid cancer. The direct evidence for a role of galectin-3 in cancer comes mainly from mouse models. In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. Further, recent evidence have shown that galectin-3 plays a critical role in the tumor microenvironment (Ruvolo, 2015). Galectin-3 is also believed to regulate the interaction between the tumor cells and immune cells, such as T-lymphocytes (T-cells), and inhibition of galectin-3 has been shown to restore T-cell activity (Demotte et al. 2010, Kouo et al. 2015, Menero et al. 2015). From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Blanchard et al., 2015).

Also other galectins are frequently over-expressed in low differentiated cancer cells, or induced in specific cancer types (Thijssen et al, 2015; Ebrahim et al. 2014). Galectin-1 induces apoptosis in activated T-cells and has a remarkable immunosuppressive effect on autoimmune disease in vivo (Blidner et al., 2015). Therefore, the over-expression of these galectins in cancers might help the tumor to defend itself against the T-cell response raised by the host.

Null mutant mice for galectins-1, -3, -7 and -9 have been established and are healthy and reproduce apparently normally in animal house conditions. However, further studies have revealed subtle phenotypes under different type of challenge, mainly in function of immune cells (Blidner et al., 2015), but also other cells types (Viguier et al., 2014). The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Treatment of Angiogenesis

Vascular endothelial growth factors (VEGFs) signaling through VEGF receptor-2 (VEGFR-2) is the primary angiogenic pathway. Studies have been published demonstrating that both galectin-1 (Gal-1) and galectin-3 (Gal-3) are important modulators for VEGF/VEGFR-2 signaling pathway (Croci et al., 2014). It has also been published that a galectin inhibitor, TDX, is expected have efficacy against pathological angiogenesis. (Chen 2012)

Known Inhibitors

Natural Ligands

Solid phase binding assays and inhibition assays have identified a number of saccharides and glycoconjugates with the ability to bind galectins (reviewed by Leffler, 2001 and Leffler et al., 2004). All galectins bind lactose with a $K_d$ of 0.5-1 mM. The affinity of D-galactose is 50-100 times lower. N-Acetyllactosamine and related disaccharides bind about as well as lactose, but for certain galectins, they can bind either worse or up to 10 times better. The best small saccharide ligands for galectin-3 were those carrying blood group A-determinants attached to lactose or LacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1 (Leffler and Barondes, 1986). A modified plant pectin polysaccharide has been reported to bind galectin-3 (Pienta et al., 1995).

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. A chemically modified form of citrus pectin (Platt and Raz, 1992) that inhibits galectin-3 shows anti-tumor activity in vivo (Pienta et al., 1995; Nangia-Makker et al., 2002).

Cluster molecules having up to four lactose moieties showed a strong multivalency effect when binding to galectin-3, but not to galectin-1 and galectin-5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules.

Thiodigalactoside is known to be a synthetic and hydrolytically stable, yet polar inhibitor, approximately as efficient as N-acetyllactosamine (Leffler and Barondes, 1986). N-Acetyllactosamine derivatives carrying aromatic amides or substituted benzyl ethers at C-3' have been demonstrated to be highly efficient inhibitors of galectin-3, with unprecedented $IC_{50}$ values as low as 4.8 µM, which is a 20-fold improvement in comparison with the natural N-acetyllactosamine disaccharide (Sörme et al., 2002; Sörme et al., 2003b). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed, (Cumpstey et al., 2005b; Cumpstey et al., 2008; Salameh et al., 2010; WO/2005/113569 and US2007185041; WO/2005/113568, U.S. Pat. No. 7,638,623 B2, T. Delaine, 2016, ChemBioChem 10.1002/cbic.201600285)) which lack O-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach at 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamido- and ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

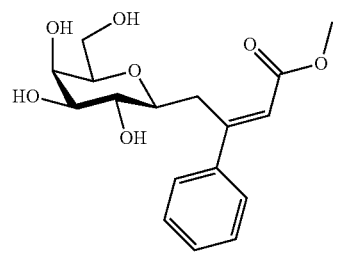

as described in WO/2005/113568, and

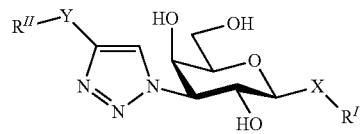

as described in WO/2005/113569, in which $R^1$ can be a D-galactose.

In recently published US20140099319, WO2014067986 and (T. Delaine, 2016, ChemBioChem 10.1002/cbic.201600285) are disclosed a compound of formula

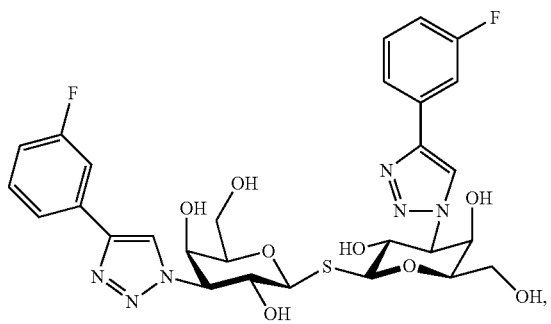

having fluorine (F) in the meta position on both the phenyl rings in relation to the triazole rings. This compound has been shown to be a promising drug candidate for lung fibrosis, and in particular is very selective on galectin-3 with high affinity.

A series of small C1 or C1 and C3-substituted galactopyranosides have been disclosed showing affinity towards galectin-3 and 1. The beta-D-galactopyranosides were reported as having affinity in the same range or less than lactose, which has a Kd of about 91 µM towards galectin-3 and 190 µM towards galectin-1. (Giguere, D et. al. 2011, 2008, 2006).

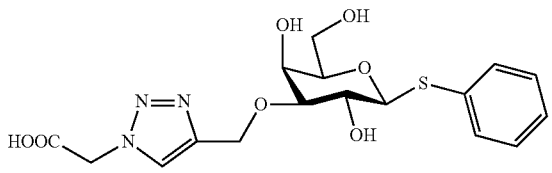

Gal-1 313 µM
Gal-3 >5000

Gal-1 1.25 mM
Gal-3 5 mM

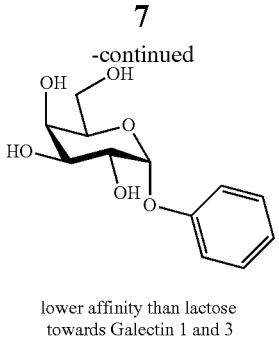

lower affinity than lactose
towards Galectin 1 and 3

There is no disclosure or mentioning of corresponding alpha-anomers having affinity towards galectin-3 or galectin-1 better than lactose.

SUMMARY OF THE INVENTION

The compounds of the present invention are novel α-D-galactopyranose compounds that unexpectedly have shown very high affinity for galectin-3, and are considered novel potent drug candidates. The compounds of the present invention also have selectivity for Galectin-1. Some of these compounds have very good PK properties for e.g. oral administration, such as low clearance and high bioavailability.

In broad aspect the present invention concerns a D-galactopyranose compound of formula (1)

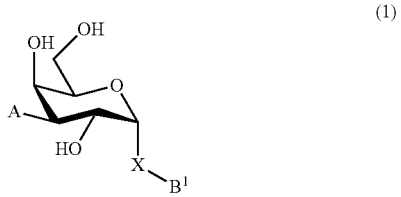

wherein
the pyranose ring is α-D-galactopyranose,
A is selected from

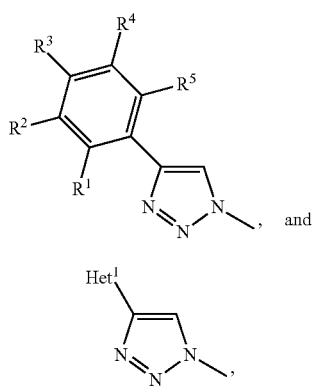

wherein Het$^1$ is selected from a pyridinyl, optionally substituted with a group selected from H, CN, Br, Cl, I, F, methyl optionally substituted with a F, OCH$_3$ optionally substituted with a F, and SCH$_3$ optionally substituted with a F; or a pyrimidyl, optionally substituted with a group selected from H, CN, Br, Cl, I, F, methyl optionally substituted with a F, OCH$_3$ optionally substituted with a F, and SCH$_3$ optionally substituted with a F;

wherein R$^1$-R$^5$ are independently selected from a group consisting of H, CN, Br, Cl, I, F, methyl optionally substituted with a F, OCH$_3$ optionally substituted with a F, and SCH$_3$ optionally substituted with a F;

X is selected from S, SO, and SO$_2$;

B$^1$ is selected from a) a C$_{1-6}$ alkyl or branched C$_{3-6}$ alkyl substituted with a five or six membered heteroaromatic ring, optionally substituted with a substituent selected from CN, a halogen, methyl optionally substituted with a F, OCH$_3$ optionally substituted with a F, OCH$_2$CH$_3$ optionally substituted with a F, OH, and R$^{14}$—CONH— wherein R$^{14}$ is selected from C$_{1-3}$ alkyl and cyclopropyl; or a C$_{1-6}$ alkyl substituted with a phenyl, optionally substituted with a substituent selected from CN, a halogen, methyl optionally substituted with a F, OCH$_3$ optionally substituted with a F, OCH$_2$CH$_3$ optionally substituted with a F, OH, and R$^{15}$—CONH— wherein R$^{15}$ is selected from C$_{1-3}$ alkyl and cyclopropyl; b) an aryl, such as phenyl or naphthyl, optionally substituted with a group selected from a halogen; CN; —COOH; —CONR$^{22}$R$^{23}$, wherein R$^{22}$ and R$^{23}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-iso-propyl, optionally substituted with a F; NR$^{28}$R$^{29}$, wherein R$^{28}$ and R$^{29}$ are independently selected from H, C$_{1-3}$ alkyl and isopropyl; OH; and R$^{16}$—CONH— wherein R$^{16}$ is selected from C$_{1-3}$ alkyl and cyclopropyl; c) a C$_{5-7}$ cycloalkyl, optionally substituted with a substituent selected from a halogen, CN, methyl optionally substituted with a F, OCH$_3$ optionally substituted with a F, OCH$_2$CH$_3$ optionally substituted with a F, OH, and R$^{17}$—CONH— wherein R$^{17}$ is selected from C$_{1-3}$ alkyl and cyclopropyl; and d) a heterocycle, such as heteroaryl or heterocycloalkyl, optionally substituted with a group selected from a halogen; CN; —COOH; —CONR$^{24}$R$^{25}$, wherein R$^{24}$ and R$^{25}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-iso-propyl, optionally substituted with a F; NR$^{30}$R$^{31}$, wherein R$^{30}$ and R$^{31}$ are independently selected from H, C$_{1-3}$ alkyl and isopropyl; OH; and R$^{18}$—CONH— wherein R$^{18}$ is selected from C$_{1-3}$ alkyl and cyclopropyl; e) a C$_{1-6}$ alkyl or branched C$_{3-6}$ alkyl; or
a pharmaceutically acceptable salt or solvate thereof.

In an embodiment A is selected from formula 2 wherein R$^1$-R$^5$ are independently selected from H, halogen, CN, methyl optionally substituted with a F, and OCH$_3$ optionally substituted with a F. In a further embodiment A is selected from formula 2 wherein R$^1$ and R$^5$ are selected from H and R$^2$-R$^4$ are selected from F, Cl, Br, CN, CH$_3$ and CF$_3$. In a still further embodiment A is selected from formula 2 wherein R$^1$ and R$^5$ are selected from H and R$^2$ and R$^4$ are selected from F and R$^3$ is selected from Br, Cl, CN, CH$_3$ and CF$_3$. In a further embodiment A is selected from formula 2 wherein R$^1$ and R$^5$ are selected from H and R$^2$ is selected from F, and R$^3$-R$^4$ are selected from Cl. In a further embodiment A is selected from formula 2 wherein R$^1$, R$^2$ and R$^5$ are selected from H and R$^3$ and R$^4$ are selected from F and Cl.

In a further embodiment A is selected from formula 3 wherein Het$^1$ is a pyridinyl optionally substituted with a group selected from Br, F, and Cl. In a still further embodiment A is selected from formula 3 wherein Het$^1$ is a pyridinyl substituted with a group selected from F and Cl.

In a further embodiment X is selected from S.

In a still further embodiment B is selected from an aryl, such as phenyl or naphthyl, optionally substituted with a group selected from a halogen; CN; methyl optionally substituted with a F; OCH$_3$ optionally substituted with a F; OCH$_2$CH$_3$ optionally substituted with a F; OH; R$^{16}$—CONH— wherein R$^{16}$ is selected from C$_{1-3}$ alkyl and cyclopropyl; —COOH; NR$^{28}$R$^{29}$, wherein R$^{28}$ and R$^{29}$ are independently selected from H, C$_{1-3}$ alkyl and isopropyl; and —CONH$_2$. In a further embodiment B is selected from a phenyl or phenyl substituted with one, two or three substituents selected from halogen. In a still further embodiment B is selected from a phenyl substituted with two substituents selected from halogen, such as Cl.

In a further embodiment B is selected from a heterocycle, such as heteroaryl or heterocycloalkyl, optionally substituted with a group selected from a halogen; CN; methyl optionally substituted with a F; OCH$_3$ optionally substituted with a F; OCH$_2$CH$_3$ optionally substituted with a F; OH; CONH$_2$; NR$^{30}$R$^{31}$, wherein R$^{30}$ and R$^{31}$ are independently selected from H, C$_{1-3}$ alkyl and isopropyl; and R$^{18}$—CONH— wherein R$^{18}$ is selected from C$_{1-3}$ alkyl and cyclopropyl. In a still further embodiment B is selected from a pyridinyl substituted with a group selected from halogen and CN, such as Cl, Br and CN.

In a further embodiment the compound of the present invention is selected from:
4-Bromo-5-cyano-2-pyridyl 3-deoxy-3-[4-(3,4,5-trifluorophenyl)-1H-1,2,3-triazol-1-yl]-1-thio-α-D-galactopyranoside;
4-Chloro-5-cyano-2-pyridyl 3-deoxy-3-[4-(3,4,5-trifluorophenyl)-1H-1,2,3-triazol-1-yl]-1-thio-α-D-galactopyranoside;
2-Chloro-4-pyridyl 3-deoxy-3-[4-(3,4,5-trifluorophenyl)-1H-1,2,3-triazol-1-yl]-1-thio-ca-D-galactopyranoside;
5-Chloro-2-cyano-3-pyridyl 3-deoxy-3-[4-(3,4,5-trifluorophenyl)-1H-1,2,3-triazol-1-yl]-1-thio-α-D-galactopyranoside;
5-Bromo-6-cyano-3-pyridyl 3-deoxy-3-[4-(3,4,5-trifluorophenyl)-1H-1,2,3-triazol-1-yl]-1-thio-α-D-galactopyranoside;
5-Bromo-2-cyano-3-pyridyl 3-deoxy-3-[4-(3,4,5-trifluorophenyl)-1H-1,2,3-triazol-1-yl]-1-thio-α-D-galactopyranoside;
4-Chloro-2-pyridyl 3-deoxy-3-[4-(3,4,5-trifluorophenyl)-1H-1,2,3-triazol-1-yl]-1-thio-α-D-galactopyranoside;
5-Bromo-3-pyridyl 3-deoxy-3-[4-(4-chloro-3,5-difluorophenyl)-1H-1,2,3-triazol-1-yl]-1-thio-α-D-galactopyranoside;
5-Chloro-3-pyridyl 3-deoxy-3-[4-(4-chloro-3,5-difluorophenyl)-1H-1,2,3-triazol-1-yl]-1-thio-α-D-galactopyranoside;
5-Chloro-6-cyano-3-pyridyl 3-deoxy-3-[4-(4-chloro-3,5-difluorophenyl)-1H-1,2,3-triazol-1-yl]-1-thio-α-D-galactopyranoside;
5-Bromo-2-cyano-3-pyridyl 3-deoxy-3-[4-(4-chloro-3,5-difluorophenyl)-1H-1,2,3-triazol-1-yl]-1-thio-α-D-galactopyranoside;
5-Bromo-6-cyano-3-pyridyl 3-deoxy-3-[4-(4-chloro-3,5-difluorophenyl)-1H-1,2,3-triazol-1-yl]-1-thio-α-D-galactopyranoside;
5-Chloro-2-cyano-3-pyridyl 3-deoxy-3-[4-(4-chloro-3,5-difluorophenyl)-1H-1,2,3-triazol-1-yl]-1-thio-α-D-galactopyranoside;
5-Chloro-3-pyridyl 3-deoxy-3-[4-(4-cyano-3,5-difluorophenyl)-1H-1,2,3-triazol-1-yl]-1-thio-α-D-galactopyranoside;
5-Chloro-3-pyridyl 3-deoxy-3-[4-(3,5-difluoro-4-trifluoromethyl-phenyl)-1H-1,2,3-triazol-1-yl]-1-thio-α-D-galactopyranoside;
5-Chloro-3-pyridyl 3-deoxy-3-[4-(3,5-difluoro-4-methylphenyl)-1H-1,2,3-triazol-1-yl]-1-thio-α-D-galactopyranoside;
5-Chloro-3-pyridyl 3-deoxy-3-[4-(4-bromo-3,5-difluorophenyl)-1H-1,2,3-triazol-1-yl]-1-thio-α-D-galactopyranoside;
5-Chloro-3-pyridyl 3-deoxy-3-[4-(3,4-dichloro-5-fluorophenyl)-1H-1,2,3-triazol-1-yl]-1-thio-α-D-galactopyranoside;
5-Chloro-3-pyridyl 3-deoxy-3-[4-(4-chloro-3-fluorophenyl)-1H-1,2,3-triazol-1-yl]-1-thio-α-D-galactopyranoside;
3,4-Dichlorophenyl 3-deoxy-3-[4-(5-fluoro-3-pyridyl)-1H-1,2,3-triazol-1-yl]-1-thio-α-D-galactopyranoside;
5-Chloro-3-pyridyl 3-deoxy-3-[4-(3,4-dichlorophenyl)-1H-1,2,3-triazol-1-yl]-1-thio-α-D-galactopyranoside; and
3,4-Dichlorophenyl 3-deoxy-3-[4-(5-chloro-3-pyridyl)-1H-1,2,3-triazol-1-yl]-1-thio-α-D-galactopyranoside.

In a further aspect the present invention relates to a compound of formula (1) for use as a medicine.

In a still further aspect the present invention relates to a pharmaceutical composition comprising the compound of any one of the previous claims and optionally a pharmaceutically acceptable additive, such as a carrier and/or excipient.

In a further aspect the present invention relates to a compound of formula (1) of the present invention for use in a method for treating a disorder relating to the binding of a galectin-3 to a ligand in a mammal, such as a human. In a further embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis.

In a still further aspect the present invention relates to a method for treatment of a disorder relating to the binding of a galectin-3 to a ligand in a mammal, such as a human, wherein a therapeutically effective amount of at least one compound of formula (1) of the present invention is administered to a mammal in need of said treatment. In a further embodiment of the present invention, the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis.

Another aspect of the present invention concerns combination therapy involving administering a compound of formula (1) of the present invention together with a therapeutically active compound different from the compound of formula (1) (interchangeable with "a different therapeutically active compound"). In one embodiment the present invention relates to a combination of a compound of formula (1) and a different therapeutically active compound for use in treatment of a disorder relating to the binding of a galectin-3 to a ligand in a mammal. Such disorders are disclosed below.

In an embodiment of the present invention, a therapeutically effective amount of at least one compound of formula (1) of the present invention is administered to a mammal in need thereof in combination with a different therapeutically active compound. In a further embodiment, said combination of a compound of formula (1) together with a different therapeutically active compound is administered to a mammal suffering from a disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis.

A non-limiting group of cancers given as examples of cancers that may be treated, managed and/or prevented by administration of a compound of formula (1) in combination with a different therapeutically active compound is selected from: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In some aspects of the present invention, the administration of at least one compound of formula (1) of the present invention and at least one additional therapeutic agent demonstrates therapeutic synergy. In some aspects of the methods of the present invention, a measurement of response to treatment observed after administering both at least one compound of formula (1) of the present invention and the additional therapeutic agent is improved over the same measurement of response to treatment observed after administering either the at least one compound of formula (1) of the present invention or the additional therapeutic agent alone.

A further aspect of the present invention concerns combination therapy involving administering a compound of formula (1) of the present invention together with an anti-fibrotic compound different form the compound of formula (1) to a mammal in need thereof. In a further embodiment, such anti-fibrotic compound may be selected from the following non-limiting group of anti-fibrotic compounds: pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, and PBI-4050.

A still further aspect of the present invention concerns combination therapy involving administering a compound of formula (1) in combination with a further conventional cancer treatment such as chemotherapy or radiotherapy, or treatment with immunostimulating substances, gene therapy, treatment with antibodies and treatment using dendritic cells, to a mammal in need thereof.

In an embodiment the compound of formula (1) is administered together with at least one additional therapeutic agent selected from an antineoplastic chemotherapy agent. In a further embodiment, the antineoplastic chemotherapeutic agent is selected from: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In a further embodiment of the present invention, the further conventional cancer treatment includes radiation therapy. In some embodiments, radiation therapy includes localized radiation therapy delivered to the tumor. In some embodiments, radiation therapy includes total body irradiation.

In other embodiments of the present invention the further cancer treatment is selected from the group of immunostimulating substances e.g. cytokines and antibodies. Such cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In some embodiments of the present invention the compound of formula (1) is administered together with at least one additional therapeutic agent selected from a checkpoint inhibitor. In some embodiments of the invention, the checkpoint inhibitor is acting on one or more of the following, non-limiting group of targets: CEACAM1, galectin-9, TIM3, CD80, CTLA4, PD-1, PD-L1, HVEM, BTLA, CD160, VISTA, B7-H4, B7-2, CD155, CD226, TIGIT, CD96, LAG3, GITF, OX40, CD137, CD40, IDO, and TDO. These are known targets and some of these targets are described in Melero et al., Nature Reviews Cancer (2015).

In some embodiments of the present invention the compound of formula (1) is administered together with at least one additional therapeutic agent selected from an inhibitor of indoleamine-2,3-dioxygenase (IDO).

In some embodiments of the present invention the compound of formula (1) is administered together with at least one additional therapeutic agent selected from one or more inhibitors of the CTLA4 pathway. In some embodiments, the inhibitor of the CTLA4 pathway is selected from one or more antibodies against CTLA4.

In some embodiments of the present invention the compound of formula (1) is administered together with at least one additional therapeutic agent selected from one or more inhibitors of the PD-1/PD-L pathway. In some embodiments, the one or more inhibitors of the PD-1/PD-L pathway are selected from one or more antibodies against PD-1, PD-L1, and/or PD-L2.

In a still further aspect the present invention relates to a process of preparing a compound of formula III wherein X and $B^1$ are as defined above under formula (1) or a pharmaceutically acceptable salt or solvate thereof comprising the step a1;

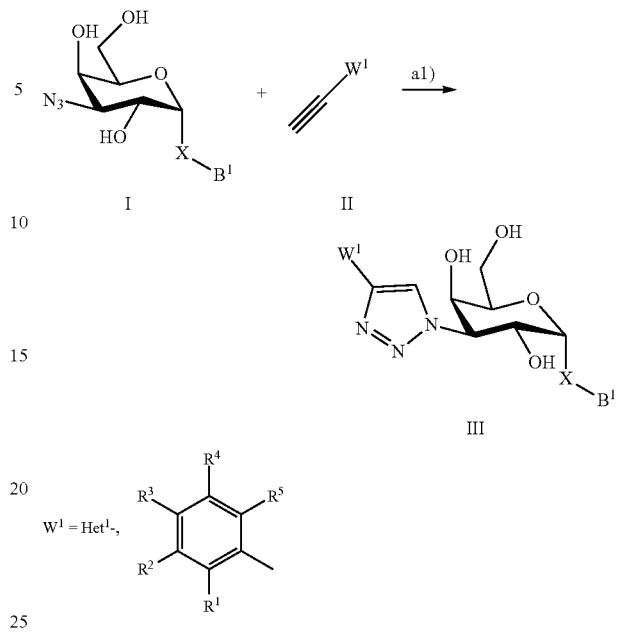

a1) Reacting the compound of formula I, with a compound of formula II in an inert solvent, such as DMF or acetonitrile, using a base, such as diisopropylethylamine, catalyzed by CuI to provide the compound of the formula III.

In a still further aspect the present invention relates to a process of preparing a compound of formula V and/or VI wherein $B^1$ is defined as for formula 1 or a pharmaceutically acceptable salt or solvate thereof comprising the step a2;

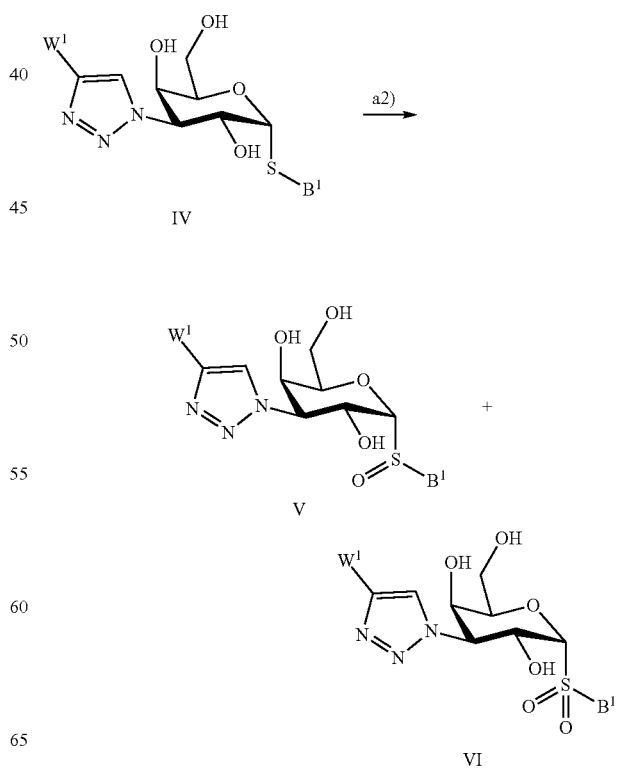

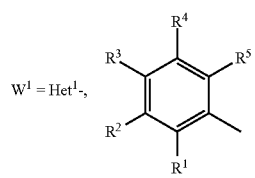

a2) reacting a compound of formula IV with an oxidant such as hydrogen peroxide in a solvent such as acetic acid, alternatively 3-chloroperoxybenzoic acid in an inert solvent such as dichloromethane to give a compound of formula V and/or VI.

In a still further aspect the present invention relates to a process of preparing a compound of formula I wherein X is defined as sulfur and $B^1$ defined as above under formula 1 or a pharmaceutically acceptable salt or solvate thereof comprising the steps a3 and a4;

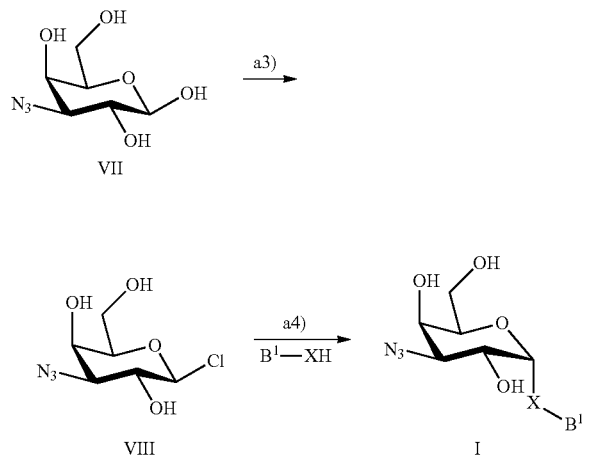

a3) Reacting a compound VII with a chlorinating reagent such as dichloromethylmethylether or $PCl_5$ in the presence of a lewis acid such as $BF_3 \cdot Et_2O$ in an inert solvent as dichloromethane or chloroform to give a compound of formula VIII.

a4) Reacting a compound of the formula VIII with a nucleophile like $B^1$—XH, wherein X is defined as sulfur, in the presence of a base like sodium hydride in an inert solvent such as DMF to give a compound of formula I.

In a still further aspect the present invention relates to a process of preparing a compound of formula I wherein X is defined as sulfur and $B^1$ defined as formula 1 or a pharmaceutically acceptable salt or solvate thereof comprising the steps a5 and a6;

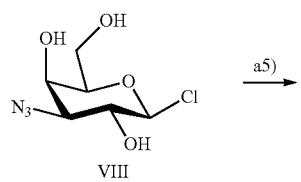

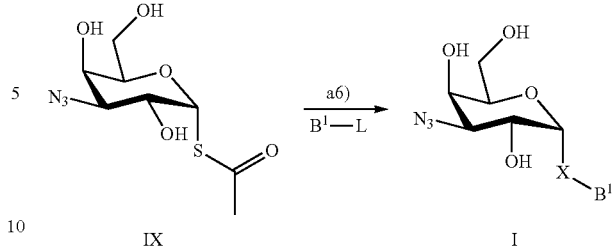

a5) Reacting a compound of formula VIII with a sulfurs nucleophile such as potassium thioacetate to give compound IX in an inert solvent such as DMF.

a6) Reacting a compound of the formula IX with a compound of the formula B-L, wherein L is defined as a leaving group such as Fluorine, Chlorine or Bromine, in an inert solvent as DMF using a base such as dimethylamine to give a compound of the formula I.

In a still further aspect the present invention relates to a process of preparing a compound of formula II comprising the step a7:

$$W^1\text{—}L \xrightarrow{a7} W^1\text{—}{\equiv}$$

X          II $W^1 = Het^1-,$ [aromatic ring with $R^1, R^2, R^3, R^4, R^5$]

a7) Reacting a compound of formula X wherein L is defined as a leaving group such as bromine and $W^1$ defined as above, with trimethylsilane-acetylene using a palladium catalyst such as bis(triphenylphosphine)palladium-(II)-chloride, copper iodide and a base like diisopropylethylamine in an inert solvent, such as THF, to give a compound of formula II.

In a still further aspect the present invention relates to a process of preparing a compound of the formula XIV comprising step a8-a10

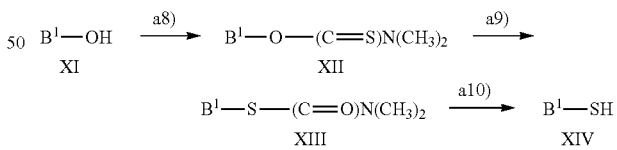

a8) Reacting a compound of the formula XI with an activated thioamide such as dimethylcarbamoyl chloride using a base such as sodium hydride in an inert solvent such as DMF to give a compound of formula XII.

a9) Heating a compound of the formula XII at elevated temperatures to form compound XIII.

a10) Reacting a compound of formula XIII with a base such as potassium hydroxide to give a compound of the formula XIV.

In a still further aspect the present invention relates to a process of preparing a compound of the formula XVI comprising step a11;

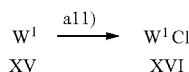

a11) Reacting a compound of formula XV where $W^1$ which is defined as above with a chlorinating reagent such as N-Chlorosuccinimide in an inert solvet to give a chlorinated compound such as XVI.

In a still further aspect the present invention relates to a process of preparing a compound of the formula XVIII comprising step a12;

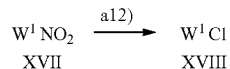

a12) Reacting a compound of formula XVII where $W^1$ which is defined as above with $CuCl_2$ and tert-butyl nitrite to give a compound of formula XVIII.

DETAILED DESCRIPTION OF THE INVENTION

The present compounds of formula (1) differ from prior art compounds in particular in that the pyranose ring is α-D-galactopyranose. Moreover, the present compounds of formula (1) differ from prior art compounds in that they have high affinity due to specific substituents in the 1 and 3 position of the α-D-galactopyranose. It is important to emphasize that the skilled person may expect same or similar activity of both alpha and beta anomers according to known literature, however, the present inventors have found that the present compounds of formula (1) possesses increased affinity to galectin-3 compared to corresponding beta anomers.

In general the compounds of formula (1) are >10 fold better with respect to galectin-3 affinity compared to the corresponding beta-anomers.

In a broad aspect the present invention relates to a D-galactopyranose compound of formula (1)

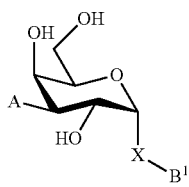

(1)

wherein
the pyranose ring is α-D-galactopyranose,
A is selected from

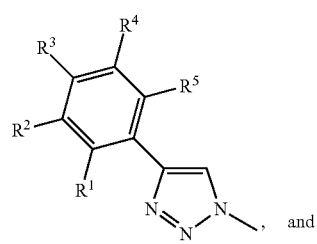

2

, and

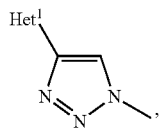

3 wherein $Het^1$ is selected from a pyridinyl, optionally substituted with a group selected from H, CN, Br, Cl, I, F, methyl optionally substituted with a F, $OCH_3$ optionally substituted with a F, and $SCH_3$ optionally substituted with a F; or a pyrimidyl, optionally substituted with a group selected from H, CN, Br, Cl, I, F, methyl optionally substituted with a F, $OCH_3$ optionally substituted with a F, and $SCH_3$ optionally substituted with a F;

wherein $R^1$-$R^5$ are independently selected from a group consisting of H, CN, Br, Cl, I, F, methyl optionally substituted with a F, $OCH_3$ optionally substituted with a F, and $SCH_3$ optionally substituted with a F;

X is selected from S, SO, and $SO_2$;

$B^1$ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and $R^{14}$—CONH— wherein $R^{14}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and $R^{15}$—CONH— wherein $R^{15}$ is selected from $C_{1-3}$ alkyl and cyclopropyl; b) an aryl, such as phenyl or naphthyl, optionally substituted with a group selected from a halogen; CN; —COOH; —$CONR^{22}R^{23}$, wherein $R^{22}$ and $R^{23}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-iso-propyl, optionally substituted with a F; $NR^{28}R^{29}$, wherein $R^{28}$ and $R^{29}$ are independently selected from H, $C_{1-3}$ alkyl and isopropyl; OH; and $R^{16}$—CONH— wherein $R^{16}$ is selected from $C_{1-3}$ alkyl and cyclopropyl; c) a $C_{5-7}$ cycloalkyl, optionally substituted with a substituent selected from a halogen, CN, methyl optionally substituted with a F, $OCH_3$ optionally substituted with a F, $OCH_2CH_3$ optionally substituted with a F, OH, and $R^{17}$—CONH— wherein $R^{17}$ is selected from $C_{1-3}$ alkyl and cyclopropyl; and d) a heterocycle, such as heteroaryl or heterocycloalkyl, optionally substituted with a group selected from a halogen; CN; —COOH; —$CONR^{24}R^{25}$, wherein $R^{24}$ and $R^{25}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-iso-propyl, optionally substituted with a F; $NR^{30}R^{31}$, wherein $R^{30}$ and $R^{31}$ are independently selected from H, $C_{1-3}$ alkyl and isopropyl; OH; and $R^{18}$—CONH— wherein $R^{18}$ is selected from $C_{1-3}$ alkyl and cyclopropyl; e) a $C_{1-6}$ alkyl or branched $C_{3-6}$ alkyl; or
a pharmaceutically acceptable salt or solvate thereof.

In an embodiment A is selected from formula 2 wherein $R^1$-$R^5$ are independently selected from H, halogen, CN, methyl optionally substituted with a F, and OCH$_3$ optionally substituted with a F. In a further embodiment A is selected from formula 2 wherein R$^1$ and R$^5$ are selected from H and R$^2$-R$^4$ are selected from halogen, CN, CH$_3$ and CF$_3$. In a further embodiment A is selected from formula 2 wherein R$^1$ and R$^5$ are selected from H and R$^2$-R$^4$ are selected from F, Cl, Br, CN, CH$_3$ and CF$_3$. In a still further embodiment A is selected from formula 2 wherein R$^1$ and R$^5$ are selected from H and R$^2$ and R$^4$ are selected from F and R$^3$ is selected from Br, Cl, I, CN, CH$_3$ and CF$_3$. In a still further embodiment A is selected from formula 2 wherein R$^1$ and R$^5$ are selected from H and R$^2$ and R$^4$ are selected from F and R$^3$ is selected from Br, Cl, CN, CH$_3$ and CF$_3$. In a further embodiment A is selected from formula 2 wherein R$^1$ and R$^5$ are selected from H and R$^2$ is selected from F, and R$^3$-R$^4$ are selected from Cl. In a further embodiment A is selected from formula 2 wherein R$^1$, R$^2$ and R$^5$ are selected from H and R$^3$ and R$^4$ are selected from halogen, such as F and Cl.

In a further embodiment A is selected from formula 3 wherein Het$^1$ is a pyridinyl optionally substituted with a group selected from halogen. In a still further embodiment A is selected from formula 3 wherein Het$^1$ is an unsubstituted pyridinyl.

In a further embodiment A is selected from formula 3 wherein Het$^1$ is a pyridinyl optionally substituted with a group selected from Br, F, and Cl. In a still further embodiment A is selected from formula 3 wherein Het$^1$ is a pyridinyl substituted with a group selected from F and Cl. In a further embodiment A is selected from formula 3 wherein Het$^1$ is a pyridinyl substituted with one group selected from F and Cl.

In a further embodiment X is selected from S.

In a still further embodiment B$^1$ is selected from an aryl, such as phenyl or naphthyl, optionally substituted with a group selected from a halogen; CN; methyl optionally substituted with a F; OCH$_3$ optionally substituted with a F; OCH$_2$CH$_3$ optionally substituted with a F; OH; R$^{16}$—CONH— wherein R$^{16}$ is selected from C$_{1-3}$ alkyl and cyclopropyl; —COOH; NR$^{28}$R$^{29}$, wherein R$^{28}$ and R$^{29}$ are independently selected from H, C$_{1-3}$ alkyl and isopropyl; and —CONH$_2$. In a further embodiment B$^1$ is selected from a phenyl or phenyl substituted with one, two or three substituents selected from halogen. In a further embodiment B$^1$ is selected from an unsubstituted phenyl. In a still further embodiment B$^1$ is selected from a phenyl substituted with two substituents selected from halogen, such as Cl.

In a further embodiment B$^1$ is selected from a heterocycle, such as heteroaryl or heterocycloalkyl, optionally substituted with a group selected from a halogen; CN; methyl optionally substituted with a F; OCH$_3$ optionally substituted with a F; OCH$_2$CH$_3$ optionally substituted with a F; OH; CONH$_2$; NR$^{30}$R$^{31}$, wherein R$^{30}$ and R$^{31}$ are independently selected from H, C$_{1-3}$ alkyl and isopropyl; and R$^{18}$—CONH— wherein R$^{18}$ is selected from C$_{1-3}$ alkyl and cyclopropyl. In a still further embodiment B$^1$ is selected from a pyridinyl substituted with a group selected from halogen and CN, such as Cl, Br and CN. In a still further embodiment B$^1$ is selected from a pyridinyl substituted with one, two or three substituents selected from halogen and CN, such as Cl, Br and CN. In a still further embodiment B$^1$ is selected from a pyridinyl substituted with one or two substituents selected from halogen and CN, such as Cl, Br and CN.

In a further embodiment the compound of the present invention is selected from:

4-Bromo-5-cyano-2-pyridyl 3-deoxy-3-[4-(3,4,5-trifluorophenyl)-1H-1,2,3-triazol-1-yl]-1-thio-α-D-galactopyranoside;

4-Chloro-5-cyano-2-pyridyl 3-deoxy-3-[4-(3,4,5-trifluorophenyl)-1H-1,2,3-triazol-1-yl]-1-thio-α-D-galactopyranoside;

2-Chloro-4-pyridyl 3-deoxy-3-[4-(3,4,5-trifluorophenyl)-1H-1,2,3-triazol-1-yl]-1-thio-α-D-galactopyranoside;

5-Chloro-2-cyano-3-pyridyl 3-deoxy-3-[4-(3,4,5-trifluorophenyl)-1H-1,2,3-triazol-1-yl]-1-thio-α-D-galactopyranoside;

5-Bromo-6-cyano-3-pyridyl 3-deoxy-3-[4-(3,4,5-trifluorophenyl)-1H-1,2,3-triazol-1-yl]-1-thio-α-D-galactopyranoside;

5-Bromo-2-cyano-3-pyridyl 3-deoxy-3-[4-(3,4,5-trifluorophenyl)-1H-1,2,3-triazol-1-yl]-1-thio-α-D-galactopyranoside;

4-Chloro-2-pyridyl 3-deoxy-3-[4-(3,4,5-trifluorophenyl)-1H-1,2,3-triazol-1l-yl]-1-thio-α-D-galactopyranoside;

5-Bromo-3-pyridyl 3-deoxy-3-[4-(4-chloro-3,5-difluorophenyl)-1H-1,2,3-triazol-1-yl]-1-thio-α-D-galactopyranoside;

5-Chloro-3-pyridyl 3-deoxy-3-[4-(4-chloro-3,5-difluorophenyl)-1H-1,2,3-triazol-1-yl]-1-thio-α-D-galactopyranoside;

5-Chloro-6-cyano-3-pyridyl 3-deoxy-3-[4-(4-chloro-3,5-difluorophenyl)-1H-1,2,3-triazol-1-yl]-1-thio-α-D-galactopyranoside;

5-Bromo-2-cyano-3-pyridyl 3-deoxy-3-[4-(4-chloro-3,5-difluorophenyl)-1H-1,2,3-triazol-1-yl]-1-thio-α-D-galactopyranoside;

5-Bromo-6-cyano-3-pyridyl 3-deoxy-3-[4-(4-chloro-3,5-difluorophenyl)-1H-1,2,3-triazol-1-yl]-1-thio-α-D-galactopyranoside;

5-Chloro-2-cyano-3-pyridyl 3-deoxy-3-[4-(4-chloro-3,5-difluorophenyl)-1H-1,2,3-triazol-1-yl]-1-thio-α-D-galactopyranoside;

5-Chloro-3-pyridyl 3-deoxy-3-[4-(4-cyano-3,5-difluorophenyl)-1H-1,2,3-triazol-1-yl]-1-thio-α-D-galactopyranoside;

5-Chloro-3-pyridyl 3-deoxy-3-[4-(3,5-difluoro-4-trifluoromethyl-phenyl)-1H-1,2,3-triazol-1-yl]-1-thio-α-D-galactopyranoside;

5-Chloro-3-pyridyl 3-deoxy-3-[4-(3,5-difluoro-4-methylphenyl)-1H-1,2,3-triazol-1-yl]-1-thio-α-D-galactopyranoside;

5-Chloro-3-pyridyl 3-deoxy-3-[4-(4-bromo-3,5-difluorophenyl)-1H-1,2,3-triazol-1-yl]-1-thio-α-D-galactopyranoside;

5-Chloro-3-pyridyl 3-deoxy-3-[4-(3,4-dichloro-5-fluorophenyl)-1H-1,2,3-triazol-1-yl]-1-thio-α-D-galactopyranoside;

5-Chloro-3-pyridyl 3-deoxy-3-[4-(4-chloro-3-fluorophenyl)-1H-1,2,3-triazol-1-yl]-1-thio-α-D-galactopyranoside;

3,4-Dichlorophenyl 3-deoxy-3-[4-(5-fluoro-3-pyridyl)-1H-1,2,3-triazol-1-yl]-1-thio-α-D-galactopyranoside;

5-Chloro-3-pyridyl 3-deoxy-3-[4-(3,4-dichlorophenyl)-1H-1,2,3-triazol-1-yl]-1-thio-α-D-galactopyranoside; and 3,4-Dichlorophenyl 3-deoxy-3-[4-(5-chloro-3-pyridyl)-1H-1,2,3-triazol-1-yl]-1-thio-α-D-galactopyranoside.

In a further aspect the present invention relates to a compound of formula (1) of the present invention for use as a medicine.

In a still further aspect the present invention relates to a pharmaceutical composition comprising a compound of formula (1) of the present invention and optionally a pharmaceutically acceptable additive, such as a carrier and/or excipient.

In a further aspect the present invention relates to a compound of formula (1) of the present invention for use in a method for treating a disorder relating to the binding of a galectin-3 to a ligand in a mammal, such as a human. In an embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis. A non-limiting group of cancers given as examples of cancers that may be treated, managed and/or prevented by administration of a compound of formula (1) include: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangcoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer. Each of these disorders is considered a single embodiment and may be made the subject of a claim specifically to such disease or disorder.

In a still further aspect the present invention relates to a method for treatment of a disorder relating to the binding of a galectin-3 to a ligand in a mammal, such as a human, wherein a therapeutically effective amount of at least one compound of formula (1) of the present invention is administered to a mammal in need of said treatment. In an embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis. Each of these disorders are considered a single embodiment and may be made the subject of a claim specifically to such disease or disorder.

The skilled person will understand that it may be necessary to adjust or change the order of steps in the processes a1 to a12, and such change of order is encompassed by the aspects of the process as described above in the reaction schemes and accompanying description of the process steps.

Furthermore, the skilled person will understand that the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g. t-butyldimethylsilyl, t-butyldipheylsilyl or trimethylsilyl), AcO(acetoxy), TBS(t-butyldimethylsilyl), TMS(trimethylsilyl), PMB (p-methoxybensyl), and tetrahydropyranyl. Suitable protecting groups for carboxylic acid include $(C_{1-6})$-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(=N)—NH$_2$, TIPS.

The protection and deprotection of functional groups may take place before or after any reaction in the above mentioned processes.

Furthermore the skilled person will appreciate, that, in order to obtain compounds of the invention in an alternative, and on some occasions more convenient manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

In a still further embodiment the compound (1) is on free form. "On free form" as used herein means a compound of formula (1), either an acid form or base form, or as a neutral compound, depending on the substituents. The free form does not have any acid salt or base salt in addition. In one embodiment the free form is an anhydrate. In another embodiment the free form is a solvate, such as a hydrate.

In a further embodiment the compound (1) is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "$C_{1-x}$ alkyl" as used herein means an alkyl group containing 1-x carbon atoms, e.g. $C_{1-5}$ or $C_{1-6}$, such as methyl, ethyl, propyl, butyl, pentyl or hexyl.

The term "branched $C_{3-6}$ alkyl" as used herein means a branched alkyl group containing 3-6 carbon atoms, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "$C_{5-7}$ cycloalkyl" as used herein means a cyclic alkyl group containing 5-7 carbon atoms, such as cyclopentyl, cyclohexyl, or cycloheptyl.

The term "Oxo" as used herein means an oxygen atom with double bonds, also indicated as =O.

The term "CN" as used herein means a nitril.

The term "a five or six membered heteroaromatic ring" as used herein means one five membered heteroaromatic ring or one six membered heteroaromatic ring. The five membered heteroaromatic ring contains 5 ring atoms of which one to four are heteroatoms selected from N, O, and S. The six membered heteroaromatic ring contains 6 ring atoms of which one to five are heteroatoms selected from N, O and S. Examples include thiophene, furan, pyran, pyrrole, imidazole, pyrazole, isothiazole, isoxazole, pyridine, pyrazine, pyrimidine and pyridazine. When such heteroaromatic rings are substituents they are termed thiophenyl, furanyl, pyranyl, pyrrolyl, imidazolyl, pyrazolyl, isothiazolyl, isooxazolyl, pyridinyl, pyrazinyl, pyrimidinyl and pyridazinyl. Also included are oxazoyl, thiazoyl, thiadiazoly, oxadiazolyl, and pyridonyl.

The term "a heterocycle, such as heteroaryl or heterocycloalkyl" as used herein means a heterocycle consisting of one or more 3-7 membered ring systems containing one or more heteroatoms and wherein such ring systems may optionally be aromatic. The term "a heteroaryl" as used herein means a mono or bicyclic aromatic ringsystem containing one or more heteroatoms, such as 1-10, e.g. 1-6, selected from O, S, and N, including but not limited to oxazolyl, oxadiazolyl, thiophenyl, thiadiazolyl, thiazolyl, pyridyl, pyrimidinyl, pyridonyl, pyrimidonyl, quinolinyl, azaquionolyl, isoquinolinyl, azaisoquinolyl, quinazolinyl, azaquinazolinyl, bensozazoyl, azabensoxazoyl, bensothiazoyl, or azabensothiazoyl. The term "a heterocycloalkyl" as used herein means a mono or bicyclic 3-7 membered alifatic heterocycle containing one or more heteroatoms, such as 1-7, e.g. 1-5, selected from O, S, and N, including but not limited to piperidinyl, tetrahydropyranyl, tetrahydrothipyranyl, or piperidonyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular, a human being, but it may also include animals, such as dogs, cats, cows, sheep and pigs.

The term "a therapeutically effective amount" of a compound of formula (1) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (1) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person skilled within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed.

The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compounds as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context). This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention indiverse forms thereof.

EXPERIMENTAL PROCEDURES

Evaluation of Kd Values

The affinity of Example 1-22 for galectins were determined by a fluorescence anisotropy assay where the compound was used as an inhibitor of the interaction between galectin and a fluorescein tagged saccharide probe as described Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47, (Sörme et al., 2004) and Monovalent interactions of Galectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salomonsson et al., 2010). The assay was also adapted to be able to measure the high affinity of compounds for galectin-3 by using the below probe constructed to have high affinity for galectin-3 which made it possible to use a low concentration of galectin-3 (50 nM). 100 nM albumin was included as a carrier to prevent protein loss at such low concentration of galectin.

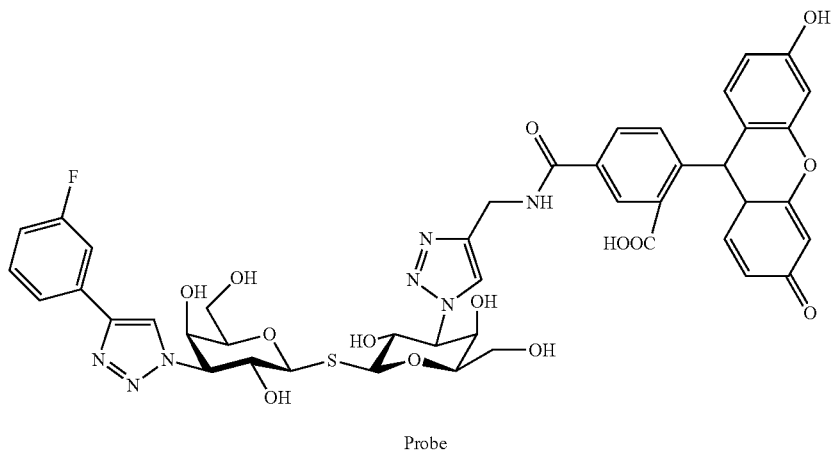
Probe
| Example | IUPAC name | Structure | Galectin-3 (Kd (μM) |
|---|---|---|---|
| 1 | 4-Bromo-5-cyano-2-pyridyl 3-deoxy-3-[4-(3,4,5-trifluorophenyl)-1H-1,2,3-triazol-1-yl]-1-thio-α-D-galactopyranoside | 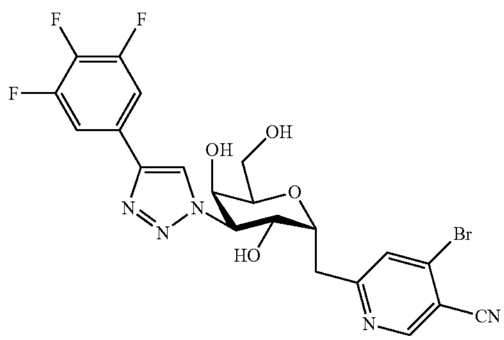 | 0.027 |
| 2 | 4-Chloro-5-cyano-2-pyridyl 3-deoxy-3-[4-(3,4,5-trifluorophenyl)-1H-1,2,3-triazol-1-yl]-1-thio-α-D-galactopyranoside | 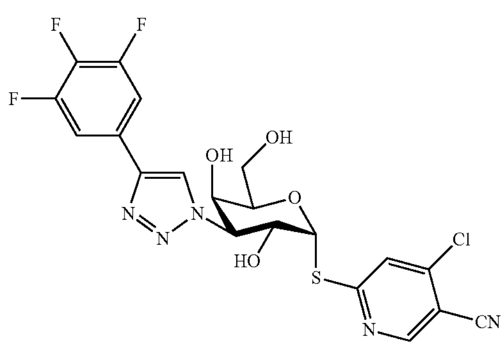 | 0.057 |

-continued

| Example | IUPAC name | Structure | Galectin-3 (Kd (μM) |
|---|---|---|---|
| 3 | 2-Chloro-4-pyridyl 3-deoxy-3-[4-(3,4,5-trifluorophenyl)-1H-1,2,3-triazol-1-yl]-1-thio-α-D-galactopyranoside | 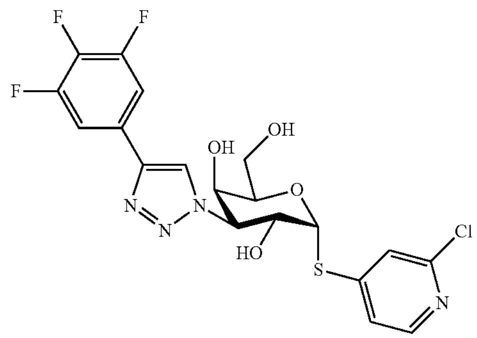 | 0.086 |
| 4 | 5-Chloro-2-cyano-3-pyridyl 3-deoxy-3-[4-(3,4,5-trifluorophenyl)-1H-1,2,3-triazol-1-yl]-1-thio-α-D-galactopyranoside | 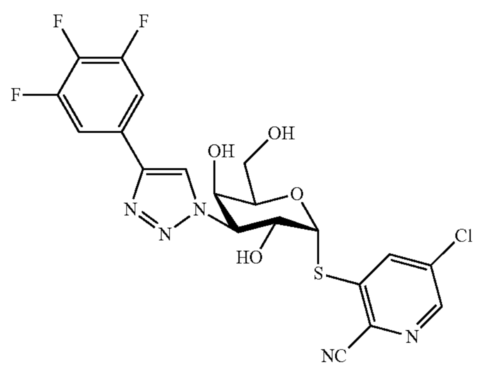 | 0.029 |
| 5 | 5-Bromo-6-cyano-3-pyridyl 3-deoxy-3-[4-(3,4,5-trifluorophenyl)-1H-1,2,3-triazol-1-yl]-1-thio-α-D-galactopyranoside | 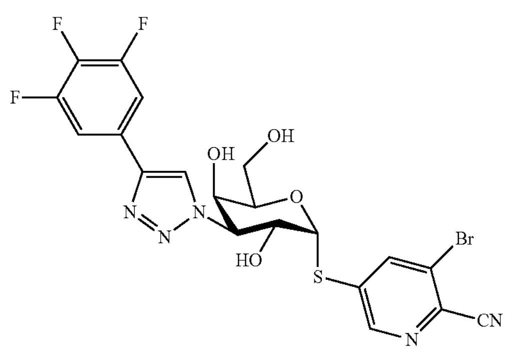 | 0.022 |
| 6 | 5-Bromo-2-cyano-3-pyridyl 3-deoxy-3-[4-(3,4,5-trifluorophenyl)-1H-1,2,3-triazol-1-yl]-1-thio-α-D-galactopyranoside | 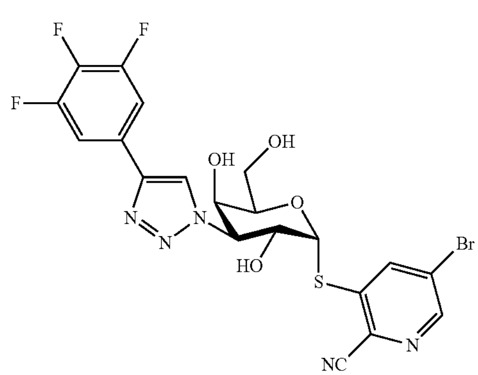 | 0.022 |

-continued

| Example | IUPAC name | Structure | Galectin-3 (Kd) (μM) |
|---|---|---|---|
| 7 | 4-Chloro-2-pyridyl 3-deoxy-3-[4-(3,4,5-trifluorophenyl)-1H-1,2,3-triazol-1-yl]-1-thio-α-D-galactopyranoside | 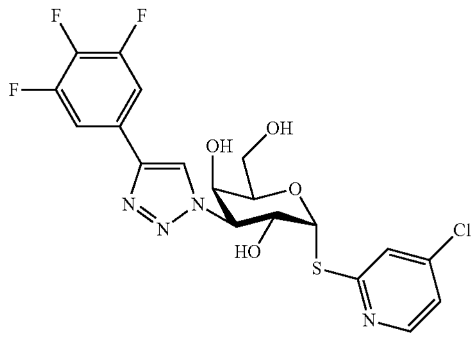 | 0.120 |
| 8 | 5-Bromo-3-pyrdyl 3-deoxy-3-[4-(4-chloro-3,5-difluorophenyl)-1H-1,2,3-triazol-1-yl]-1-thio-α-D-galactopyranoside | 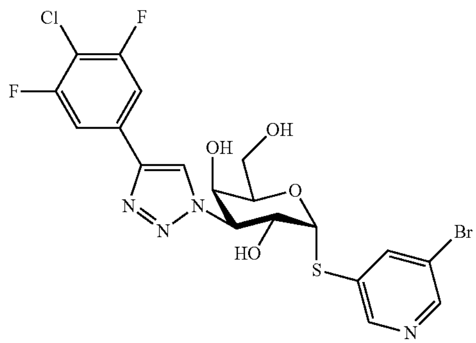 | 0.015 |
| 9 | 5-Chloro-3-pydyl 3-deoxy-3-[4-(4-chloro-3,5-difluorophenyl)-1H-1,2,3-triazol-1-yl]-1-thio-α-D-galactopyranoside | 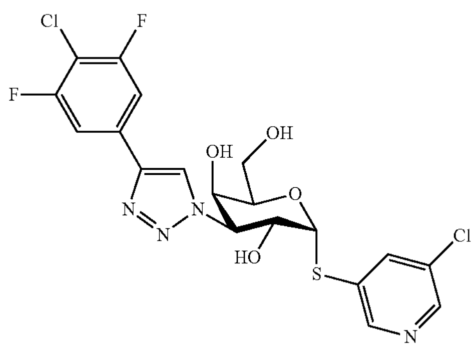 | 0.022 |
| 10 | 5-Chloro-6-cyano-3-pyridyl 3-deoxy-3-[4-(4-chloro-3,5-difluorophenyl)-1H-1,2,3-triazol-1-yl]-1-thio-α-D-galactopyranoside | 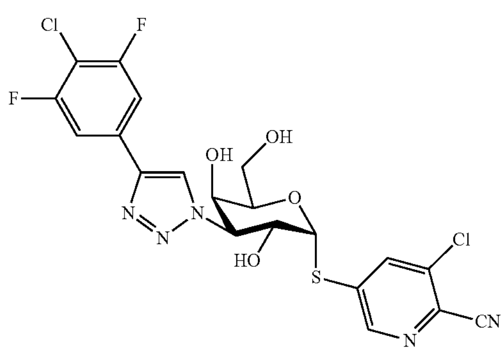 | 0.018 |

| Example | IUPAC name | Structure | Galectin-3 (Kd (μM) |
|---|---|---|---|
| 11 | 5-Bromo-2-cyano-3-pyridyl 3-deoxy-3-[4-(4-chloro-3,5-difluorophenyl)-1H-1,2,3-triazol-1-yl]-1-thio-α-D-galactopyranoside | 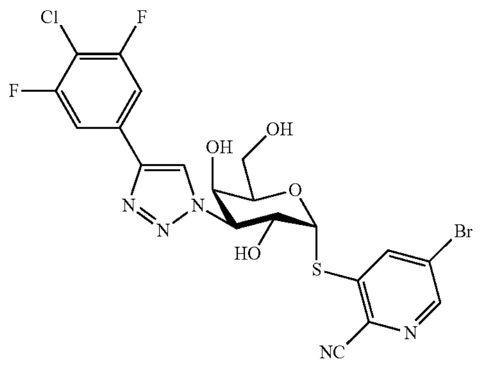 | 0.011 |
| 12 | 5-Bromo-6-cyano-3-pyridyl 3-deoxy-3-[4-(4-chloro-3,5-difluorophenyl)-1H-1,2,3-triazol-1-yl]-1-thio-α-D-galactopyranoside | 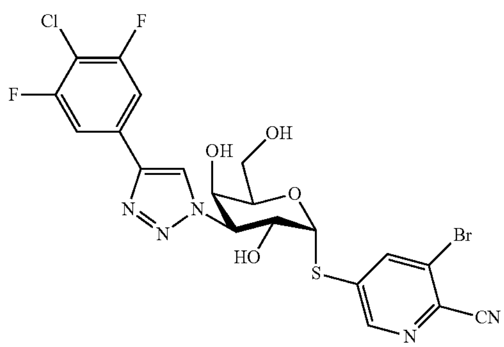 | 0.016 |
| 13 | 5-Chloro-2-cyano-3-pyridyl 3-deoxy-3-[4-(4-chloro-3,5-difluorophenyl)-1H-1,2,3-triazol-1-yl]-1-thio-α-D-galactopyranoside | 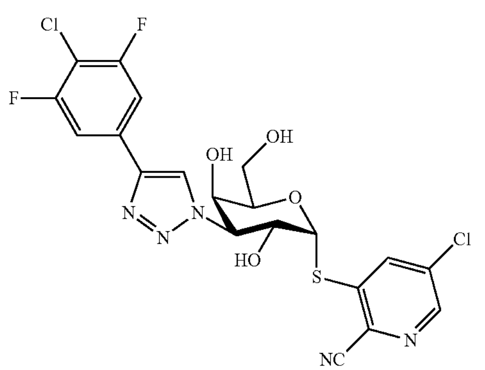 | 0.011 |
| 14 | 5-Chloro-3-pyridyl 3-deoxy-3-[4-(4-cyano-3,5-difluorophenyl)-1H-1,2,3-triazol-1-yl]-1-thio-α-D-galactopyranoside | 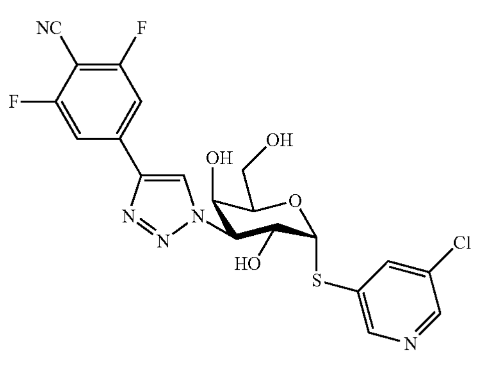 | 0.18 |

| Example | IUPAC name | Structure | Galectin-3 (Kd (μM) |
|---|---|---|---|
| 15 | 5-Chloro-3-pyridyl 3-deoxy-3-[4-(3,5-difluoro-4-trifluoromethyl-phenyl)-1H-1,2,3-triazol-1-yl]-1-thio-α-D-galactopyranoside | 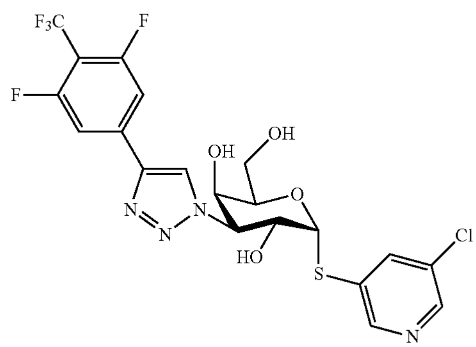 | 0.097 |
| 16 | 5-Chloro-3-pyridyl 3-deoxy-3-[4-(3,5-difluoro-4-methylphenyl)-1H-1,2,3-triazol-1-yl]-1-thio-α-D-galactopyranoside | 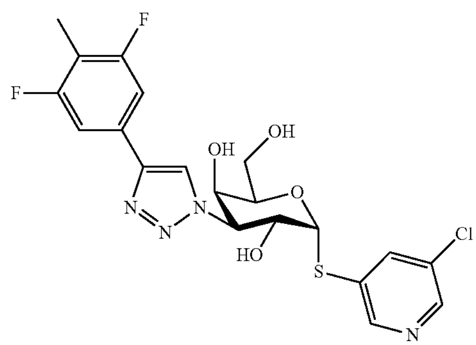 | 0.018 |
| 17 | 5-Chloro-3-pyridyl 3-deoxy-3-[4-(4-bromo-3,5-difluorophenyl)-1H-1,2,3-triazol-1-yl]-1-thio-α-D-galactopyranoside | 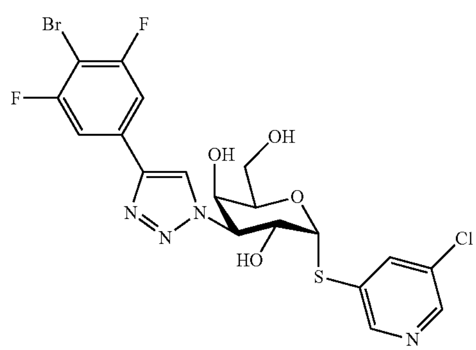 | 0.028 |
| 18 | 5-Chloro-3-pyridyl 3-deoxy-3-[4-(3,4-dichloro-5-fluorophenyl)-1H-1,2,3-triazol-1-yl]-1-thio-α-D-galactopyranoside | 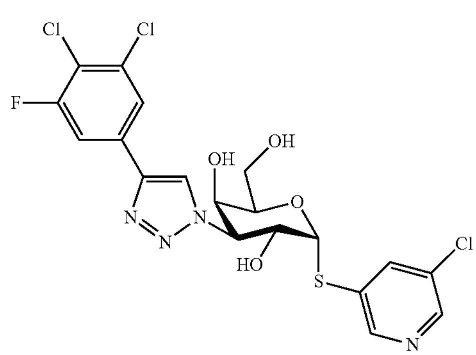 | 0.027 |

-continued

| Example | IUPAC name | Structure | Galectin-3 (Kd (μM) |
|---|---|---|---|
| 19 | 5-Chloro-3-pyridyl 3-deoxy-3-[4-(4-chloro-3-fluorophenyl)-1H-1,2,3-triazol-1-yl]-1-thio-α-D-galactopyranoside | 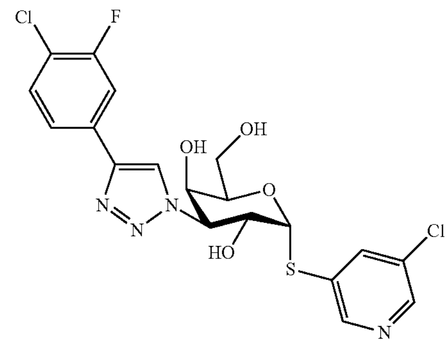 | 0.034 |
| 20 | 3,4-Dichlorophenyl 3-deoxy-3-[4-(5-fluoro-3-pyridyl)-1H-1,2,3-triazol-1-yl]-1-thio-α-D-galactopyranoside | 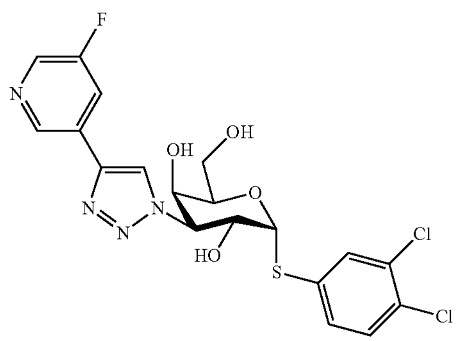 | 0.75 |
| 21 | 5-Chloro-3-pyridyl 3-deoxy-3-[4-(3,4-dichlorophenyl)-1H-1,2,3-triazol-1-yl]-1-thio-α-D-galactopyranoside | 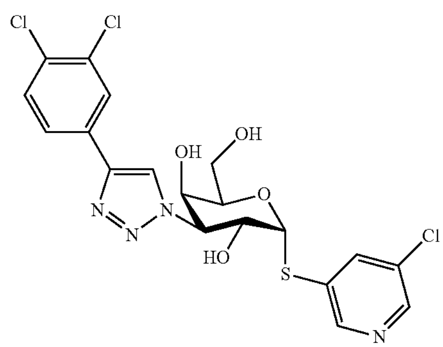 | 0.031 |
| 22 | 3,4-Dichlorophenyl 3-deoxy-3-[4-(5-chloro-3-pyridyl)-1H-1,2,3-triazol-1-yl]-1-thio-α-D-galactopyranoside | 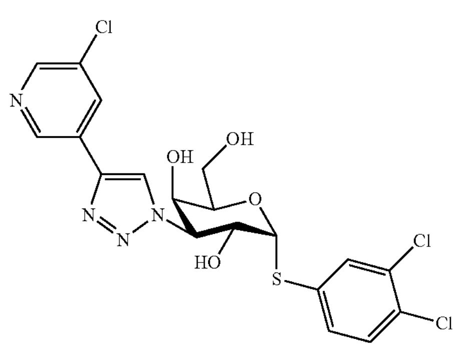 | 0.694 |

| Example | Galectin-1 (Kd (μM)) |
| --- | --- |
| 1 | 2.6 |
| 7 | 6.9 |
| 12 | 7.0 |

Synthesis of Examples and Intermediates

General Procedures:

Nuclear Magnetic Resonance (NMR) spectra were recorded on a 400 MHz Bruker AVANCE III 500 instrument at 25° C. Chemical shifts are reported in ppm using the residual solvent as internal standard. Peak multiplicities are expressed as follow: s, singlet; d, doublet; dd, doublet of doublets; t, triplet; dt, doublet of triplet; q, quartet; m, multiplet; br s, broad singlet.

LC-MS spectra were acquired on an Agilent 1200 HPLC coupled with an Agilent MSD mass spectrometer operating in ES (+) ionization mode. Column: XBridge C18 (4.6×50 mm, 3.5 μm) or SunFire C18 (4.6×50 mm, 3.5 m). Solvent A (0.1% TFA in water) and solvent B (Acetonitrile+0.1% TFA) or solvent A (10 mM Ammonium hydrogen carbonate in water) and solvent B (Acetonitrile). Wavelength: 254 nM. Preparative HPLC was performed on a Gilson 215. Flow: 25 mL/min Column: XBridge prep C18 10 μm OBD (19×250 mm) column. Wavelength: 254 nM. Solvent A (10 mM Ammonium hydrogen carbonate in water) and solvent B (Acetonitrile).

The following abbreviations are used:

Calcd: Calculated
CH$_3$CN: Acetonitrile
DCM: Dichloromethane
DIPEA: N,N-Diisopropylethylamine
DMF: N,N-dimethylformamide
ESI-MS: Electrospray ionization mass spectrometry
EtOAc or EA: Ethylacetate
HPLC: High performance liquid chromatography
MeOH: Methanol
MeOD-d4: Deuterated methanol
MS: Mass spectroscopy
MTBE: tert-butyl methyl ether
NaOMe: Sodium methoxide
NMR: Nuclear magnetic resonance
PE: petroleum ether
Prep: Preparative
rt: Room temperature
TBSOTf: tert-Butyldimethylsilyl trifluoromethanesulfonate
TBME: tert-Butyl methyl ether
TEA: Triethylamine
TFA: trifluoroacetic acid
TMS: Trimethyl silyl
UV: Ultraviolet Example 1-22 were Made from their Corresponding Intermediates i1-i22

Example 1

4-Bromo-5-cyano-2-pyridyl 3-deoxy-3-[4-(3,4,5-trifluorophenyl)-1H-1,2,3-triazol-1-yl]-1-thio-α-D-galactopyranoside

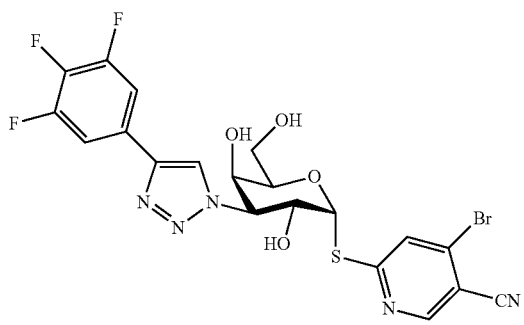

A solution of 4-Bromo-5-cyano-2-pyridyl 2,4,6-tri-O-acetyl-3-deoxy-3-[4-(3,4,5-trifluorophenyl)-1H-1,2,3-triazol-1-yl]-1-thio-α-D-galactopyranoside (40 mg, 0.06 mmol) in MeOH/Et$_3$N/H$_2$O (5/3/1) (2 mL) was stirred at room temperature for 20 h.

The reaction mixture was evaporated to dryness and the residue was purified by HPLC (on C-18 column using a gradient of CH$_3$CN/10 mM NH$_4$HCO$_3$ from 0-42%) to afford the title compound as a white solid (5 mg).

m/z calcd for [C$_{20}$H$_{15}$BrF$_3$N$_5$O$_4$S]$^-$ [M+H]$^+$: 558.0; found: 558.0.

$^1$H NMR (400 MHz, MeOD) δ 8.58 (d, J=5.8 Hz, 2H), 8.14 (s, 1H), 7.68 (dd, J=8.7, 6.7 Hz, 2H), 6.46 (d, J=3.6 Hz, 1H), 5.08 (d, J=3.2 Hz, 2H), 4.27 (t, J=6.1 Hz, 1H), 4.23 (s, 1H), 3.72 (dd, J=6.0, 2.3 Hz, 2H).

Example 2

4-Chloro-5-cyano-2-pyridyl 3-deoxy-3-[4-(3,4,5-trifluorophenyl)-1H-1,2,3-triazol-1-yl]-1-thio-α-D-galactopyranoside

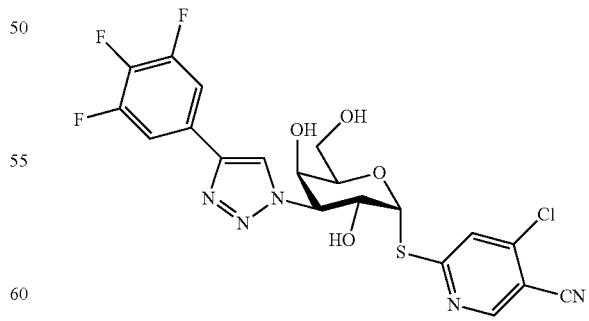

4-Chloro-5-cyano-2-pyridyl 2,4,6-tri-O-acetyl-3-deoxy-3-[4-(3,4,5-trifluorophenyl)-1H-1,2,3-triazol-1-yl]-1-thio-α-D-galactopyranoside (45 mg, 0.07 mmol) was dissolved in MeOH (4 mL). TEA (0.5 ml) and H$_2$O (1 mL) was added. The mixture was stirred at rt for 2 hours. The mixture was concentrated in vacuum and the residue was purified on C-18 column using a gradient of CH₃CN/10 mM NH₄HCO₃ from 0-42% to give the title compound 13 mg (36%).

¹H NMR (400 MHz, DMSO) δ 8.85 (s, 1H), 8.79 (s, 1H), 7.99 (s, 1H), 7.85 (dd, J=9.0, 6.7 Hz, 2H), 6.58 (d, J=5.2 Hz, 1H), 6.24 (d, J=5.0 Hz, 1H), 5.62 (d, J=6.3 Hz, 1H), 4.98-4.90 (m, 1H), 4.90-4.78 (m, 1H), 4.65 (t, J=5.5 Hz, 1H), 4.15-3.96 (m, 2H), 3.58-3.39 (m, 2H).

ESI-MS m/z calcd for [C₂₀H₁₆ClF₃N₅O₄S]⁺ (M+H)⁺: 514.1; found: 514.2.

Example 3

2-Chloro-4-pyridyl 3-deoxy-3-[4-(3,4,5-trifluorophenyl)-1H-1,2,3-triazol-1-yl]-1-thio-α-D-galactopyranoside

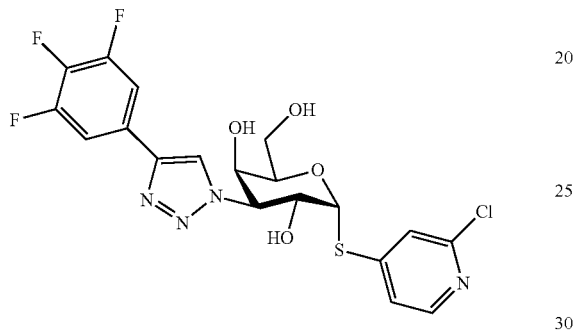

A solution of 2-Chloro-4-pyridyl 2,4,6-tri-O-acetyl-3-deoxy-3-[4-(3,4,5-trifluorophenyl)-1H-1,2,3-triazol-1-yl]-1-thio-α-D-galactopyranoside (45 mg, 0.07 mmol) in MeOH/Et₃N/H₂O (2.5/1.5/0.5)(2 mL) was stirred at room temperature for 4 h. The mixture was evaporated to dryness. The crude product was purified by HPLC to afford product as a white solid 20 mg.

m/z calcd for [C₁₉H₁₆ClF₃N₄O₄S]⁺[M+H]⁺: 489.0; found: 489.0.

¹H NMR (400 MHz, MeOD) δ 8.59 (s, 1H), 8.20 (d, J=5.4 Hz, 1H), 7.75-7.61 (m, 3H), 7.54 (dd, J=5.4, 1.6 Hz, 1H), 6.26 (d, J=4.3 Hz, 1H), 5.04 (dd, J=11.3, 2.1 Hz, 1H), 5.00 (dd, J=11.4, 4.4 Hz, 1H), 4.35 (t, J=6.1 Hz, 1H), 4.20 (s, 1H), 3.81-3.64 (m, 2H).

Example 4

5-Chloro-2-cyano-3-pyridyl 3-deoxy-3-[4-(3,4,5-trifluorophenyl)-1H-1,2,3-triazol-1-yl]-1-thio-α-D-galactopyranoside

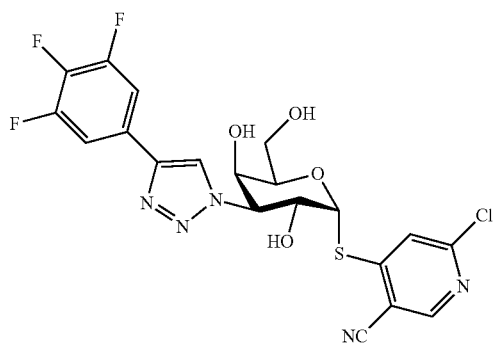

A solution of 5-Chloro-2-cyano-3-pyridyl 2,4,6-tri-O-acetyl-3-deoxy-3-[4-(3,4,5-trifluorophenyl)-1H-1,2,3-triazol-1l-yl]-1-thio-α-D-galactopyranoside (10 mg, 0.015 mmol) in MeOH/Et₃N/H₂O (2.5/1.5/0.5) (1 mL) was stirred at room temperature with for 4 h. The mixture was evaporated to dryness. The crude product was purified by HPLC to afford the title compound as a white solid (6 mg, 75%).

m/z calcd for [C₂₀H₁₅ClF₃N₅O₄S]⁺ [M+H]⁺: 514.0; found: 514.0

¹H NMR (400 MHz, MeOD) δ 8.47 (d, J=1.8 Hz, 2H), 8.35 (d, J=2.1 Hz, 1H), 7.56 (dd, J=8.8, 6.6 Hz, 2H), 6.13 (d, J=5.1 Hz, 1H), 4.98 (dd, J=11.3, 2.7 Hz, 1H), 4.91 (dd, J=11.3, 5.2 Hz, 1H), 4.27 (dd, J=7.7, 4.3 Hz, 1H), 4.11 (d, J=1.9 Hz, 1H), 3.57 (d, J=6.0 Hz, 2H).

Example 5

5-Bromo-6-cyano-3-pyridyl 3-deoxy-3-[4-(3,4,5-trifluorophenyl)-1H-1,2,3-triazol-1-yl]-1-thio-α-D-galactopyranoside

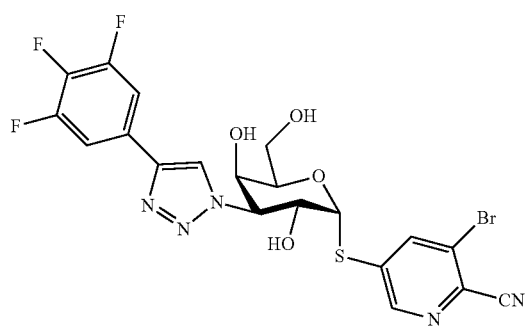

A solution of 5-bromo-6-cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside (20 mg, 0.03 mmol) in MeOH/Et₃N/H₂O (2.5/1.5/0.5) (2 mL) was stirred at room temperature for 4 h. The mixture was evaporated to dryness. The crude product was purified by HPLC to afford the product as a white solid. (10 mg, 60%)

m/z calcd for [C₂₀H₁₅BrF₃N₅O₄S]⁻ [M+H]⁺: 558.0; found: 558.0.

¹H NMR (400 MHz, MeOD) δ 8.66 (d, J=1.8 Hz, 1H), 8.46 (s, 1H), 8.37 (d, J=1.9 Hz, 1H), 7.55 (dd, J=8.7, 6.7 Hz, 2H), 6.09 (d, J=5.1 Hz, 1H), 4.95 (dd, J=11.4, 2.6 Hz, 1H), 4.88 (dd, J=11.4, 5.1 Hz, 1H), 4.25 (t, J=6.0 Hz, 1H), 4.09 (d, J=2.0 Hz, 1H), 3.60 (d, J=6.0 Hz, 2H).

Example 6

5-Bromo-2-cyano-3-pyridyl 3-deoxy-3-[4-(3,4,5-trifluorophenyl)-1H-1,2,3-triazol-1-yl]-1-thio-α-D-galactopyranoside

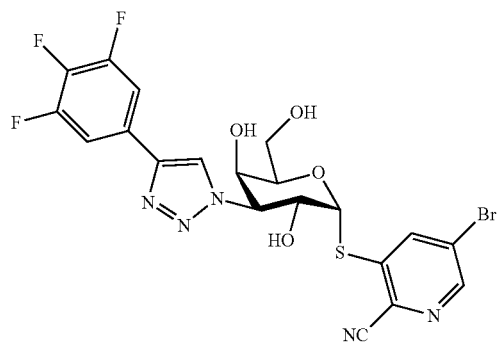

A solution of 5-Bromo-2-Cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside (10 mg, 0.015 mmol) in MeOH/Et$_3$N/H$_2$O (2.5/1.5/0.5) (1 mL) was stirred at room temperature for 4 h. The mixture was evaporated to dryness. The crude product was purified by HPLC to afford the title compound as a white solid. (8.2 mg, 37%) m/z calcd for $[C_{20}H15BrF_3N_5O_4S]^-$ [M+H]$^+$: 558.0; found: 558.0.

$^1$H NMR (400 MHz, MeOD) δ 8.57 (d, J=2.0 Hz, 1H), 8.50 (d, J=2.0 Hz, 1H), 8.47 (s, 1H), 7.56 (dd, J=8.8, 6.6 Hz, 2H), 6.12 (d, J=5.2 Hz, 1H), 4.98 (dd, J=11.3, 2.7 Hz, 1H), 4.91 (dd, J=11.3, 5.2 Hz, 1H), 4.27 (t, J=6.0 Hz, 1H), 4.11 (d, J=2.1 Hz, 1H), 3.59-3.54 (m, 2H).

Example 7

4-Chloro-2-pyridyl 3-deoxy-3-[4-(3,4,5-trifluorophenyl)-1H-1,2,3-triazol-1-yl]-1-thio-α-D-galactopyranoside

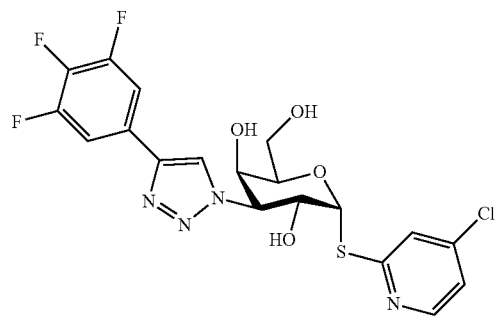

4-Chloro-2-pyridyl 2,4,6-tri-O-acetyl-3-deoxy-3-[4-(3,4,5-trifluorophenyl)-1H-1,2,3-triazol-1-yl]-1-thio-α-D-galactopyranoside (25 mg, 0.04 mmol) was dissolved in NaOCH$_3$/methanol (0.05 M, 2 mL). Then the mixture was stirred at room temperature for 2 h. After completion, DOWEX 50wx8-200 Ion exchange resin was added (PH=7) and reaction mixture was filtered. The effluent was concentrated and the residue was purified by preparative HPLC to give the title compound (8 mg, 31%) as a white solid.

$^1$H NMR (400 MHz, MeOD) δ 8.57 (s, 1H), 8.38 (d, J=5.2 Hz, 1H), 7.70-7.65 (m, 3H), 7.28 (dd, J=5.6, 2.0 Hz, 2H), 6.56 (d, J=4.4 Hz, 1H), Hz, 2H), 4.90-5.02 (m, 2H), 4.35 (t, J=6.0 Hz, 1H), 4.21 (d, J=0.8 Hz, 1H), 3.90 (s, 1H), 3.73-3.67 (m, 2H).

m/z calcd for $[C_{19}H_{16}ClF_3N_4O_4S]^+$[M+H]$^+$: 489.0; found: 489.0.

Example 8

5-Bromo-3-pyridyl 3-deoxy-3-[4-(4-chloro-3,5-difluorophenyl)-1H-1,2,3-triazol-1-yl]-1-thio-α-D-galactopyranoside

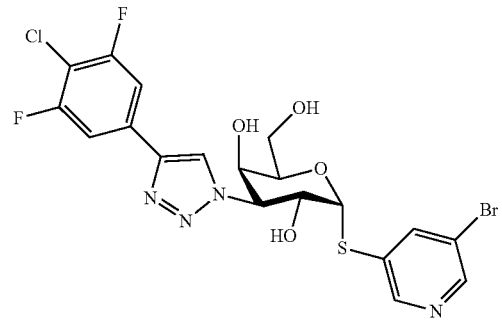

To a solution of 5-Bromo-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside (40 mg, 0.06 mmol) in MeOH/Et$_3$N/H$_2$O (10/3/1) (2 mL) was stirred at room temperature for 20 h. The mixture was evaporated to dryness and the residue was purified by preparative HPLC to afford the title compound as a white solid. (20 mg, 61%).

ESI-MS m/z calcd for $[C_{19}H_{16}BrClF_2N_4O_4S]^+$[M+H]$^+$: 549.0; found: 549.0

$^1$H NMR (400 MHz, MeOD) δ 8.69 (d, J=1.8 Hz, 1H), 8.62 (s, 1H), 8.58 (d, J=2.1 Hz, 1H), 8.34 (t, J=2.0 Hz, 1H), 7.68 (d, J=8.0 Hz, 2H), 5.93 (d, J=5.2 Hz, 1H), 5.05 (dd, J=11.4, 2.8 Hz, 1H), 4.96 (dd, J=11.4, 5.3 Hz, 1H), 4.51 (t, J=6.0 Hz, 1H), 4.22 (d, J=1.9 Hz, 1H), 3.80-3.64 (m, 2H).

Example 9

5-Chloro-3-pyridyl 3-deoxy-3-[4-(4-chloro-3,5-difluorophenyl)-1H-1,2,3-triazol-1-yl]-1-thio-α-D-galactopyranoside

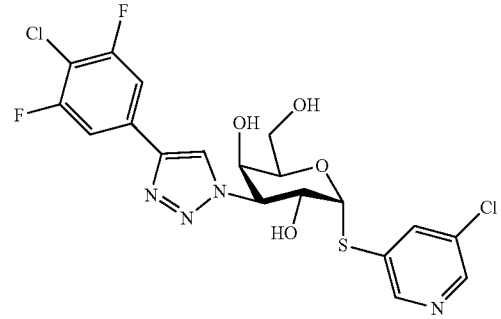

5-Chloro-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside (45 mg, 0.07 mmol) was dissolved in NaOCH$_3$/methanol (0.05 M, 2 mL). The reaction mixture was stirred at room temperature with for 2 h. After completion, DOWEX 50wx8-200 Ion exchange resin was added (pH=7) and the mixture was filtered. The filtrate was concentrated to give a residue which was purified by preparative HPLC to give the title compound (22 mg, 62%) as a white solid.

m/z calcd for $[C_{19}H_{16}Cl_2F_2N_4O_4S]^+[M+H]^+$: 505.0; found: 505.0.

$^1$H NMR (400 MHz, MeOD) δ 8.66 (d, J=1.9 Hz, 1H), 8.63 (s, 1H), 8.49 (d, J=2.2 Hz, 1H), 8.21 (t, J=2.1 Hz, 1H), 7.69 (d, J=8.0 Hz, 2H), 5.94 (d, J=5.2 Hz, 1H), 5.05 (dd, J=11.4, 2.7 Hz, 1H), 4.96 (dd, J=11.4, 5.2 Hz, 1H), 4.51 (t, J=6.2 Hz, 1H), 4.22 (d, J=1.8 Hz, 1H), 3.77-3.66 (m, 2H).

Example 10

5-Chloro-6-cyano-3-pyridyl 3-deoxy-3-[4-(4-chloro-3,5-difluorophenyl)-1H-1,2,3-triazol-1-yl]-1-thio-α-D-galactopyranoside

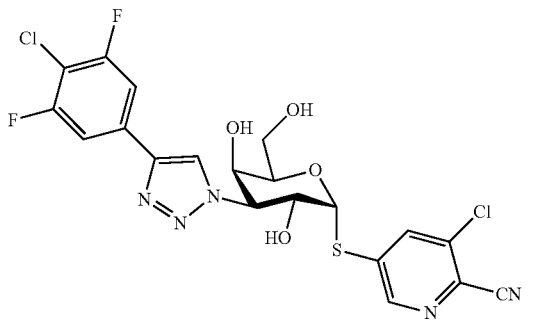

A solution of 5-Chloro-6-cyano-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside (80 mg, 0.12 mmol) in MeOH/Et$_3$N/H$_2$O (0.5/0.3/0.1) (0.9 mL) was stirred at room temperature for 4 h. The mixture was evaporated to dryness. The crude product was purified by preparative HPLC to afford product as a white solid. (17 mg, 26%).

m/z calcd for $[C_{20}H_{15}Cl_2F_2N_5O_4S]^+[M+H]^+$: 530.0; found: 530.0.

$^1$H NMR (400 MHz, MeOD) δ 8.74 (d, J=1.9 Hz, 1H), 8.64 (s, 1H), 8.36 (d, J=1.9 Hz, 1H), 7.72-7.62 (m, 2H), 6.23 (d, J=5.2 Hz, 1H), 5.08 (dd, J=11.4, 2.7 Hz, 1H), 5.00 (dd, J=11.4, 5.2 Hz, 1H), 4.37 (t, J=6.0 Hz, 1H), 4.20 (d, J=1.8 Hz, 1H), 3.71 (d, J=6.0 Hz, 2H).

Example 11

5-Bromo-2-cyano-3-pyridyl 3-deoxy-3-[4-(4-chloro-3,5-difluorophenyl)-1H-1,2,3-triazol-1-yl]-1-thio-α-D-galactopyranoside

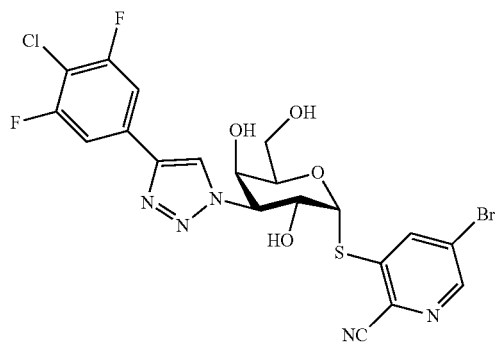

A solution of 5-Bromo-2-cyano-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside (20 mg, 0.015 mmol) in MeOH/Et$_3$N/H$_2$O (0.5/0.3/0.1) (0.9 mL) was stirred at room temperature with for 4 h. The mixture was evaporated to dryness. The crude product was purified by preparative HPLC to afford product as a white solid (7 mg, 43%).

m/z calcd for $[C_{20}H_{15}BrClF_2N_5O_4S]^+[M+H]f$: 574.0; found: 574.0.

$^1$H NMR (400 MHz, MeOD) δ 8.52 (d, J=2.0 Hz, 1H), 8.46 (s, 1H), 8.44 (d, J=2.0 Hz, 1H), 7.51 (d, J=7.9 Hz, 2H), 6.06 (d, J=5.2 Hz, 1H), 4.93 (dd, J=11.3, 2.8 Hz, 1H), 4.85 (dd, J=11.3, 5.2 Hz, 1H), 4.21 (t, J=6.0 Hz, 1H), 4.05 (d, J=2.0 Hz, 1H), 3.55-3.48 (m, 2H).

Example 12

5-Bromo-6-cyano-3-pyridyl 3-deoxy-3-[4-(4-chloro-3,5-difluorophenyl)-1H-1,2,3-triazol-1-yl]-1-thio-α-D-galactopyranoside

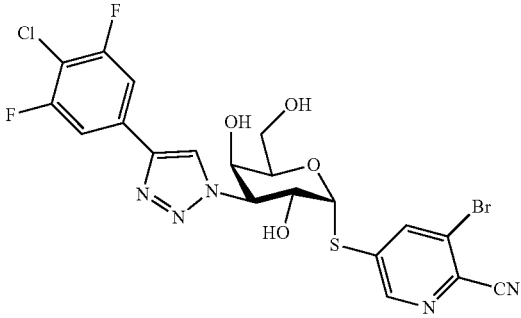

A solution of 5-bromo-6-cyano-3-pyridyl 2,4,6-tri-O-acetyl-3-azido-3-deoxy-1-thio-α-D-galactopyranoside (80 mg, 0.11 mmol) in MeOH/Et$_3$N/H$_2$O (0.5/0.3/0.1) (0.9 mL) was stirred at room temperature for 4 h. The mixture was evaporated to dryness. The crude product was purified by preparative HPLC to afford the title compound as a white solid (15 mg, 22.9%).

m/z calcd for [C₂₀H₁₅BrClF₂N₅O₄S]⁺[M+H]⁺: 574.0; found: 574.0.

¹H NMR (400 MHz, MeOD) δ 8.78 (d, J=1.9 Hz, 1H), 8.63 (s, 1H), 8.50 (d, J=1.9 Hz, 1H), 7.69 (d, J=7.9 Hz, 2H), 6.21 (d, J=5.2 Hz, 1H), 5.07 (dd, J=11.4, 2.7 Hz, 1H), 5.00 (dd, J=11.4, 5.2 Hz, 1H), 4.37 (t, J=6.2 Hz, 1H), 4.20 (d, J=1.8 Hz, 1H), 3.71 (d, J=6.0 Hz, 2H).

Example 13

5-Chloro-2-cyano-3-pyridyl 3-deoxy-3-[4-(4-chloro-3,5-difluorophenyl)-1H-1,2,3-triazol-1-yl]-1-thio-α-D-galactopyranoside

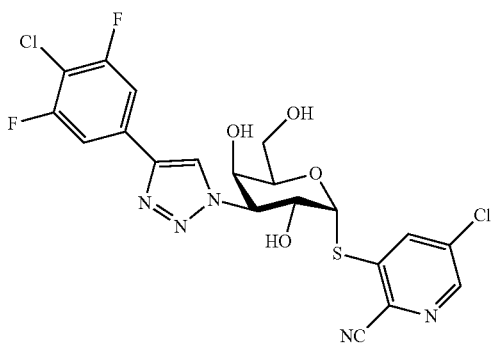

To a solution of 5-Chloro-2-cyano-3-pyridyl 2,4,6-tri-O-acetyl-3-azido-3-deoxy-1-thio-α-D-galactopyranoside (30 mg, 0.04 mmol) in MeOH/Et₃N/H₂O (0.5/0.3/0.1) (0.9 mL) was stirred at room temperature for 4 h. The mixture was evaporated to dryness.

The crude product was purified by preparative HPLC to afford the title compound as a white solid (10 mg, 41%).

m/z calcd for [C₂₀H₁₅Cl₂F₂N₅O₄S]⁺[M+H]⁺: 530.0; found: 530.0.

¹H NMR (400 MHz, MeOD) δ 8.46 (s, 1H), 8.41 (d, J=2.1 Hz, 1H), 8.29 (d, J=2.1 Hz, 1H), 7.51 (d, J=8.0 Hz, 2H), 6.08 (d, J=5.2 Hz, 1H), 4.93 (dd, J=11.3, 2.7 Hz, 1H), 4.86 (dd, J=11.3, 5.2 Hz, 1H), 4.21 (t, J=6.1 Hz, 1H), 4.05 (d, J=1.8 Hz, 1H), 3.51 (d, J=6.1 Hz, 2H).

Example 14

5-Chloro-3-pyridyl 3-deoxy-3-[4-(4-cyano-3,5-difluorophenyl)-1H-1,2,3-triazol-1-yl]-1-thio-α-D-galactopyranoside

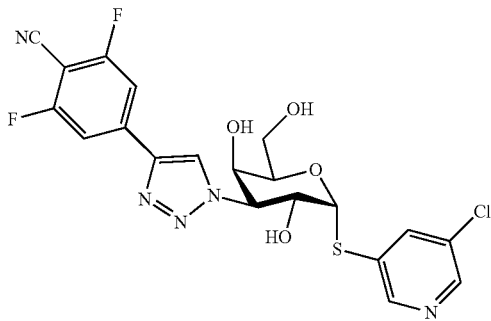

A solution of 5-chloro-3-pyridyl 2,4,6-tri-O-acetyl-3-deoxy-3-[4-(4-cyano-3,5-difluorophenyl)-1H-1,2,3-triazol-1-yl]-1-thio-α-D-galactopyranoside (42 mg, 0.07 mmol) in MeOH/Et₃N/H₂O (5/3/1) (1.8 mL) was stirred at room temperature for 20 h.

The mixture was evaporated to dryness and the residue was purified by preparative HPLC to afford the title compound as a white solid (25 mg, 75%).

m/z calcd for [C₂₀H₁₆ClF₂N₅O₄S]⁻ [M+H]⁺: 497.0; found: 497.0.

¹H NMR (400 MHz, MeOD) δ 8.78 (s, 1H), 8.66 (d, J=1.9 Hz, 1H), 8.49 (d, J=2.2 Hz, 1H), 8.21 (t, J=2.1 Hz, 1H), 7.81 (d, J=8.9 Hz, 2H), 5.95 (d, J=5.3 Hz, 1H), 5.07 (dd, J=11.4, 2.8 Hz, 1H), 4.96 (dd, J=11.4, 5.3 Hz, 1H), 4.51 (t, J=6.1 Hz, 1H), 4.22 (d, J=1.9 Hz, 1H), 3.80-3.66 (m, 2H).

Example 15

5-Chloro-3-pyridyl 3-deoxy-3-[4-(3,5-difluoro-4-trifluoromethyl-phenyl)-1H-1,2,3-triazol-1-yl]-1-thio-α-D-galactopyranoside

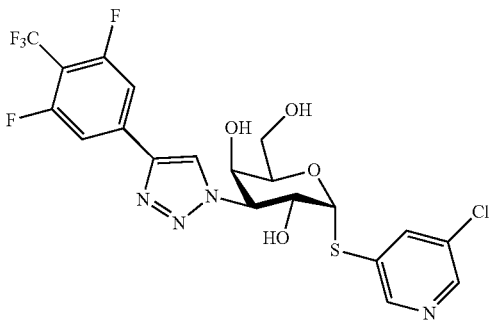

A solution of 5-Chloro-3-pyridyl 2,4,6-tri-O-acetyl-3-deoxy-3-[4-(3,5-difluoro-4-trifluoromethyl-phenyl)-1H-1,2,3-triazol-1-yl]-1-thio-α-D-galactopyranoside (33 mg, 0.05 mmol) in MeOH/Et₃N/H₂O (5/3/1) (1.8 mL) was stirred at room temperature for 20 h. The mixture was evaporated to dryness and the residue was purified by preparative HPLC to afford the title compound as a white solid (23 mg, 86%).

m/z calcd for [C₂₀H₁₆ClF₅N₄O₄S]⁻ [M+H]⁺: 539.0; found: 539.0.

¹H NMR (400 MHz, MeOD) δ 8.74 (s, 1H), 8.66 (d, J=1.8 Hz, 1H), 8.49 (d, J=2.2 Hz, 1H), 8.21 (t, J=2.1 Hz, 1H), 7.74 (d, J=10.9 Hz, 2H), 5.95 (d, J=5.3 Hz, 1H), 5.07 (dd, J=11.4, 2.8 Hz, 1H), 4.97 (dd, J=11.4, 5.3 Hz, 1H), 4.51 (t, J=6.0 Hz, 1H), 4.22 (d, J=1.9 Hz, 1H), 3.77-3.68 (m, 2H).

Example 16

5-Chloro-3-pyridyl 3-deoxy-3-[4-(3,5-difluoro-4-methylphenyl)-1H-1,2,3-triazol-1-yl]-1-thio-α-D-galactopyranoside

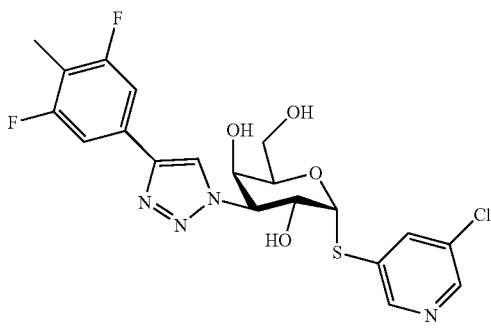

A solution of 5-Chloro-3-pyridyl 3-deoxy-3-[4-(3,5-difluoro-4-methylphenyl)-1H-1,2,3-triazol-1-yl]-1-thio-α-D-galactopyranoside (50 mg, 0.10 mmol) in MeOH/Et$_3$N/H$_2$O (5/3/1) (1.8 mL) was stirred at room temperature for 20 h. The mixture was evaporated to dryness and the residue was purified by preparative HPLC to afford the title compound as a white solid (35 mg, 88.2%).

m/z calcd for [C$_{20}$H$_{19}$ClF$_2$N$_4$O$_4$S]$^-$ [M+H]$^+$: 485.0; found: 485.0.

1H NMR (400 MHz, MeOD) δ 8.48 (d, J=1.8 Hz, 1H), 8.36 (s, 1H), 8.31 (d, J=2.2 Hz, 1H), 8.03 (t, J=2.1 Hz, 1H), 7.33-7.22 (m, 2H), 5.77 (d, J=5.2 Hz, 1H), 4.86 (dd, J=11.4, 2.8 Hz, 1H), 4.79 (dd, J=11.4, 5.2 Hz, 1H), 4.33 (t, J=6.2 Hz, 1H), 4.04 (d, J=1.7 Hz, 1H), 3.61-3.48 (m, 2H).

Example 17

5-Chloro-3-pyridyl 3-deoxy-3-[4-(4-bromo-3,5-difluorophenyl)-1H-1,2,3-triazol-1-yl]-1-thio-α-D-galactopyranoside

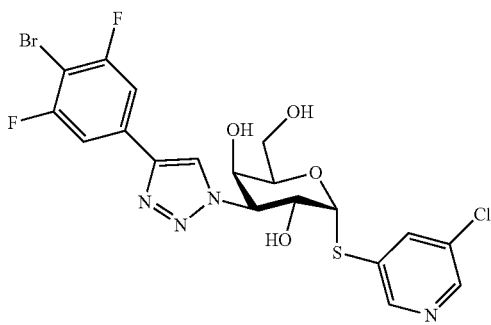

A solution of 5-Chloro-3-pyridyl 2,4,6-tri-O-acetyl-3-deoxy-3-[4-(4-bromo-3,5-difluorophenyl)-1H-1,2,3-triazol-1-yl]-1-thio-α-D-galactopyranoside (65 mg, 0.10 mmol) in MeOH/Et$_3$N/H$_2$O (5/3/1) (1.8 mL) was stirred at room temperature for 20 h. The mixture was evaporated to dryness and the residue was purified by preparative HPLC to afford the title compound as a white solid (38 mg, 71.9%).

m/z calcd for [C$_{19}$H$_{16}$BrClF$_2$N$_4$O$_4$S]$^-$ [M+H]$^+$: 549.0; found: 549.0.

1H NMR (400 MHz, MeOD) δ 8.66 (d, J=1.8 Hz, 1H), 8.64 (s, 1H), 8.49 (d, J=2.2 Hz, 1H), 8.21 (t, J=2.1 Hz, 1H), 7.65 (d, J=7.6 Hz, 2H), 5.95 (d, J=5.2 Hz, 1H), 5.05 (dd, J=11.4, 2.7 Hz, 1H), 4.96 (dd, J=11.4, 5.3 Hz, 1H), 4.51 (t, J=5.8 Hz, 1H), 4.22 (d, J=1.9 Hz, 1H), 3.78-3.66 (m, 2H).

Example 18

5-Chloro-3-pyridyl 3-deoxy-3-[4-(3,4-dichloro-5-fluorophenyl)-1H-1,2,3-triazol-1-yl]-1-thio-α-D-galactopyranoside

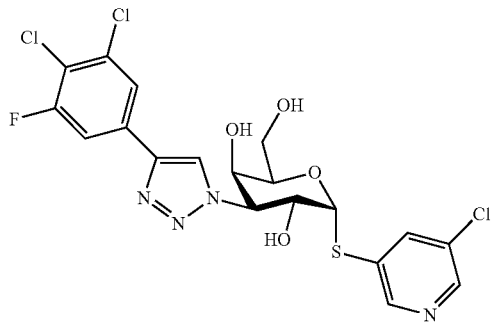

5-Chloro-3-pyridyl 2,4,6-tri-O-acetyl-3-deoxy-3-[4-(3,4-dichloro-5-fluorophenyl)-1H-1,2,3-triazol-1-yl]-1-thio-α-D-galactopyranoside (30.0 mg, 0.046 mmol) was dissolved in water (1 ml), methanol (2 ml), TEA (0.5 ml). The mixture was stirred at rt for 5 h.

Then the mixture was concentrated and purified by Prep-TLC eluted with DCM/MeOH (15/1) to give the title compound 15 mg (62.1%).

1H NMR (400 MHz, MeOD) δ 8.48 (d, J=1.8 Hz, 1H), 8.46 (s, 1H), 8.31 (d, J=2.2 Hz, 1H), 8.03 (t, J=2.0 Hz, 1H), 7.78 (d, J=1.6 Hz, 1H), 7.61 (dd, J=9.7, 1.8 Hz, 1H), 5.77 (d, J=5.2 Hz, 1H), 4.87 (dd, J=11.4, 2.7 Hz, 1H), 4.79 (dd, J=11.4, 5.2 Hz, 1H), 4.33 (t, J=5.9 Hz, 1H), 4.04 (d, J=1.8 Hz, 1H), 3.59-3.48 (m, 2H).

m/z calcd for [C19H16Cl3FN4O4S]$^-$ [M+H]$^+$: 521; found: 521.

Example 19

5-Chloro-3-pyridyl 3-deoxy-3-[4-(4-chloro-3-fluorophenyl)-1H-1,2,3-triazol-1-yl]-1-thio-α-D-galactopyranoside

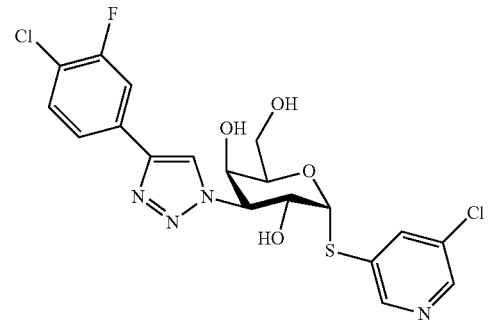

A solution of 5-Chloro-3-pyridyl 2,4,6-tri-O-acetyl-3-deoxy-3-[4-(4-chloro-3-fluorophenyl)-1H-1,2,3-triazol-1-yl]-1-thio-α-D-galactopyranoside (60 mg, 0.10 mmol) in MeOH/Et₃N/H₂O (5/3/1) (1.8 mL) was stirred at room temperature for 20 h. The mixture was evaporated to dryness and the residue was purified by preparative HPLC to afford the title compound as a white solid. (18 mg, 37.8%).

m/z calcd for [C₁₉H₁₇Cl₂FN₄O₄S]⁻ [M+H]⁺: 487.0; found: 487.0.

¹H NMR (400 MHz, MeOD) δ 8.66 (d, J=1.9 Hz, 1H), 8.56 (s, 1H), 8.49 (d, J=2.2 Hz, 1H), 8.21 (t, J=2.1 Hz, 1H), 7.79 (dd, J=10.4, 1.9 Hz, 1H), 7.70 (dd, J=8.3, 1.3 Hz, 1H), 7.57 (t, J=8.0 Hz, 1H), 5.95 (d, J=5.2 Hz, 1H), 5.05 (dd, J=11.4, 2.8 Hz, 1H), 4.97 (dd, J=11.4, 5.2 Hz, 2H), 4.51 (t, J=6.2 Hz, 1H), 4.22 (d, J=1.9 Hz, 1H), 3.78-3.68 (m, 2H).

Example 20

3,4-Dichlorophenyl 3-deoxy-3-[4-(5-fluoro-3-pyridyl)-1H-1,2,3-triazol-1-yl]-1-thio-α-D-galactopyranoside

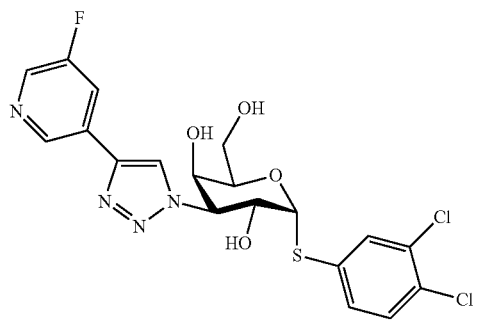

5-Chloro-3-pyridyl 2,4,6-tri-O-acetyl-3-deoxy-3-[4-(4-chloro-3-fluorophenyl)-1H-1,2,3-triazol-1-yl]-1-thio-α-D-galactopyranoside (45.0 mg, 0.073 mmol) was dissolved in water (1 ml), methanol (2 ml), TEA (0.5 ml). The mixture was stirred at rt for 5 h.

Then the mixture was concentrated and purified by preparative-TLC eluted with DCM/MeOH (15/1) to give the title compound. 5 mg (14.0%). 1H NMR (400 MHz, MeOD) δ 8.95 (s, 1H), 8.70 (s, 1H), 8.47 (d, J=2.4 Hz, 1H), 8.18-8.10 (m, 1H), 7.83 (d, J=2.0 Hz, 1H), 7.56 (dd, J=8.4, 2.0 Hz, 1H), 7.50 (d, J=8.4 Hz, 1H), 5.88 (d, J=5.3 Hz, 1H), 5.04 (dd, J=11.4, 2.7 Hz, 1H), 4.96 (dd, J=11.5, 5.2 Hz, 1H), 4.52 (t, J=6.1 Hz, 1H), 4.23 (d, J=1.8 Hz, 1H), 3.81-3.68 (m, 2H).

m/z calcd for [C19H17Cl2FN4O4S]⁺[M+H]⁺: 487, 489; found: 487, 489.

Example 21

5-Chloro-3-pyridyl 3-deoxy-3-[4-(3,4-dichlorophenyl)-1H-1,2,3-triazol-1-yl]-1-thio-α-D-galactopyranoside

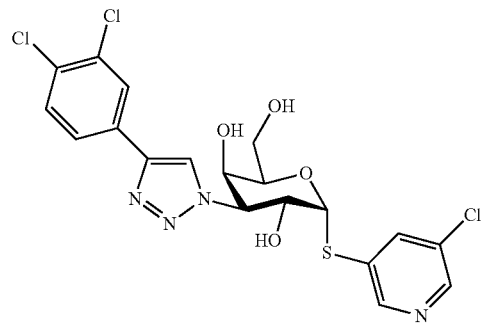

A solution of 5-Chloro-3-pyridyl 2,4,6-tri-O-acetyl-3-deoxy-3-[4-(3,4-dichlorophenyl)-1H-1,2,3-triazol-1-yl]-1-thio-α-D-galactopyranoside (50 mg, 0.08 mmol) in MeOH/Et₃N/H₂O (5/3/1) (1.8 mL) was stirred at room temperature for 20 h. The mixture was evaporated to dryness and the residue was purified by preparative HPLC to afford the title compound as a white solid (33 mg, 82.5%).

m/z calcd for [C₂₅H₂₃Cl₃N₄O₇S]⁻ [M+H]⁺: 503.0; found: 503.0.

¹H NMR (400 MHz, DMSO) δ 8.83 (s, 1H), 8.64 (d, J=1.8 Hz, 1H), 8.54 (d, J=2.2 Hz, 1H), 8.19 (t, J=2.1 Hz, 1H), 8.16 (d, J=1.9 Hz, 1H), 7.91 (dd, J=8.4, 2.0 Hz, 1H), 7.73 (d, 0.1=8.4 Hz, 1H), 6.00 (d, J=4.9 Hz, 1H), 5.95 (br, 1H), 5.56 (br, 1H), 4.85 (dd, J=11.3, 2.4 Hz, 1H), 4.79 (dd, J=11.3, 5.0 Hz, 1H), 4.77 (br, 1H), 4.26 (t, J=6.1 Hz, 1H), 4.03 (s, 1H), 3.47 (ddd, J=17.8, 10.9, 6.2 Hz, 2H).

Example 22

3,4-Dichlorophenyl 3-deoxy-3-[4-(5-chloro-3-pyridyl)-1H-1,2,3-triazol-1-yl]-1-thio-α-D-galactopyranoside

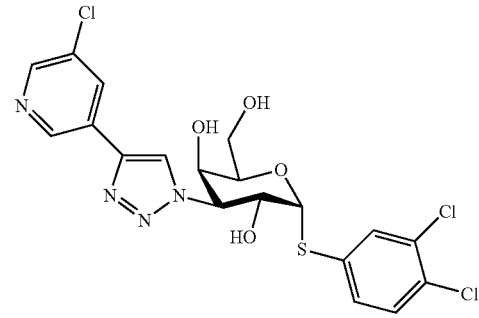

A solution of 3,4-Dichlorophenyl 2,4,6-tri-O-acetyl-3-deoxy-3-[4-(5-chloro-3-pyridyl)-1H-1,2,3-triazol-1-yl]-1-thio-α-D-galactopyranoside (50.0 mg, 0.08 mmol) was dissolved in water (1 mL), methanol (2 mL), TEA (0.5 mL). The mixture was stirred at rt for 5 h. Then the mixture was concentrated and purified by preparative TLC eluted with DCM/MeOH (15/1) to give the title compound. 25.0 mg (62.5%). 1H NMR (400 MHz, MeOD) δ 9.01 (d, J=1.8 Hz, 1H), 8.70 (s, 1H), 8.55 (d, J=2.3 Hz, 1H), 8.38 (t, J=2.1 Hz, 1H), 7.82 (d, J=2.0 Hz, 1H), 7.56 (dd, J=8.4, 2.1 Hz, 1H), 7.50 (d, J=8.4 Hz, 1H), 5.88 (d, J=5.2 Hz, 1H), 5.04 (dd, J=11.4, 2.8 Hz, 1H), 4.96 (dd, J=11.4, 5.2 Hz, 1H), 4.52 (t, J=6.2 Hz, 1H), 4.23 (d, J=1.8 Hz, 1H), 3.74 (qd, J=11.4, 6.1 Hz, 2H).

m/z calcd for $[C_{19}H_{16}Cl3FN4O4S]^+$ $[M+H]^+$: 503, 505; found: 503, 505.

Intermediates i1-i20 i1) 4-Bromo-5-cyano-2-pyridyl 2,4,6-tri-O-acetyl-3-deoxy-3-[4-(3,4,5-trifluorophenyl)-1H-1,2,3-triazol-1-yl]-1-thio-α-D-galactopyranoside 2,4,6-tri-O-acetyl-3-azido-1-chloro-3-deoxy-β-D-galactopyranoside

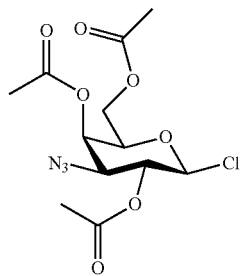

To a stirred suspension of 1,2,4,6-tetra-O-acetyl-3-azido-3-deoxy-β-D-galactopyranoside (5.0 g, 13.39 mmol), Phosphorus pentachloride (3.07 g, 14.7 mmol) in dry methylene chloride (50 mL), boron trifluoride dimethyl etherate (76.3 mg, 0.67 mmol) was added. After stirring for 30 min, the reaction mixture was diluted with DCM (120 mL×2) and then washed with ice-cold water (60 mL×3), saturated ice-cold NaHCO₃ solution (2×50 mL), and again icecold water (30 mL×2), dried over anhydrous Na₂SO₄ and evaporated under reduced pressure. The residue was co-evaporated with toluene to give the title compound 4.510 g (96%) as a white solid.

¹H NMR (500 MHz, CDCl₃) δ 5.48 (d, J=2.5 Hz, 1H), 5.38-5.28 (m, 1H), 5.24 (d, J=8.7 Hz, 1H), 4.18 (dd, J=11.6, 6.0 Hz, 1H), 4.10 (dd, J=11.6, 6.8 Hz, 1H), 4.02-3.94 (m, 1H), 3.61 (dd, J=10.3, 3.3 Hz, 1H), 2.20 (s, 3H), 2.17 (s, 3H), 2.08 (s, 3H).

Acetyl 2,4,6-tri-O-acetyl-3-azido-3-deoxy-1-thio-α-D-galactopyranoside

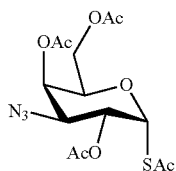

To a solution of 2,4,6-tri-O-acetyl-3-azido-1-chloro-3-deoxy-β-D-galactopyranoside (1.6 g, 4.58 mmol) in DMF (20 mL) was added CH₃COSK (1.05 g, 9.16 mmol) at room temperature for 20 h. Water (50 mL) and DCM (50 mL) were added. The aqueous phase was extracted with DCM (50 mL×2), the combined organic phase was washed with water (100 mL) and brine (100 mL), dried over anhydrous sodium sulphate. Removal of solvent gave a residue which was purified by column chromatography (PE/EA=3/1) to obtain the desired product (900 mg, 50%).

m/z calcd for $[C_{14}H_{19}N_3O_8S]^-$ $[M+H]^+$: 390.0; found: 390.0.

4-Bromo-5-cyano-2-pyridyl 2,4,6-tri-O-acetyl-3-azido-3-deoxy-1-thio-α-D-galactopyranoside

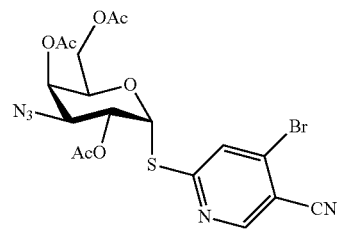

To a solution of acetyl 2,4,6-tri-O-acetyl-3-azido-3-deoxy-1-thio-α-D-galactopyranoside (97 mg, 0.25 mmol) in DCM (5 mL) were added 4,6-dibromonicotinonitrile (130 mg, 0.5 mmol), Diethylamine (0.5 mL). The reaction was stirred at room temperature for 20 h. Water (50 mL) and DCM (50 mL) were added. The aqueous phase was extracted with DCM (50 mL×2), the combined organic phases were washed with water (100 mL) and brine (100 mL), dried over anhydrous sodium sulphate. Removal of solvent gave a residue which was purified by column chromatography (PE/EA=3/1) to obtain the desired product. (45 mg, 34%)

m/z calcd for $[C_{18}H_{18}BrN_5O_7S]^-$ $[M+H]^+$: 528.0; found: 528.0.

¹H NMR (400 MHz, CDCl₃) δ 8.50 (s, 1H), 7.78 (s, 1H), 6.35 (d, J=5.5 Hz, 1H), 5.50 (d, J=2.8 Hz, 1H), 5.36 (dd, J=11.0, 5.5 Hz, 1H), 4.44 (dd, J=7.6, 4.8 Hz, 1H), 4.18-4.09 (m, 2H), 4.01 (dd, J=11.1, 3.3 Hz, 1H), 2.20 (s, 3H), 2.19 (s, 3H), 1.96 (s, 3H). 4-Bromo-5-cyano-2-pyridyl 2,4,6-tri-O-acetyl-3-deoxy-3-[4-(3,4,5-trifluorophenyl)-1H-1,2,3-triazol-1-yl]-1-thio-α-D-galactopyranoside

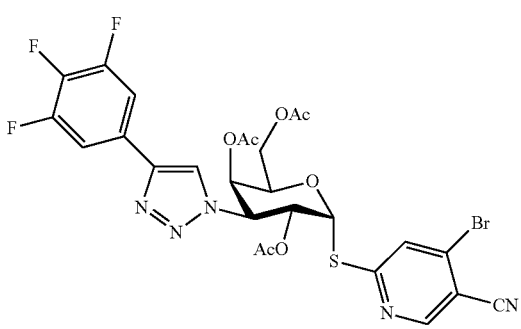

To a solution of 4-bromo-5-cyano-2-pyridyl 2,4,6-tri-O-acetyl-3-azido-3-deoxy-1-thio-α-D-galactopyranoside (45 mg, 0.08 mmol) in DMF (3 mL) were added TEA (0.07 mL), Copper(I)Iodide (5 mg, 0.03 mmol), CsF (20 mg, 0.13 mmol), 3,4,5-trifluorophenylacetylene (30 mg, 0.13 mmol). The reaction was stirred at room temperature for 20 h under a nitrogen atmosphere. Water (10 mL) and DCM (10 mL) were added. The aqueous phase was extracted with DCM (5 mL×2), the combined organic phases were washed with water (20 mL) and brine (20 mL), dried over anhydrous sodium sulphate. Removal of solvent gave a residue. which was purified by column chromatography (PE/EA=2/1) to obtain the desired product (40 mg, 43%).

m/z calcd for $[C_{26}H_{21}BrF_3N_5O_7S]^-$ $[M+H]^+$: 684.0; found: 684.0.

i2) 4-Chloro-5-cyano-2-pyridyl 2,4,6-tri-O-acetyl-3-deoxy-3-[4-(3,4,5-trifluorophenyl)-1H-1,2,3-triazol-1-yl]-1-thio-α-D-galactopyranoside 4-Chloro-5-cyano-2-pyridyl 2,4,6-tri-O-acetyl-3-azido-3-deoxy-1-thio-α-D-galactopyranoside

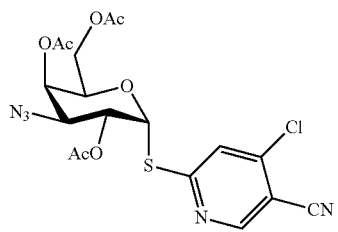

Acetyl 2,4,6-tri-O-acetyl-3-azido-3-deoxy-1-thio-α-D-galactopyranoside (400 mg, 1.03 mmol) and 4,6-dichloropyridine-3-carbonitrile (266.58 mg, 1.54 mmol) were dissolved in DMF (2 mL) and TEA (1 mL). Diethylamine (112.7 mg, 1.54 mmol) was added at 0° C. The mixture was stirred at 0° C. for 1 hour. EtOAc (100 mL) was added. The mixture was washed by 1 M NaHSO$_4$ (50 mL), brine (50 mL), dried over Na$_2$SO$_4$, filtered and concentrated. The residue was purified on silica gel column using a gradient of EA/PE form 0-25% to give the title compound 200 mg (40%).

ESI-MS m/z calcd for $[C_{18}H_{19}ClN_5O_7S]^+$ (M+H)+: 484.1; found: 484.1.

4-Chloro-5-cyano-2-pyridyl 2,4,6-tri-O-acetyl-3-deoxy-3-[4-(3,4,5-trifluorophenyl)-1H-1,2,3-triazol-1-yl]-1-thio-α-D-galactopyranoside

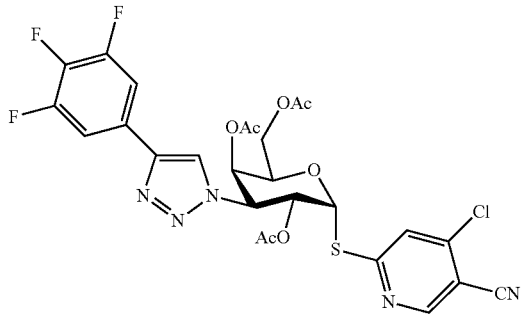

4-Chloro-5-cyano-2-pyridyl 2,4,6-tri-O-acetyl-3-azido-3-deoxy-1-thio-α-D-galactopyranoside (260 mg, 0.54 mmol), TEA (54 mg, 0.54 mmol) and trimethyl-[2-(3,4,5-trifluorophenyl)ethynyl]silane (184 mg, 0.81 mmol) were dissolved in CH$_3$CN (5 mL). CuI (30.7 mg, 0.16 mmol) and CsF (81.6 mg, 0.54 mmol) were added. The mixture was stirred at rt for 4 hours. Then the mixture was concentrated and the residue was purified on silica gel column using a gradient of EA/PE from 0-40% to give the title compound 60 mg (17%).

ESI-MS m/z calcd for $[C_{26}H_{22}ClF_3N_5O_7S]^+$ $(M+H)^+$: 640.1; found: 640.1.

i3) 2-Chloro-4-pyridyl 2,4,6-tri-O-acetyl-3-deoxy-3-[4-(3,4,5-trifluorophenyl)-1H-1,2,3-triazol-1-yl]-1-thio-α-D-galactopyranoside 2-Chloro-4-pyridyl 2,4,6-tri-O-acetyl-3-azido-3-deoxy-1-thio-α-D-galactopyranoside

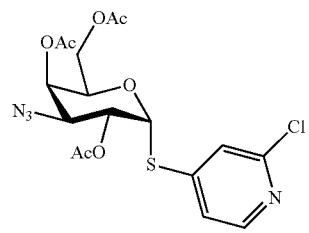

To a solution of acetyl 2,4,6-tri-O-acetyl-3-azido-3-deoxy-1-thio-α-D-galactopyranoside (100 mg, 0.25 mmol) in DCM (5 mL) were added 2-chloro-4-fluoropyridine (50 mg, 0.38 mmol), Diethylamine (0.5 mL). The reaction was stirred at at room temperature with stirring for 20 h.

Water (50 mL) and DCM (50 mL) were added. The aqueous phase was extracted with DCM (50 mL×2), the combined organic phases were washed with water (100 mL) and brine (100 mL), dried over anhydrous sodium sulphate. Removal of solvent gave a residue. The residue was purified by column chromatography (PE/EA=3/1) to obtain the product (50 mg).

m/z calcd for [C17H19ClN$_4$O$_7$S]$^+$[M+H]$^+$: 459.0; found: 459.0.

2-Chloro-4-pyridyl 2,4,6-tri-O-acetyl-3-deoxy-3-[4-(3,4,5-trifluorophenyl)-1H-1,2,3-triazol-1-yl]-1-thio-α-D-galactopyranoside

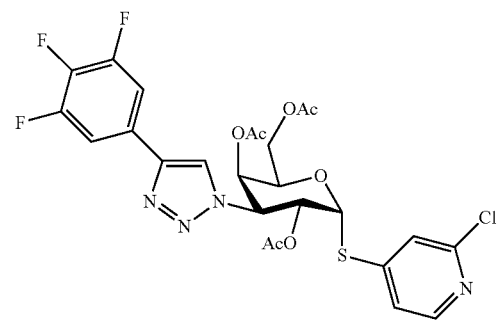

To a mixture of 2-Chloro-4-pyridyl 2,4,6-tri-O-acetyl-3-azido-3-deoxy-1-thio-α-D-galactopyranoside (50 mg, 0.11 mmol) in DMF (5 mL) were added TEA (0.2 mL), Copper (I)Iodide (6 mg, 0.03 mmol), CsF (25 mg, 0.16 mmol), trimethyl-[2-(3,4,5-trifluorophenyl)ethynyl]silane (37 mg, 0.16 mmol). The reaction was stirred at room temperature for 20 h under a N$_2$ atmosphere. Water (10 mL) and DCM (10 mL) were added. The aqueous phase was extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=2/1) to obtain the product (45 mg)

m/z calcd for $[C_{25}H_{22}ClF_3N_4O_7S]^+$ $[M+H]^+$: 615.0; found: 615.0.

$^1$H NMR (400 MHz, CDCl$_3$) δ 8.21 (d, J=5.3 Hz, 1H), 7.71 (s, 1H), 7.37 (t, J=7.1 Hz, 3H), 7.21 (d, J=1.6 Hz, 1H), 6.36 (d, J=5.5 Hz, 1H), 6.09 (dd, J=11.8, 5.6 Hz, 1H), 5.54 (d, J=2.3 Hz, 1H), 5.13 (dd, J=11.7, 3.0 Hz, 1H), 4.71-4.62 (m, 1H), 4.06 (ddd, J=19.2, 11.6, 6.4 Hz, 2H), 2.02 (s, 3H), 1.89 (s, 3H), 1.86 (s, 3H).

i4) 5-Chloro-2-cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside and i5) 5-Bromo-6-cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside 5-Chloro-2-cyano-3-pyridyl 2,4,6-tri-O-acetyl-3-azido-3-deoxy-1-thio-α-D-galactopyranoside and 5-Bromo-6-cyano-3-pyridyl 3-deoxy-3-[4-(3,4,5-trifluorophenyl)-1H-1,2,3-triazol-1-yl]-1-thio-α-D-galactopyranoside

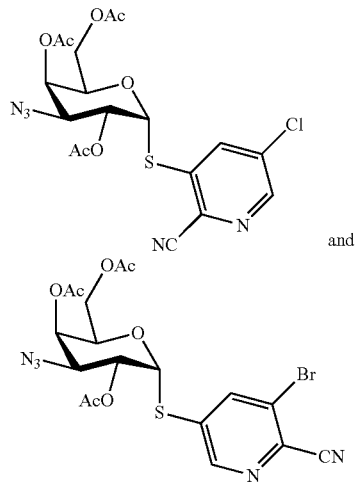

To a solution of acetyl 2,4,6-tri-O-acetyl-3-azido-3-deoxy-1-thio-α-D-galactopyranoside (100 mg, 0.25 mmol) in DCM (5 mL) were added 3-bromo-5-chloropicolinonitrile (80 mg, 0.38 mmol), Diethylamine (0.5 mL). The reaction was stirred at room temperature with for 20 h. Water (50 mL) and DCM (50 mL) were added. The aqueous phase was extracted with DCM (50 mL×2), the combined organic phases were washed with water (100 mL) and brine (100 mL), dried over anhydrous sodium sulphate. Removal of solvent gave a residue. The residue was purified by column chromatography (PE/EA=3/1) to obtain the title products as a mixture (50 mg).

5-Chloro-2-cyano-3-pyridyl 2,4,6-tri-O-acetyl-3-azido-3-deoxy-1-thio-α-D-galactopyranoside m/z calcd for $[C_{18}H_{18}ClN_5O_7S]^-$ $[M+H]^+$: 484.0; found: 484.0.

5-Bromo-6-cyano-3-pyridyl 3-deoxy-3-[4-(3,4,5-trifluorophenyl)-1H-1,2,3-triazol-1-yl]-1-thio-α-D-galactopyranoside m/z calcd for $[C_{18}H_{18}BrN_5O_7S]^-$ $[M+H]^+$: 528.0; found: 528.0.

5-Chloro-2-cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside (i4)

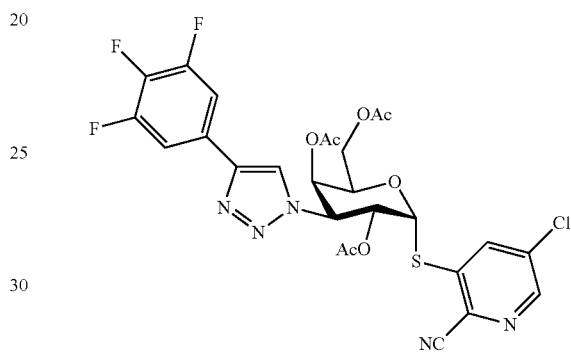

and

5-Bromo-6-cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside (i5)

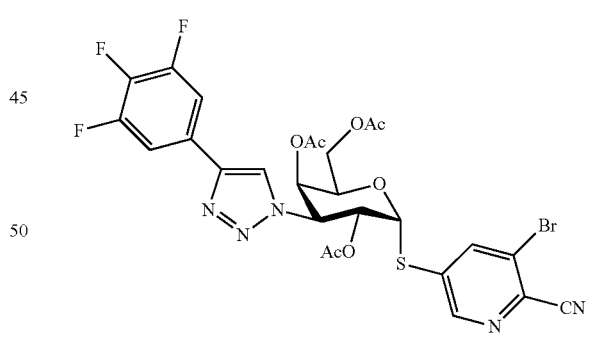

To a mixture of 5-Chloro-2-cyano-3-pyridyl 2,4,6-tri-O-acetyl-3-azido-3-deoxy-1-thio-α-D-galactopyranoside and 5-Bromo-6-cyano-3-pyridyl 3-deoxy-3-[4-(3,4,5-trifluorophenyl)-1H-1,2,3-triazol-1-yl]-1-thio-α-D-galactopyranoside (50 mg) in DMF (5 mL) were added TEA (0.2 mL), Copper(I)Iodide (27 mg, 0.14 mmol), CsF (110 g, 0.70 mmol), trimethyl-[2-(3,4,5-trifluorophenyl)ethynyl]silane (160 mg, 0.07 mmol). The reaction was stirred at room temperature for 20 h under under a N$_2$ atmosphere. Water (10 mL) and DCM (10 mL) were added. The aqueous phase was extracted with DCM (5 mL×2), the combined organic phase was washed with water (20 mL) and brine (20 mL), dried over anhydrous sodium sulphate. Removal of solvent gave a residue. The residue was purified by column chromatography (PE/EA=2/1) to obtain the i4 (10 mg) and i5 (20 mg).

i4) 5-Chloro-2-cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside m/z calcd for $[C_{26}H_{21}ClF_3N_5O_7S]^+$ [M+H]$^+$: 640.0; found: 640.0.
$^1$H NMR (400 MHz, CDCl$_3$) δ 8.58 (d, J=2.1 Hz, 1H), 8.07 (d, J=2.1 Hz, 1H), 7.85 (s, 1H), 7.44 (dd, J=7.8, 6.6 Hz, 2H), 6.29 (d, J=5.5 Hz, 1H), 6.16 (dd, J=11.6, 5.6 Hz, 1H), 5.65 (d, J=2.3 Hz, 1H), 5.22 (dd, J=11.6, 3.0 Hz, 1H), 4.88-4.77 (m, 1H), 4.22-4.03 (m, 2H), 2.06 (s, 3H), 2.01 (s, 3H), 2.00 (s, 3H).

i5) 5-Bromo-6-cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside m/z calcd for $[C_{26}H_{21}BrF_3N_5O_7S]^-$ [M+H]$^+$: 684.0; found: 684.0.
$^1$H NMR (400 MHz, CDCl$_3$) δ 8.67 (d, J=1.9 Hz, 1H), 8.16 (d, J=1.9 Hz, 1H), 7.78 (s, 1H), 7.50-7.38 (m, 2H), 6.34 (d, J=5.5 Hz, 1H), 6.16 (dd, J=11.7, 5.5 Hz, 1H), 5.62 (d, J=2.8 Hz, 1H), 4.83-4.64 (m, 1H), 4.24-3.98 (m, 2H), 2.09 (s, 3H), 2.01 (s, 3H), 1.98 (s, 3H).

i6) 5-Bromo-2-Cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside 5-Bromo-2-Cyano-3-pyridyl 2,4,6-tri-O-acetyl-3-azido-3-deoxy-1-thio-α-D-galactopyranoside and 5-Chloro-6-cyano-3-pyridyl 2,4,6-tri-O-acetyl-3-azido-3-deoxy-1-thio-α-D-galactopyranoside

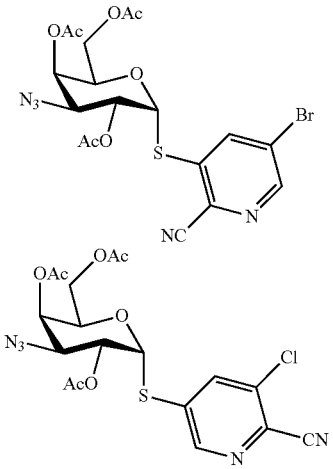

To a solution of acetyl 2,4,6-tri-O-acetyl-3-azido-3-deoxy-1-thio-α-D-galactopyranoside (100 mg, 0.25 mmol) in DCM (5 mL) were added 3-bromo-5-chloropicolinonitrile (80 mg, 0.38 mmol), Diethylamine (0.5 mL). The reaction was stirred at room temperature for 20 h. Water (50 mL) and DCM (50 mL) were added. The aqueous phase was extracted with DCM (50 mL×2), the combined organic phases were washed with water (100 mL) and brine (100 mL), dried over anhydrous sodium sulphate. Removal of solvent gave a residue. The residue was purified by column chromatography (PE/EA=3/1) to obtain a crude product mixture. (45 mg).

5-Bromo-2-Cyano-3-pyridyl 2,4,6-tri-O-acetyl-3-azido-3-deoxy-1-thio-α-D-galactopyranoside m/z calcd for $[C_{18}H_{18}BrN_5O_7S]^-$ [M+H]$^+$: 528.0; found: 528.0.

5-Chloro-6-cyano-3-pyridyl 2,4,6-tri-O-acetyl-3-azido-3-deoxy-1-thio-α-D-galactopyranoside m/z calcd for $[C_{18}H_{18}ClN_5O_7S]^-$ [M+H]$^+$: 484.0; found: 484.0.

i6) 5-Bromo-2-Cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside and 5-Chloro-6-cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside

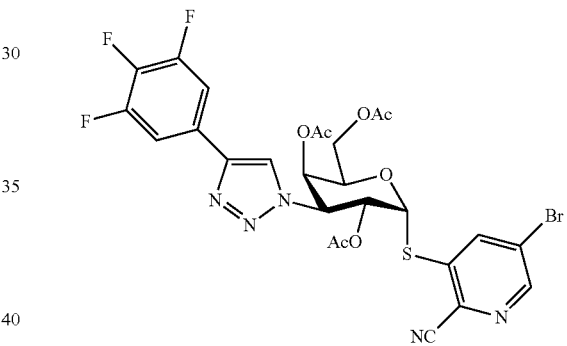

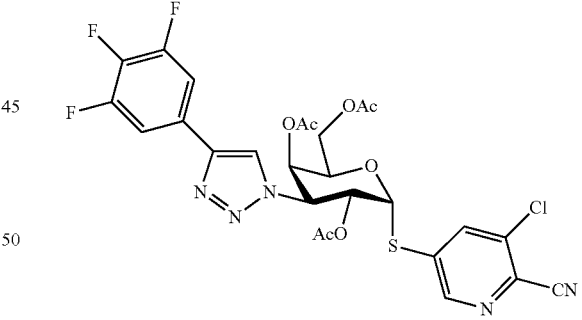

To a mixture of 5-bromo-2-Cyano-3-pyridyl 2,4,6-tri-O-acetyl-3-azido-3-deoxy-1-thio-α-D-galactopyranoside and 5-chloro-6-cyano-3-pyridyl 2,4,6-tri-O-acetyl-3-azido-3-deoxy-1-thio-α-D-galactopyranoside (45 mg) in DMF (5 mL) were added TEA (0.2 mL), Copper(I)Iodide (27 mg, 0.14 mmol), CsF (110 g, 0.70 mmol), trimethyl-[2-(3,4,5-trifluorophenyl)ethynyl]silane(160 mg, 0.07 mmol). The reaction was stirred at room temperature for 20 h under N$_2$. Water (10 mL) and DCM (10 mL) were added. The aqueous phase was extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=2/1) to obtain the title products i6 (10 mg) and 5-Chloro-6-cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside (18 mg).

i6) 5-Bromo-2-Cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside m/z calcd for $[C_{26}H_{21}BrF_3N_5O_7S]^-$ $[M+H]^+$: 684.0; found: 684.0.
$^1$H NMR (400 MHz, CDCl$_3$) δ 8.63 (d, J=1.8 Hz, 1H), 8.16 (d, J=1.8 Hz, 1H), 7.79 (s, 1H), 7.43-7.34 (m, 2H), 6.24 (d, J=5.5 Hz, 1H), 6.11 (dd, J=11.6, 5.5 Hz, 1H), 5.58 (d, J=2.1 Hz, 1H), 5.14 (dd, J=11.6, 2.8 Hz, 1H), 4.80-4.73 (m, 1H), 4.15-3.97 (m, 10H), 2.00 (s, 3H), 1.95 (s, 6H).

5-Chloro-6-cyano-3-pyridyl 2,4,6-tri-O-acetyl-3-deoxy-3-[4-(3,4,5-trifluorophenyl)-1H-1,2,3-triazol-1-yl]-1-thio-α-D-galactopyranoside m/z calcd for $[C_{26}H_{21}ClF_3N_5O_7S]^+[M+H]^+$: 640.0; found: 640.0.
$^1$H NMR (400 MHz, CDCl$_3$) δ 8.63 (d, J=1.9 Hz, 1H), 8.01 (d, J=1.9 Hz, 1H), 7.79 (s, 1H), 7.48-7.39 (m, 2H), 6.34 (d, J=5.5 Hz, 1H), 6.16 (dd, J=11.6, 5.6 Hz, 1H), 5.62 (d, J=2.3 Hz, 1H), 5.20 (dd, J=11.7, 3.0 Hz, 1H), 4.78-4.71 (m, 1H), 4.21-4.04 (m, 2H), 2.09 (s, 3H), 2.00 (s, 3H), 1.98 (s, 3H).

i7) 4-Chloro-2-pyridyl 2,4,6-tri-O-acetyl-3-deoxy-3-[4-(3,4,5-trifluorophenyl)-1H-1,2,3-triazol-1-yl]-1-thio-α-D-galactopyranoside O-4-chloropyridin-2-yl dimethylcarbamothioate

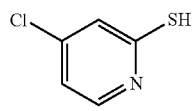

A solution of 4-chloropyridin-2-ol (1 g, 10 mmol) and 1,4-diazabicyclooctane (1.8 g, 16.02 mmol) in tetrahydrofuran (30 ml) was added N,N-dimethylcarbamothioyl chloride (1.3 g, 10.68 mmol). The reaction mixture was stirred at r.t over 16 h The reaction mixture was evaporated to dryness and the residue was purified by flash chromatography (PE:EA=10%-50%) to give the title compound 800 mg (54.6%).
m/z calcd for $[C_8H_9ClN_2OS]^+$ $[M+H]^+$: 217.0; found: 217.0.

S-[(5-chloro-3-pyridyl)] N,N-dimethylcarbamothioate

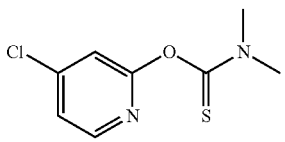

O-[(5-chloro-3-pyridyl)] N,N-dimethylcarbamothioate (600 mg, 2.8 mmol) was taken up to in phenoxybenzene (10 mL) and was added to 5 mL of refluxing phenoxybenzene. After 2 h the reaction mixture was cooled and filtered through 100 g SiO$_2$ to remove the phenoxybenzene, subsequent elution with PE:EA=1:2 to give product 450 mg (72.6%) as yellow solid.
m/z calcd for $[C_8H_9ClN_2OS]^+[M+H]^+$: 217.0; found: 217.0.

4-chloropyridine-2-thiol

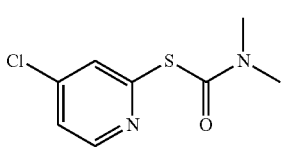

A solution of S-4-chloropyridin-2-yl dimethylcarbamothioate (450 mg, 1.8 mmol) and NaOH (300 mg, 7.5 mmol) in 20 mL ethanol/water=3:1, heated at 50° C. for 2 h. The mixture was concentrated to about 100 ml, EtOAc (50 mL) was added and the pH was adjusted to pH 6 with 2 M hydrochloric acid. The organic layer was dried over Na$_2$SO$_4$, concentrated and the residue was purified by flash chromatography (EA:PE=1:5 to 1:2, ISCO®, 20 g, 30 ml/min, normal phase silica, uv254) to give product 100 mg (45%) as yellow oil.
m/z calcd for $[C_5H_4ClNS]^-$ $[M-H]^-$: 144.0; found: 144.0.

4-Chloro-2-pyridyl 2,4,6-tri-O-acetyl-3-azido-3-deoxy-1-thio-α-D-galactopyranoside

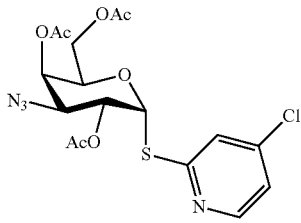

Cs$_2$CO$_3$ (420 mg, 1.3 mmol) was suspended in DMF (5 mL) followed by addition of 4-chloropyridine-2-thiol (100 mg, 0.68 mmol). After 30 min, 2,4,6-tri-O-acetyl-3-azido-1-chloro-3-deoxy-β-D-galactopyranoside (200 mg, 0.6 mmol) was added. The mixture was stirred at r.t for 16 h. The mixture was diluted with DCM (50 mL), 0.5 M citric acid (50 mL) and water (50 mL). The organic phase was washed with water (50 mL) and concentrated. The residue was purified by column chromatography (PE:EA=3:1) to give product 30 mg (13%) as a white solid.
m/z calcd for $[C_{17}H_{19}ClN_4O_7S]^+[M+H]^+$: 459.0; found: 459.0.

4-Chloro-2-pyridyl 2,4,6-tri-O-acetyl-3-deoxy-3-[4-(3,4,5-trifluorophenyl)-1H-1,2,3-triazol-1-yl]-1-thio-α-D-galactopyranoside

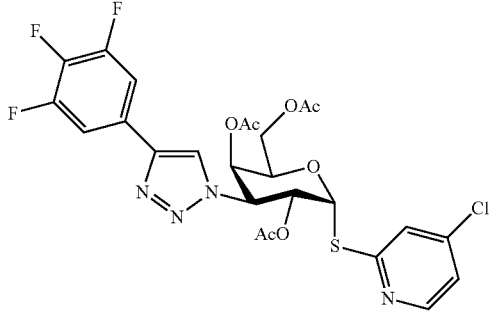

To a solution of 4-chloro-2-pyridyl 2,4,6-tri-O-acetyl-3-azido-3-deoxy-1-thio-α-D-galactopyranoside (30 mg, 0.06 mmol) in MeCN (2 mL) was added trimethyl-[2-(3,4,5-trifluorophenyl)ethynyl]silane (50 mg, 0.11 mmol), CsF (10 mg, 0.08 mmol), iodocopper (7 mg, 0.01 mmol). The reaction vessel was purged 3 times with nitrogen. The mixture was stirred at r.t for 16 h. The reaction was quenched with water (10 mL). The mixture was extracted with dichloromethane (10 mL×3) and the combined organic phases were washed with brine (10 mL) and dried over Na$_2$SO$_4$, filtered, and concentrated to dryness in vacuo. The crude product was purified by flash chromatography (EA:PE=1:10 to 1:2, ISCO® 12 g, 20 ml/min, normal phase silica, uv254) to give the title compound 25 mg (42%) as a yellow solid.

m/z calcd for [C$_{25}$H$_{22}$ClF$_3$N$_4$O$_7$S]$^+$[M+H]$^+$: 615.0; found: 615.0.

i8) 5-Bromo-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside O-[(5-bromo-3-pyridyl)] N,N-dimethylcarbamothioate

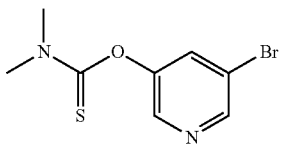

To a solution of 5-bromopyridin-3-ol (17.4 g, 0.10 mol) in DMF (0.15 L) was added sodium hydride (2.64 g, 0.11 mol, 96% in mineral oil) at 0° C., followed by stirring at 0° C. for 30 min. Dimethylthiocarbamoyl chloride (14.83 g, 0.12 mol) was added to the reaction mixture followed by stirring at room temperature over night. LC-MS analysis indicated formation of the target compound. The reaction mixture was quenched with water (100 mL) followed by extraction with EtOAc (100 mL×3). The combined organic layers were washed with brine (100 mL), dried over Na$_2$SO$_4$ and concentrated in vacuo. The crude product was purified by flash chromatography (EtOAc/PE=5%-40%, ISCO® 120 g, 50 mL/min, normal phase silica gel, uv254) to afford the target compound (9.93 g, 36.5% yield) as yellow oil.

ESI-MS m/z calcd for [C$_8$H$_9$BrN$_2$OS]$^+$[M+H]$^+$: 261.0; found: 261.0

S-[(5-bromo-3-pyridyl)] N,N-dimethylcarbamothioate

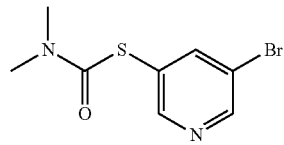

O-[(5-bromo-3-pyridyl)] N,N-dimethylcarbamothioate (9.93 g, 0.04 mol) was dissolved in phenoxybenzene (100 mL). The mixture was heated at reflux for 2 h. The reaction mixture was cooled to room temperature and directly purified by flash chromatography on a Biotage (EtOAc/PE=5%-50%, ISCO 120 g, 50 mL/min, normal phase silica gel, uv 254) to afford the target compound S-[(5-bromo-3-pyridyl)] N,N-dimethylcarbamothioate (4.63 g, 43.8% yield) as a yellow solid.

ESI-MS m/z calcd for [C$_8$H$_9$BrN$_2$OS]$^+$ [M+H]$^+$: 261.0; found: 261.0

3-bromo-5-methoxy-benzenethiol

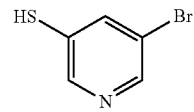

S-(3-chloro-5-methoxy-phenyl) N,N-dimethylcarbamothioate (1.044 g, 4 mmol) and KOH (897.21 mg, 16 mmol) was taken up in in ethanol/water (40 mL, 3/1). The reaction mixture was heated at reflux for 2 h. LC-MS analysis indicated total consumption of the starting material. The mixture was concentrated followed by addition of 10% aq NaOH (30 mL). The reaction mixture was washed with ether (15 mL×3). The aqueous layer was acidified with aq KHSO$_4$ to adjust the pH ~2, followed by extraction with EtOAc (20 mL×5). The combined organic layers were washed with brine, dried over Na$_2$SO$_4$ and concentrated in vacuo to afford crude product, which was used for next step directly without further purification.

ESI-MS m/z calcd for [C$_8$H$_4$BrNS]$^-$ [M-H]$^-$: 188.9; found: 188.0.

5-Bromopyridin-3-yl 2,4,6-tri-O-acetyl-3-azido-3-deoxy-1-thio-α-D-galactopyranoside

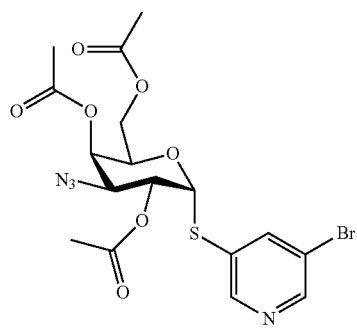

NaH (82.99 mg, 3.47 mmol) was added to a solution of 5-bromopyridine-3-thiol (658.67 mg, 3.47 mmol) in DMF (10 mL) at 0° C. The solution was stirred at rt for 30 min. Then 2,4,6-tri-O-acetyl-3-azido-1-chloro-3-deoxy-β-D-galactopyranoside (1.01 g, 2.89 mmol) was added. The reaction mixture was stirred at 50° C. for 2 h followed by cooling to room temperature. Water (50 mL) was added and the reaction mixture was extracted with EtOAc (15 mL×3). The combined organic layers were washed with brine, dried over Na$_2$SO$_4$ and concentrated in vacuo to afford crude product, which was purified by biotage (EtOAc/PE=5-40%, ISCO® 40 g, 30 mL/min, normal phase silica gel, uv 254) to afford the title compound (650 mg, 44.7% yield) as a white solid.

ESI-MS m/z calcd for [C$_{17}$H$_{19}$BrN$_4$O$_7$S]$^+$[M+H]$^+$: 503.0; found: 503.0

5-Bromo-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside

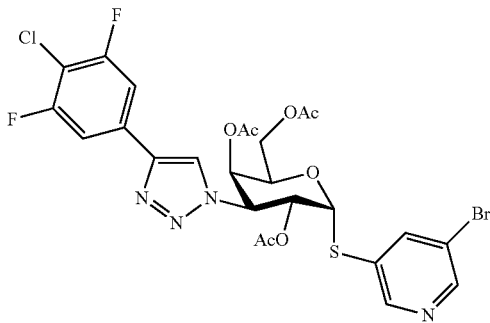

To a solution of 5-bromo-3-pyridyl 2,4,6-tri-O-acetyl-3-azido-3-deoxy-1-thio-α-D-galactopyranoside (50 mg, 0.10 mmol) in DMF (3 mL) were added TEA (0.10 mL), Copper (I)Iodide (6 mg, 0.03 mmol), CsF (23 mg, 0.15 mmol), ((4-chloro-3,5-difluorophenyl)ethynyl)trimethylsilane (37 mg, 0.15 mmol). The reaction was stirred at room temperature with for 20 h under N$_2$. Water (10 mL) and DCM (10 mL) were added. The aqueous phase was extracted with DCM (5 mL×2) and the combined organics were washed with water (20 mL) and brine (20 mL), dried over anhydrous sodium sulphate. Removal of solvent gave a residue. The residue was purified by column chromatography (PE/EA=2/1) to obtain the desired product (40 mg, 59%).

ESI-MS m/z calcd for [C$_{25}$H$_{22}$BrClF$_2$N$_4$O$_7$S]$^+$[M+H]$^+$: 675.0; found: 675.0 i9) 5-Chloro-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside ((4-chloro-3,5-difluorophenyl)ethynyl)trimethylsilane

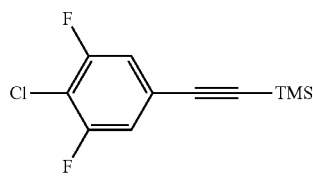

To a solution of 5-bromo-2-chloro-1,3-difluorobenzene (1 g, 4.42 mmol) in CH$_3$CN (20 mL) was added CuI (348 mg, 1.33 mmol), DIPEA (3.6 mL), Pd(PPh$_3$)$_2$Cl$_2$ (308 mg, 0.44 mmol). The mixture was heated under N$_2$ at 50° C. for 20 h. Removal of solvent gave a residue which was purified by column chromatography (PE/EA=10/1) to obtain product (400 mg, 37%).

ESI-MS m/z calcd for [C$_{11}$H$_{11}$ClF$_2$Si]$^+$[M+H]$^+$: 245.0; found: 245.0 i43) 5-Chloropyridin-3-yl 2,4,6-tri-O-acetyl-3-deoxy-3-[4-(3,4,5-trifluorophenyl)-1H-1,2,3-triazol-1-yl]-1-thio-α-D-galactopyranoside O-[(5-chloro-3-pyridyl)] N,N-dimethylcarbamothioate

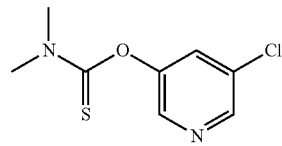

To a solution of 5-chloropyridin-3-ol (10 g, 0.10 mol) in N,N-dimethylformamide (200 mL) was added NaH (1.90 g, 0.10 mol) at 0° C. The reaction mixture was stirred at 0° C. 30 minutes followed by addition of Dimethylthiocarbamoyl chloride (10.50 g, 0. 10 mol) followed by stirring at room temperature 20 h. The reaction was quenched with water (500 mL) and extracted with dichloromethane (500 mL×3). The combined organics were washed with brine (400 mL×3), dried over Na$_2$SO$_4$, filtered and the solvents where removed in vacuo. The crude product was purified by chromatography on a combiflash (EtOAc:PE=1:5) to give the title compound 6.2 g (28.7%) as brown oil.

m/z calcd for [C$_8$H$_9$ClN$_2$OS]$^+$[M+H]$^+$: 217.0; found: 217.0.

S-[(5-chloro-3-pyridyl)] N,N-dimethylcarbamothioate

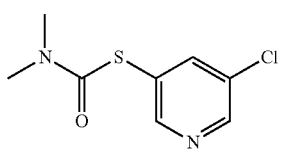

O-[(5-chloro-3-pyridyl)] N,N-dimethylcarbamothioate (6.2 g, 28.7 mmol) was taken up to in phenoxybenzene (30 mL) and added to 5 mL of refluxing phenoxybenzene. After 2 h, the reaction mixture was cooled and passed through 200 g SiO$_2$ to remove the phenoxybenzene, subsequent elution with PE:EtOAc=1:2 gave the title compound 4.5 g (73%) as yellow solid.

m/z calcd for [C$_8$H$_9$ClN$_2$OS]$^+$[M+H]$^+$: 217.0; found: 217.0.

5-chloropyridine-3-thiol

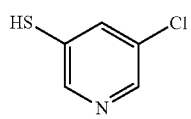

S-[(5-chloro-3-pyridyl)] N,N-dimethylcarbamothioate (3.5 g, 16.20 mmol) and NaOH (3.24 g, 81 mmol) was taken up into 160 mL ethanol/water=3:1 and heated at reflux for 2 h. The reaction mixture was concentrated to about 100 mL. EtOAc (300 mL) was added and the pH was adjusted to about 6 by addition of HCl (2M). The organic layer was isolated and dried over $Na_2SO_4$, concentrated, purified by chromatography on a combiflash (EtOAc:PE=1:5 to 1:2, ISCO, 40 g, 40 ml/min, normal phase silica, uv254) to give 5-chloropyridine-3-thiol 2.0 g (85%) as yellow oil.

m/z calcd for $[C_5H_4ClNS]^-$ $[M-H]^-$: 144.0; found: 144.0.

5-Chloropyridin-3-yl 2,4,6-tri-O-Acetyl-3-azido-3-deoxy-1-thio-α-D-galactopyranoside

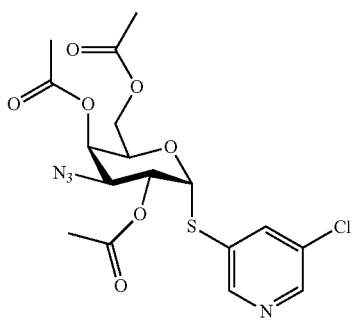

NaH (303.44 mg, 7.58 mmol) was suspended in DMF (25 mL). The 5-chloropyridine-3-thiol (1000 mg, 6.89 mmol) was added. After 30 min, the 3-azido-3-deoxy-2,4,6-tri-O-acetyl-1-chloro-3-D-galactopyranoside (1923.68 mg, 5.51 mmol) was added. The mixture was heated to 50° C. 3 h. The mixture was diluted with DCM (150 mL), 0.5M citric acid (150 mL) and water (150 mL). The organic phase was washed with water (100 mL) and concentrated. The residue was purified by column chromatography (PE:EtOAc=3:1) to give the title compound 900 mg (28.5%) as a white solid.

m/z calcd for $[C_{17}H_{19}ClN_4O_7S]^+$ $[M+H]^+$: 459.0; found: 459.0.

5-Chloro-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside

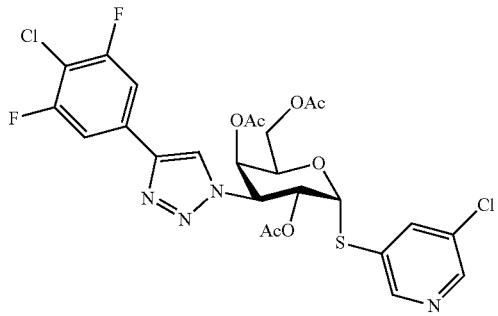

To a solution of 5-Chloro-3-pyridyl 2,4,6-tri-O-acetyl-3-azido-3-deoxy-1-thio-α-D-galactopyranoside (60 mg, 0.13 mmol) in N,N-dimethylformamide (6 mL) was added ((4-chloro-3,5-difluorophenyl)ethynyl)trimethylsilane (63 mg, 0.26 mmol), iodocopper (7 mg, 0.04 mmol). The reaction vessel was purged 3 times with nitrogen. The reaction was quenched with water (10 mL). The mixture was extracted with dichloromethane (10 mL×3) and the combined organics were washed with brine (5 mL) and dried over $Na_2SO_4$, filtered, and concentrated to dryness. The crude product was purified by flash chromatography (EA:PE=1:10 to 1:2, ISCO® 12 g, 20 ml/min, normal phase silica, uv254) to give the title compound 45 mg (56%) as a yellow solid.

m/z calcd for $[C_{25}H_{22}Cl_2F_2N_4O_7S]^+[M+H]^+$: 631.0; found: 631.0.

i10) 5-Chloro-6-cyano-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside and i11) 5-Bromo-2-cyano-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside 5-Chloro-6-cyano-3-pyridyl 2,4,6-tri-O-acetyl-3-azido-3-deoxy-1-thio-α-D-galactopyranoside and 5-Bromo-2-cyano-3-pyridyl 2,4,6-tri-O-acetyl-3-azido-3-deoxy-1-thio-α-D-galactopyranoside

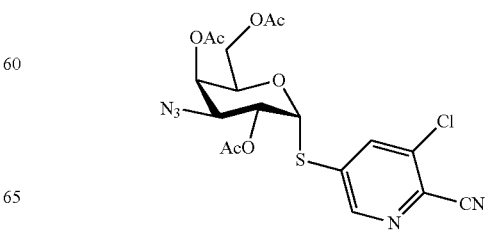

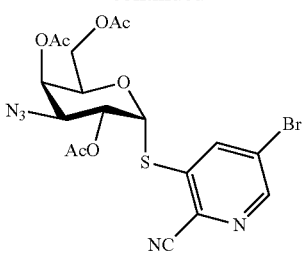

Acetyl 2,4,6-tri-O-acetyl-3-azido-3-deoxy-1-thio-α-D-galactopyranoside (250 mg, 0.64 mmol) and 5-bromo-3-chloro-pyridine-2-carbonitrile (280 mg, 1.28 mmol) were dissolved in DMF (10 mL). Diethylamine (0.15 ml) was added. The reaction was stirred at room temperature with for 20 h. Water (50 mL) and DCM (50 mL) were added. The aqueous phase was extracted with DCM (50 mL×2), the combined organic phases were washed with water (100 mL) and brine (100 mL), dried over anhydrous sodium sulphate. Removal of solvent gave a residue. The residue was purified by column chromatography (PE/EA=3/1) to obtain the product (130 mg, 38%).

5-Chloro-6-cyano-3-pyridyl 2,4,6-tri-O-acetyl-3-azido-3-deoxy-1-thio-α-D-galactopyranoside m/z calcd for $[C_{18}H_{18}ClN_5O_7S]^-$ $[M+H]^+$: 484.0; found: 484.0.

5-Bromo-2-cyano-3-pyridyl 2,4,6-tri-O-acetyl-3-azido-3-deoxy-1-thio-α-D-galactopyranoside m/z calcd for $[C_{18}H18BrN_5O_7S]^-$ $[M+H]^+$: 528.0; found: 528.0.

i10) 5-Chloro-6-cyano-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside and i11) 5-Bromo-2-cyano-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside

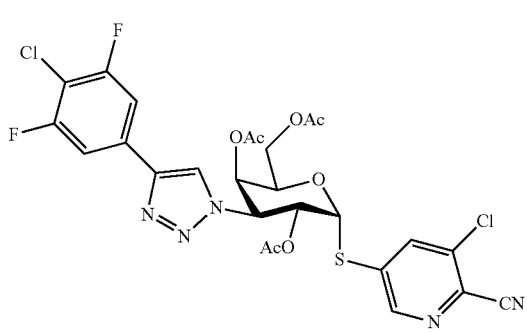

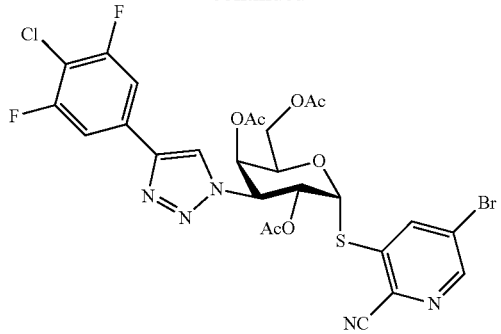

To a mixture of 5-Chloro-6-cyano-3-pyridyl 2,4,6-tri-O-acetyl-3-azido-3-deoxy-1-thio-α-D-galactopyranoside and 5-Bromo-2-cyano-3-pyridyl 2,4,6-tri-O-acetyl-3-azido-3-deoxy-1-thio-α-D-galactopyranoside (130 mg) in CH₃CN (5 mL) were added DIEA (0.23 mL), Copper(I)Iodide (15 mg, 0.08 mmol), CsF (82 mg, 0.54 mmol), 2-(4-chloro-3,5-difluoro-phenyl)ethynyl-trimethyl-silane(132 mg, 0.54 mmol). The reaction was stirred at room temperature for 20 h under a N₂ atmosphere. Water (10 mL) and DCM (10 mL) were added. The aqueous phase was extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=2/1) to obtain the products i10 (80 mg) and i11 (20 mg).

i10) 5-Chloro-6-cyano-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside m/z calcd for $[C_{26}H_{21}Cl_2F_2N_5O_7S]^+$ $[M+H]^+$: 656.0; found: 656.0.

¹H NMR (400 MHz, CDCl₃) δ 8.63 (d, J=1.9 Hz, 1H), 8.01 (d, J=2.0 Hz, 1H), 7.83 (s, 1H), 7.45 (t, J=6.3 Hz, 2H), 6.34 (d, J=5.5 Hz, 1H), 6.16 (dd, J=11.7, 5.6 Hz, 1H), 5.63 (d, J=2.3 Hz, 1H), 5.20 (dd, J=11.7, 3.1 Hz, 1H), 4.78-4.71 (m, 1H), 4.14 (tdd, J=12.8, 8.7, 4.4 Hz, 3H), 2.08 (s, 3H), 2.00 (s, 3H), 1.98 (s, 3H).

i11) 5-Bromo-2-cyano-3-pyridyl 2,4,6-tri-O-acetyl-3-deoxy-3-[4-(4-chloro-3,5-difluorophenyl)-1H-1,2,3-triazol-1-yl]-1-thio-α-D-galactopyranoside m/z calcd for $[C_{26}H_{21}BrClF_2N_5O_7S]+[M+H]^+$: 700.0; found: 700.0.

5-Bromo-6-cyano-3-pyridyl 2,4,6-tri-O-acetyl-3-azido-3-deoxy-1-thio-α-D-galactopyranoside and 5-Chloro-2-cyano-3-pyridyl 2,4,6-tri-O-acetyl-3-azido-3-deoxy-1-thio-α-D-galactopyranoside

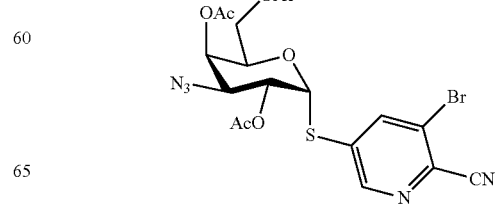

-continued

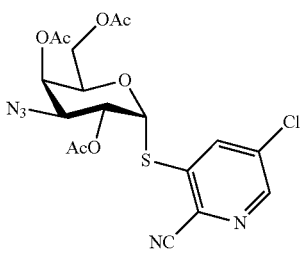

Acetyl 2,4,6-tri-O-acetyl-3-azido-3-deoxy-1-thio-α-D-galactopyranoside (250 mg, 0.64 mmol) and 3-bromo-5-chloro-pyridine-2-carbonitrile (280 mg, 1.28 mmol) were dissolved in DMF (10 mL). Diethylamine (0.15 ml) was added. The reaction was stirred at room temperature with stirring for 20 h. Water (50 mL) and DCM (50 mL) were added. The aqueous phase was extracted with DCM (50 mL×2), the combined organic phases were washed with water (100 mL) and brine (100 mL), dried over anhydrous sodium sulphate. Removal of solvent gave a residue. The residue was purified by column chromatography (PE/EA=3/1) to obtain the product mixture (150 mg, 48%).

5-Bromo-6-cyano-3-pyridyl 2,4,6-tri-O-acetyl-3-azido-3-deoxy-1-thio-α-D-galactopyranoside m/z calcd for $[C_{18}H_{18}BrN_5O_7S]^-$ $[M+H]^+$: 528.0; found: 528.0.

5-Chloro-2-cyano-3-pyridyl 2,4,6-tri-O-acetyl-3-azido-3-deoxy-1-thio-α-D-galactopyranoside m/z calcd for $[C_{18}H_{18}ClN_5O_7S]^-$ $[M+H]^+$: 484.0; found: 484.0.

i12) 5-Bromo-6-cyano-3-pyridyl 2,4,6-tri-O-acetyl-3-azido-3-deoxy-1-thio-α-D-galactopyranoside and i13) 5-Chloro-2-cyano-3-pyridyl 2,4,6-tri-O-acetyl-3-azido-3-deoxy-1-thio-α-D-galactopyranoside

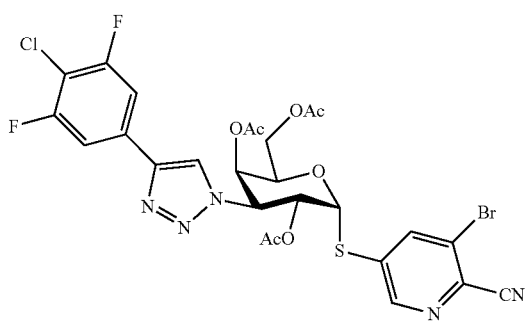

-continued

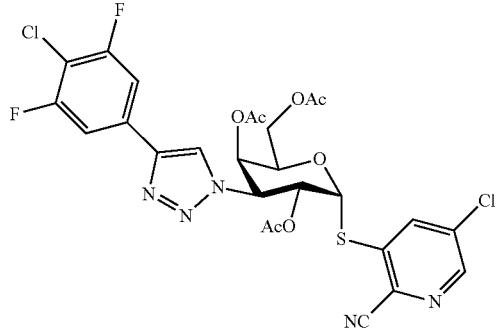

To a mixture of 5-Bromo-6-cyano-3-pyridyl 2,4,6-tri-O-acetyl-3-azido-3-deoxy-1-thio-α-D-galactopyranoside and 5-Chloro-2-cyano-3-pyridyl 2,4,6-tri-O-acetyl-3-azido-3-deoxy-1-thio-α-D-galactopyranoside (150 mg) in CH₃CN (5 mL) were added DIEA (0.25 mL), Copper(I)Iodide (16 mg, 0.08 mmol), CsF (86 mg, 0.57 mmol), 2-(4-chloro-3,5-difluoro-phenyl)ethynyl-trimethyl-silane (140 mg, 0.57 mmol). The reaction was stirred at room temperature with for 20 h under N₂. Water (10 mL) and DCM (10 mL) were added. The aqueous phase was extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=2/1) to obtain the products i12 (80 mg) and i13 (30 mg).

i12) 5-Bromo-6-cyano-3-pyridyl 2,4,6-tri-O-acetyl-3-azido-3-deoxy-1-thio-α-D-galactopyranoside m/z calcd for $[C_{26}H_{21}BrClF_2N_5O_7S]^+[M+H]^+$: 700.0; found: 700.0.
¹H NMR (400 MHz, CDCl₃) δ 8.67 (d, J=2.0 Hz, 1H), 8.16 (d, J=2.0 Hz, 1H), 7.83 (s, 1H), 7.45 (d, J=7.3 Hz, 2H), 6.34 (d, J=5.5 Hz, 1H), 6.16 (dd, J=11.7, 5.6 Hz, 1H), 5.63 (d, J=2.1 Hz, 1H), 5.20 (dd, J=11.7, 3.1 Hz, 1H), 4.84-4.56 (m, 1H), 4.13 (tdd, J=13.7, 11.8, 6.3 Hz, 4H), 2.08 (s, 3H), 2.01 (s, 3H), 1.98 (s, 3H).

i13) 5-Chloro-2-cyano-3-pyridyl 2,4,6-tri-O-acetyl-3-azido-3-deoxy-1-thio-α-D-galactopyranoside m/z calcd for $[C_{26}H_{21}Cl_2F_2N_5O_7S]^+[M+H]^+$: 656.0; found: 656.0.

i14) 5-Chloro-3-pyridyl 2,4,6-tri-O-acetyl-3-deoxy-3-[4-(4-cyano-3,5-difluorophenyl)-1H-1,2,3-triazol-1-yl]-1-thio-α-D-galactopyranoside 2,6-Difluoro-4-(2-trimethylsilylethynyl)benzonitrile

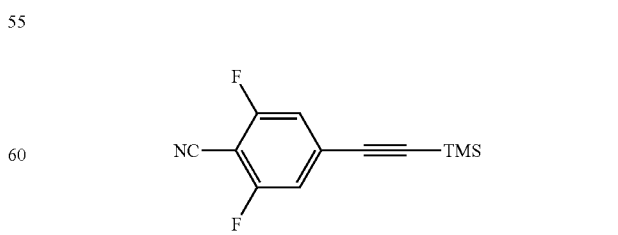

To a solution of 4-bromo-2,6-difluoro-benzonitrile (500 mg, 2.29 mmol) in CH₃CN (10 mL) was added CuI (131 mg, 0.69 mmol), DIPEA (2.0 mL), Pd(PPh₃)₂Cl₂ (161 mg, 0.23 mmol), ethynyl(trimethyl)silane (451 mg, 4.59 mmol). The mixture was heated under $N_2$ at room temperature for 20 h. Removal of solvent gave a residue. The residue was purified by column chromatography (PE/EA=10/1) to obtain the title compound (100 mg, 19%).

m/z calcd for $[C_{12}H_{11}F_2NSi]$ [M]: 235.0; found: 235.0; [M−15]: 220.0; found: 220.0.

5-Chloro-3-pyridyl 2,4,6-tri-O-acetyl-3-deoxy-3-[4-(4-cyano-3,5-difluorophenyl)-1H-1,2,3-triazol-1-yl]-1-thio-α-D-galactopyranoside

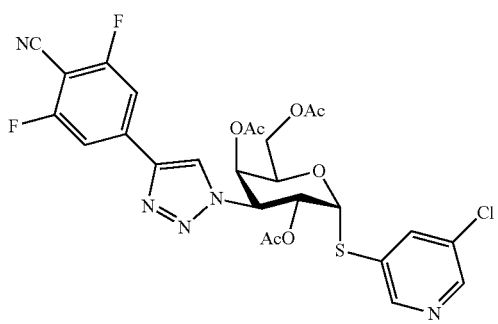

To a solution of 5-chloro-3-pyridyl 2,4,6-tri-O-acetyl-3-azido-3-deoxy-1-thio-α-D-galactopyranoside (50 mg, 0.11 mmol) in $CH_3CN$ (5 mL) was added 2,6-difluoro-4-(2-trimethylsilylethynyl)benzonitrile (100 mg, 0.42 mmol), iodocopper (6 mg, 0.03 mmol), CsF (33 mg, 0.22 mmol), DIEA (0.1 mL). The reaction vessel was purged 3 times with nitrogen. The reaction was concentrated to dryness. The crude product was purified by flash chromatography (EA:PE=1:10 to 1:2, ISCO® 12 g, 25 ml/min, normal phase silica, uv254) to give product (42 mg, 62%).

m/z calcd for $[C_{26}H_{22}ClF_2N_5O_7S]^−$ $[M+H]^+$: 622.0; found: 622.0.

1H NMR (400 MHz, CDCl3) δ 8.57 (d, J=1.9 Hz, 1H), 8.54 (d, J=2.2 Hz, 1H), 7.95 (s, 1H), 7.88 (t, J=2.1 Hz, 1H), 7.52 (d, J=8.0 Hz, 2H), 6.15 (d, J=5.5 Hz, 1H), 6.12 (dd, J=11.1, 5.6 Hz, 1H), 5.64-5.60 (m, 1H), 5.23 (dd, J=11.0, 3.1 Hz, 1H), 4.90-4.84 (m, 1H), 4.17-4.09 (m, 2H), 2.07 (s, 3H), 2.05 (s, 3H), 1.99 (s, 3H).

i15) 5-Chloro-3-pyridyl 2,4,6-tri-O-acetyl-3-deoxy-3-[4-(3,5-difluoro-4-trifluoromethyl-phenyl)-1H-1,2,3-triazol-1-yl]-1-thio-α-D-galactopyranoside 2-(3,5-difluoro-4-trifluoromethyl-phenyl)ethynyl-trimethyl-silane

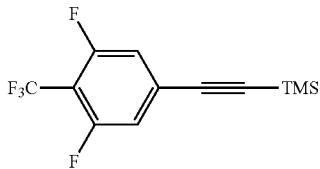 [SMILES: C[Si](C)(C)C#Cc1cc(F)c(C(F)(F)F)c(F)c1]

To a solution of 5-bromo-1,3-difluoro-2-(trifluoromethyl) benzene (500 mg, 1.92 mmol) in $CH_3CN$ (10 mL) was added CuI (109 mg, 0.57 mmol), DIPEA (1.6 mL), $Pd(PPh_3)_2Cl_2$ (54 mg, 0.07 mmol), ethynyl(trimethyl)silane (376 mg, 3.83 mmol). The mixture was heated under $N_2$ at room temperature for 20 h. Removal of solvent gave a residue which was purified by column chromatography (PE/EA=10/1) to obtain product (60 mg, 11%).

m/z calcd for $[C_{12}H_{11}F_5Si]$ [M]: 278.0; found: 278.0; [M−15]: 263.0; found: 263.0.

5-Chloro-3-pyridyl 2,4,6-tri-O-acetyl-3-deoxy-3-[4-(3,5-difluoro-4-trifluoromethyl-phenyl)-1H-1,2,3-triazol-1-yl]-1-thio-α-D-galactopyranoside

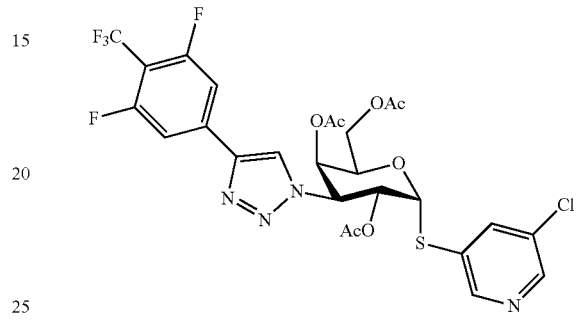

To a solution of 5-chloro-3-pyridyl 2,4,6-tri-O-acetyl-3-azido-3-deoxy-1-thio-α-D-galactopyranoside (50 mg, 0.11 mmol) in $CH_3CN$ (5 mL) was added 2-(3,5-difluoro-4-trifluoromethyl-phenyl)ethynyl-trimethyl-silane (60 mg, 0.22 mmol), CuI (6 mg, 0.03 mmol), CsF (33 mg, 0.22 mmol), DIEA (0.1 mL). The reaction vessel was purged 3 times with nitrogen. The reaction was concentrated to dryness. The crude product was purified by flash chromatography (EA:PE=1:10 to 1:2, ISCO® 12 g, 25 ml/min, normal phase silica, uv254) to give the title compound (33 mg, 45%).

m/z calcd for $[C_{26}H_{22}ClF_5N_4O_7S]^−$ $[M+H]^+$: 665.0; found: 665.0.

1H NMR (400 MHz, CDCl3) δ 8.58 (d, J=1.9 Hz, 1H), 8.54 (d, J=2.2 Hz, 1H), 7.90 (s, 1H), 7.88 (t, J=2.1 Hz, 1H), 7.47 (d, J=10.1 Hz, 2H), 6.15 (d, J=5.6 Hz, 1H), 6.11 (dd, J=11.2, 5.6 Hz, 1H), 5.65-5.60 (m, 1H), 5.23 (dd, J=11.2, 3.1 Hz, 1H), 4.90-4.81 (m, 1H), 4.13 (ddd, J=19.4, 11.7, 6.3 Hz, 2H), 2.07 (s, 3H), 2.05 (s, 3H), 1.99 (s, 3H).

i16) 5-Chloro-3-pyridyl 3-deoxy-3-[4-(3,5-difluoro-4-methylphenyl)-1H-1,2,3-triazol-1-yl]-1-thio-α-D-galactopyranoside 2-(3,5-difluoro-4-methyl-phenyl)ethynyl-trimethyl-silane

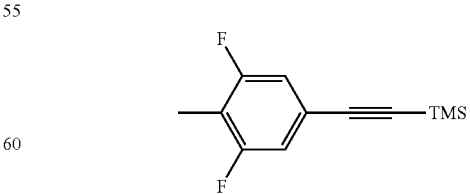

To a solution of 5-bromo-1,3-difluoro-2-methyl-benzene (500 mg, 2.42 mmol) in DMF (2.5 mL) was added CuI (138 mg, 0.72 mmol), DIPEA (2.5 mL), $Pd(PPh_3)_2Cl_2$ (170 mg, 0.24 mmol), ethynyl(trimethyl)silane (474 mg, 4.83 mmol).

The mixture was heated under N₂ at 100° C. for 2 h. The mixture was cooled to room temperature and added 100-200 silica (5 g). The mixture was purified by column chromatography (PE/EA=10/1) to obtain the title compound (100 mg, 18.5%).

m/z calcd for [$C_{12}H_{14}F_2Si$] [M]: 224.0; found: 224.0; [M−15]: 209.0; found: 209.0.

5-Chloro-3-pyridyl 3-deoxy-3-[4-(3,5-difluoro-4-methylphenyl)-1H-1,2,3-triazol-1-yl]-1-thio-α-D-galactopyranoside

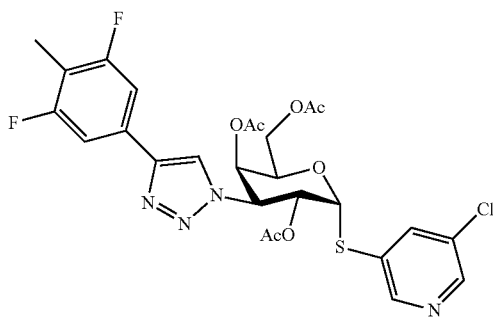

To a solution of 5-chloro-3-pyridyl 2,4,6-tri-O-acetyl-3-azido-3-deoxy-1-thio-α-D-galactopyranoside (50 mg, 0.11 mmol) in CH₃CN (5 mL) was added 2-(3,5-difluoro-4-methyl-phenyl)ethynyl-trimethyl-silane (100 mg, 0.45 mmol), iodocopper (6 mg, 0.03 mmol), CsF (33 mg, 0.22 mmol), DIEA (0.1 mL). The reaction vessel was purged 3 times with nitrogen. The reaction was concentrated to dryness. The crude product was purified by flash chromatography (EA:PE=1:10 to 1:2, ISCO® 12 g, 25 ml/min, normal phase silica, uv254) to give the title compound (50 mg, 56%).

m/z calcd for [$C_{26}H_{25}ClF_2N_4O_7S$]⁻ [M+H]⁺: 611.0; found: 611.0.

1H NMR (400 MHz, CDCl3) δ 8.58 (d, J=1.9 Hz, 1H), 8.53 (d, J=2.2 Hz, 1H), 7.88 (t, J=2.1 Hz, 1H), 7.78 (s, 1H), 7.30 (d, J=7.6 Hz, 2H), 6.14 (d, J=5.6 Hz, 1H), 6.09 (dd, J=11.5, 5.6 Hz, 1H), 5.63 (d, J=2.2 Hz, 1H), 5.23 (dd, J=11.5, 3.1 Hz, 1H), 4.86 (dd, J=7.1, 5.1 Hz, 1H), 4.13 (ddd, J=19.4, 11.7, 6.3 Hz, 2H), 2.07 (s, 3H), 2.04 (s, 3H), 1.99 (s, 3H).

i117) 5-Chloro-3-pyridyl 2,4,6-tri-O-acetyl-3-deoxy-3-[4-(4-bromo-3,5-difluorophenyl)-1H-1,2,3-triazol-1-yl]-1-thio-α-D-galactopyranoside

2-(4-Bromo-3-fluoro-phenyl)ethynyl-trimethyl-silane

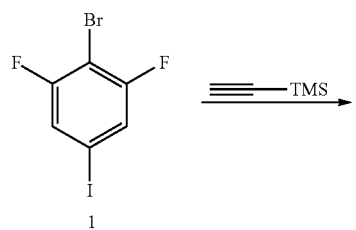

-continued

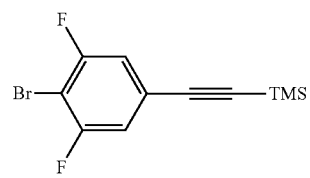

To a solution of 2-bromo-1,3-difluoro-5-iodo-benzene (500 mg, 1.57 mmol) in CH₃CN (5 mL) was added CuI (90 mg, 0.47 mmol), DIPEA (1.3 mL), Pd(PPh₃)₂Cl₂ (110 mg, 0.16 mmol), ethynyl(trimethyl)silane (308 mg, 3.14 mmol). The mixture was stirred at room temperature under N₂ for 20 h. Removal of solvent gave a residue. The residue was purified by column chromatography (PE/EA=10/1) to obtain the title compound (100 mg, 22.1%).

m/z calcd for [$C_{11}H_{11}BrF_2Si$] [M]: 287.0; found: 287.0; [M−15]: 272.0; found: 272.0.

5-Chloro-3-pyridyl 2,4,6-tri-O-acetyl-3-deoxy-3-[4-(4-bromo-3,5-difluorophenyl)-1H-1,2,3-triazol-1-yl]-1-thio-α-D-galactopyranoside

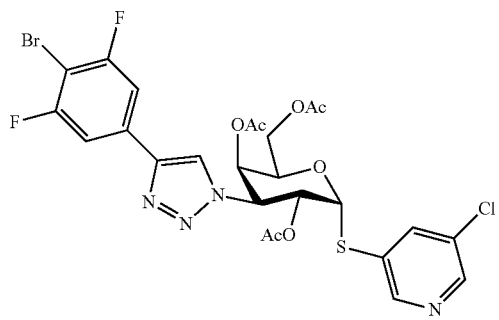

To a solution of 3-azido-3-deoxy-2,4,6-tri-O-acetyl-1-(5-chloropyridine-3-thiol-yl)-α-D-galactopyranoside (50 mg, 0.11 mmol) in CH₃CN (5 mL) was added 2-(4-bromo-3,5-difluoro-phenyl)ethynyl-trimethyl-silane (100 mg, 0.35 mmol), CuI (6 mg, 0.03 mmol), DIEA (0.1 mL). The reaction vessel was purged 3 times with nitrogen. The reaction was concentrated to dryness. The crude product was purified by flash chromatography (EA:PE=1:10 to 1:2, ISCO® 12 g, 25 ml/min, normal phase silica, uv254) to give the title compound (65 mg, 88.3%).

m/z calcd for [$C_{25}H_{22}BrClF_2N_4O_7S$]⁺[M+H]⁺: 675.0; found: 675.0.

¹H NMR (400 MHz, CDCl₃) δ 8.57 (d, J=1.9 Hz, 1H), 8.53 (d, J=2.2 Hz, 1H), 7.88 (t, J=2.1 Hz, 1H), 7.84 (s, 1H), 7.42 (d, J=7.1 Hz, 2H), 6.15 (d, J=5.6 Hz, 1H), 6.10 (dd, J=11.4, 5.6 Hz, 1H), 5.63 (d, J=2.0 Hz, 1H), 5.23 (dd, J=11.4, 3.1 Hz, 1H), 4.87 (dd, J=7.1, 5.4 Hz, 1H), 4.25-4.03 (m, 2H), 2.07 (s, 3H), 2.04 (s, 3H), 1.99 (s, 3H).

i18) 5-Chloro-3-pyridyl 2,4,6-tri-O-acetyl-3-deoxy-3-[4-(3,4-dichloro-5-fluorophenyl)-1H-1,2,3-triazol-1-yl]-1-thio-α-D-galactopyranoside 4-bromo-2-chloro-6-fluoro-aniline

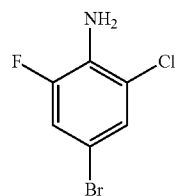

NCS (1.4 g, 10.5 mmol) was added portionwise to a mixture of 4-bromo-2-fluoro-aniline (2 g, 10.5 mmol) in acetonitrile (20 ml). The mixture was stirred at reflux for 2 hours, cooled and poured in a mixture of water and K₂CO₃ 10%. The mixture was extracted with DCM. The organic layer was dried over magnesium sulfate, filtered and the solvent evaporated. The residue was purified by column chromatography on silica gel (eluent:PE/ethyl acetate 80/20) to give the title compound 1.50 g (63.5%). 1H NMR (400 MHz, CDCl3) δ 7.21 (t, J=1.9 Hz, 1H), 7.09 (dd, J=10.0, 2.1 Hz, 1H), 4.36-3.92 (br, 2H).

5-bromo-1,2-dichloro-3-fluoro-benzene

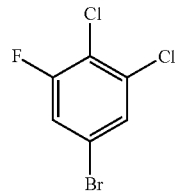

To a stirred suspension of dichlorocopper (1.4 g, 10.7 mmol) and tert-butyl nitrite (1.38 g, 13.4 mmol) in acetonitrile (10 ml), heated at 60° C., was added a solution of 4-bromo-2-chloro-6-fluoro-aniline (1.20 g, 5.35 mmol) in acetonitrile (10 mL) dropwise over 50 minutes. After stirring at 60° C. for 1 hour, the mixture was poured into 20% hydrochloric acid (50 ml) and extracted with ether (2*30 ml). The crude product was purified by flash chromatography on silica gel eluding with hexane to provide the title compound 1.10 g (84.4%).

1H NMR (400 MHz, CDCl3) δ 7.38 (t, J=1.9 Hz, 1H), 7.21-7.17 (m, 1H).

((3,4-dichloro-5-fluorophenyl)ethynyl)trimethylsilane

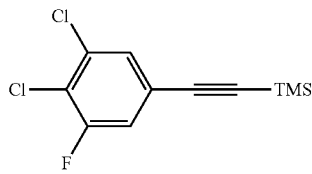 [SMILES: C[Si](C)(C)C#Cc1cc(F)c(Cl)c(Cl)c1]

To a solution of 5-bromo-1,2-dichloro-3-fluorobenzene (0.5 g, 2.05 mmol), Copper(I)Iodide (117 mg, 0.615 mmol), and Bis(Triphenylphosphine)palladium(II) chloride (224 mg, 0.308 mmol) Diisopropylamine (2075 mg, 20.5 mmol) in N,N-dimethylformamide (5 mL) was added ethynyl(trimethyl)silane (403 mg, 4.10 mmol). The mixture was stirred at 80° C. overnight under nitrogen atmosphere. After removal of the solvent under reduce pressure, the residue was purified by column with Hexane as the mobile-phase to give the title compound 180 mg (33.6%).

1H NMR (400 MHz, CDCl3) δ 7.30 (t, J=1.7 Hz, 1H), 7.08 (dt, J=9.4, 4.7 Hz, 1H), 0.18 (s, 9H).

5-Chloro-3-pyridyl 2,4,6-tri-O-acetyl-3-deoxy-3-[4-(3,4-dichloro-5-fluorophenyl)-1H-1,2,3-triazol-1-yl]-1-thio-α-D-galactopyranoside

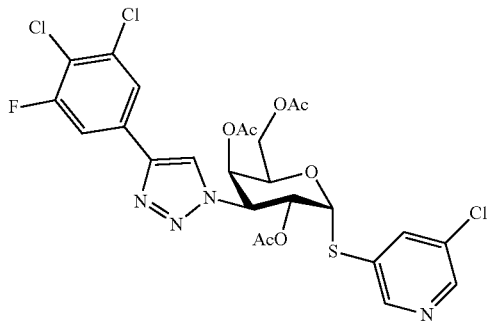

A mixture of 5-chloro-3-pyridyl 2,4,6-tri-O-acetyl-3-azido-3-deoxy-1-thio-α-D-galactopyranoside (50 mg, 0.109 mmol) and 2-(3,4-dichloro-5-fluoro-phenyl)ethynyl-trimethyl-silane (57 mg, 0.218 mmol) were dissolved in CH₃CN (5 mL). Then CsF (33.1 mg, 0.218 mmol), and DIEA (0.0560 mL, 0.327 mmol) were added. The mixture was stirred at rt for 5 min. CuI (6.23 mg, 0.0327 mmol) was added. The mixture was stirred at rt over night. Then the mixture was concentrated and purified by column chromatography (SiO₂/PE/EA 2:1=1:1) to give the title compound 30.0 mg (42.5%).

m/z calcd for [C25H22Cl3FN4O7S]+[M+H]+: 647; found: 647.

i19) 5-Chloro-3-pyridyl 2,4,6-tri-O-acetyl-3-deoxy-3-[4-(4-chloro-3-fluorophenyl)-1H-1,2,3-triazol-1-yl]-1-thio-α-D-galactopyranoside 2-(4-chloro-3-fluoro-phenyl)ethynyl-trimethyl-silane

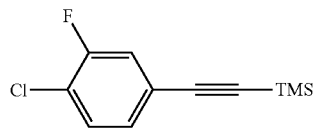 [SMILES: C[Si](C)(C)C#Cc1ccc(Cl)c(F)c1]

To a solution of 4-bromo-1-chloro-2-fluoro-benzene (500 mg, 2.39 mmol) in CH₃CN (5 mL) was added CuI (136 mg, 0.72 mmol), DIPEA (2.0 mL), Pd(PPh₃)₂Cl₂ (168 mg, 0.24 mmol), ethynyl(trimethyl)silane (469, 4.77 mmol). The mixture was heated under N₂ at 50° C. for 20 h. Removal of solvent gave a residue. The residue was purified by column chromatography (PE/EA=10/1) to give the title compound (150 mg, 28%).

m/z calcd for [C$_{11}$H$_{12}$ClFSi] [M]: 226.0; found: 226.0; [M−15]: 211.0; found: 211.0.

5-Chloro-3-pyridyl 2,4,6-tri-O-acetyl-3-deoxy-3-[4-(4-chloro-3-fluorophenyl)-1H-1,2,3-triazol-1-yl]-1-thio-α-D-galactopyranoside

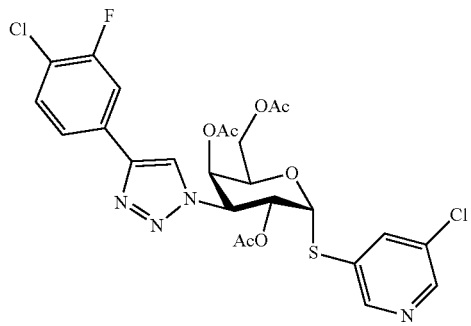

To a solution of 5-chloro-3-pyridyl 2,4,6-tri-O-acetyl-3-azido-3-deoxy-1-thio-α-D-galactopyranoside (50 mg, 0.11 mmol) in CH$_3$CN (5 mL) was added 2-(3,5-difluoro-4-methyl-phenyl)ethynyl-trimethyl-silane (150 mg, 0.66 mmol), iodocopper (6 mg, 0.03 mmol), CsF (33 mg, 0.22 mmol), DIEA (0.1 mL). The reaction vessel was purged 3 times with nitrogen. The reaction was concentrated to dryness. The crude product was purified by flash chromatography (EA:PE=1:10 to 1:2, ISCO® 12 g, 25 ml/min, normal phase silica, U254) to give the title compound (60 mg, 90%).

m/z calcd for [C$_{25}$H$_{23}$Cl$_2$FN$_4$O$_7$S]$^-$ [M+H]$^+$: 613.0; found: 613.0.

$^1$H NMR (400 MHz, CDCl$_3$) δ 8.57 (d, J=1.9 Hz, 1H), 8.53 (d, J=2.2 Hz, 1H), 7.88 (t, J=2.1 Hz, 1H), 7.80 (s, 1H), 7.63 (dd, J=9.9, 1.8 Hz, 1H), 7.55-7.50 (m, 1H), 7.49-7.41 (m, 1H), 6.14 (d, J=5.5 Hz, 1H), 6.10 (dd, J=11.4, 5.5 Hz, 1H), 5.63 (d, J=2.1 Hz, 1H), 5.23 (dd, J=11.4, 3.1 Hz, 1H), 4.90-4.84 (m, 1H), 4.13 (ddd, J=19.4, 11.7, 6.3 Hz, 2H), 2.07 (s, 3H), 2.04 (s, 3H), 1.99 (s, 3H).

i20) 5-Chloro-3-pyridyl 2,4,6-tri-O-acetyl-3-deoxy-3-[4-(4-chloro-3-fluorophenyl)-1H-1,2,3-triazol-1-yl]-1-thio-α-D-galactopyranoside 3-fluoro-5-((trimethylsilyl)ethynyl)pyridine

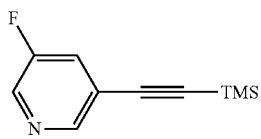 [SMILES: C[Si](C)(C)C#Cc1cncc(F)c1]

To a solution of 3-bromo-5-fluoropyridine (0.5 g, 2.84 mmol), Copper(I)Iodide (81.2 mg, 0.426 mmol), and Bis(Triphenylphosphine)palladium (II) chloride (311 mg, 0.426 mmol) in Diisopropylamine (5750 mg, 56.8 mmol) was added ethynyl(trimethyl)silane (419 mg, 4.26 mmol). The mixture was stirred at 80° C. overnight under nitrogen atmosphere. After removal of the solvent under reduced pressure, the residue was purified by flash chromatography using hexane as the mobile-phase to give the title compound. 150 mg (27.3%)

1H NMR (400 MHz, CDCl3) δ 8.42 (s, 1H), 8.33 (d, J=2.8 Hz, 1H), 7.39 (ddd, J=9.0, 2.7, 1.6 Hz, 1H), 0.20 (s, 9H).

3,4-Dichlorophenyl 2,4,6-tri-O-acetyl-3-azido-3-deoxy-1-thio-α-D-galactopyranoside

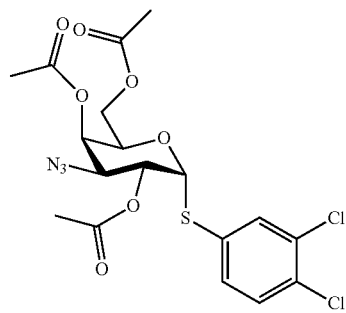

To a solution of 3,4-dichlorobenzenethiol (4.61 g, 0.03 mol) in N,N-dimethylformamide (0.05 L) was added NaH (0.53 g, 0.02 mol). The mixture was stirred at room temperature for 30 min. 2,4,6-Tri-O-acetyl-3-azido-1-chloro-3-deoxy-β-D-galactopyranoside (4.5 g, 0.01 mol) in DMF (10 mL) was added and the reaction mixture was stirred at 50° C. for 20 h. The mixture was diluted with DCM (100 mL), 0.5 M citric acid (50 mL) and water (50 mL). The organic phase was isolated and washed with water (100 mL×2) and concentrated. The residue was purified by column chromatography (SiO$_2$/PE:EA=3:1) to give the title compound 5.1 g (81%) as a white solid. m/z calcd for [C$_{18}$H$_{19}$Cl$_2$N$_3$O$_7$S]$^+$ [M+NH$_4$]$^+$:509.0; found: 509.0.

5-Chloro-3-pyridyl 2,4,6-tri-O-acetyl-3-deoxy-3-[4-(4-chloro-3-fluorophenyl)-1H-1,2,3-triazol-1-yl]-1-thio-α-D-galactopyranoside

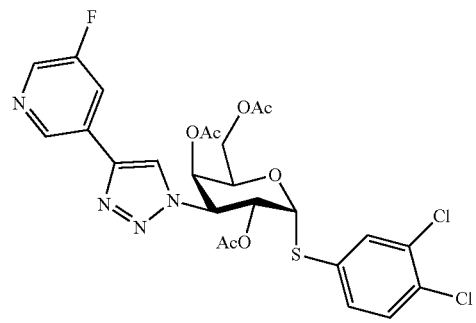

A mixture of 3,4-dichlorophenyl 2,4,6-tri-O-acetyl-3-azido-3-deoxy-1-thio-α-D-galactopyranoside (50 mg, 0.102 mmol) and 2-(5-fluoro-3-pyridyl)ethynyl-trimethyl-silane (85 mg, 0.406 mol) were dissolved in CH$_3$CN (5 ml). Then CsF (30.9 mg, 0.203 mmol), and DIEA (0.174 ml, 1.02 mmol) were added. The mixture was stirred at rt for 5 min. Copper(I)Iodide (5.80 mg, 0.0305 mmol) was added. The mixture was stirred at r.t over night. Then the mixture was concentrated and purified by column chromatography (SiO$_2$/PE/EA 2:1=1:1) to give the the compound. 45.0 mg (72.2%).

1H NMR (400 MHz, CDCl3) δ 8.78 (s, 1H), 8.46 (d, J=2.7 Hz, 1H), 7.98-7.94 (m, 1H), 7.91 (s, 1H), 7.62 (d, J=2.1 Hz, 1H), 7.43 (d, J=8.4 Hz, 1H), 7.34 (dd, J=8.4, 2.1 Hz, 1H), 6.15 (d, J=5.6 Hz, 1H), 6.10 (dd, J=11.4, 5.6 Hz, 1H), 5.62 (d, J=2.2 Hz, 1H), 5.23 (dd, J=11.4, 3.1 Hz, 1H), 4.84 (t, J=6.3 Hz, 1H), 4.12 (ddd, J=19.1, 11.6, 6.4 Hz, 2H), 2.08 (s, 3H), 2.01 (s, 3H), 1.98 (s, 3H).

i21) 5-Chloro-3-pyridyl 2,4,6-tri-O-acetyl-3-deoxy-3-[4-(3,4-dichlorophenyl)-1H-1,2,3-triazol-1-yl]-1-thio-α-D-galactopyranoside 2-(3,4-dichlorophenyl)ethynyl-trimethyl-silane

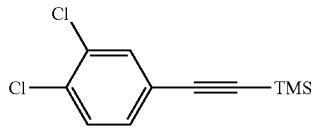

To a solution of 4-bromo-1,2-dichloro-benzene (500 mg, 2.21 mmol) in CH$_3$CN (5 mL) was added CuI (126 mg, 0.66 mmol), DIPEA (2.0 mL), Pd(PPh$_3$)$_2$Cl$_2$ (155 mg, 0.22 mmol), ethynyl(trimethyl)silane (435, 4.43 mmol). The mixture was heated under N$_2$ at 50° C. for 20 h. Removal of solvent gave a residue. The residue was purified by column chromatography (PE/EA=10/1) to give the title compound (130 mg, 24.1%).

m/z calcd for [C$_{11}$H$_{12}$Cl$_2$Si] [M]: 242.0; found: 242.0; [M−15]: 227.0; found: 227.0.

5-Chloro-3-pyridyl 2,4,6-tri-O-acetyl-3-deoxy-3-[4-(3,4-dichlorophenyl)-1H-1,2,3-triazol-1-yl]-1-thio-α-D-galactopyranoside

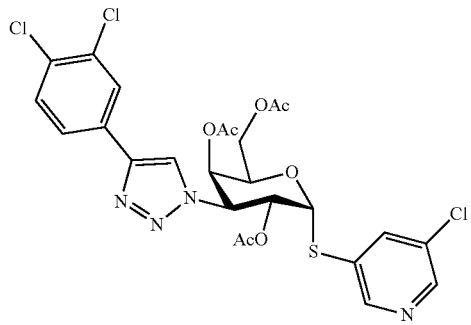

To a solution of 5-chloro-3-pyridyl 2,4,6-tri-O-acetyl-3-azido-3-deoxy-1-thio-α-D-galactopyranoside (50 mg, 0.11 mmol) in CH$_3$CN (5 mL) was added 2-(3,4-dichlorophenyl)ethynyl-trimethyl-silane(130 mg, 0.53 mmol), CuI (6 mg, 0.03 mmol), CsF (33 mg, 0.22 mmol), DIEA (0.1 mL). The reaction vessel was purged 3 times with nitrogen. The reaction was concentrated to dryness. The crude product was purified by flash chromatography (EA:PE=1:10 to 1:2, ISCO® 12 g, 25 ml/min, normal phase silica, uv254) to give the title compound (50 mg, 73%).

m/z calcd for [C$_{25}$H$_{23}$Cl$_3$N$_4$O$_7$S]$^-$ [M+H]$^+$: 629.0; found: 629.0.

1H NMR (400 MHz, CDCl3) δ 8.58 (d, J=1.9 Hz, 1H), 8.53 (d, J=2.2 Hz, 1H), 7.92 (d, J=2.0 Hz, 1H), 7.88 (t, J=2.1 Hz, 1H), 7.82 (s, 1H), 7.64 (dd, J=8.3, 2.0 Hz, 1H), 7.51 (d, J=8.3 Hz, 1H), 6.15 (d, J=5.6 Hz, 1H), 6.10 (dd, J=11.4, 5.6 Hz, 1H), 5.63 (d, J=2.1 Hz, 1H), 5.23 (dd, J=11.4, 3.1 Hz, 1H), 4.89-4.84 (m, 1H), 4.21-4.05 (m, 2H), 2.07 (s, 3H), 2.04 (s, 3H), 1.99 (s, 3H).

i22) 3,4-Dichlorophenyl 2,4,6-tri-O-acetyl-3-deoxy-3-[4-(5-chloro-3-pyridyl)-1H-1,2,3-triazol-1-yl]-1-thio-α-D-galactopyranoside 3-Chloro-5-((trimethylsilyl)ethynyl)pyridine

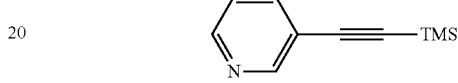

To a solution of 3-bromo-5-chloropyridine (0.5 g, 2.60 mmol), Copper(I)Iodide (74.2 mg, 0.390 mmol), and Bis(Triphenylphosphine)palladium (II) chloride (284 mg, 0.39 mmol) in Diisopropylamine (15 mL) was added ethynyl (trimethyl)silane (383 mg, 3.90 mmol). The mixture was stirred at 80° C. overnight under nitrogen atmosphere. The solvents were removed under reduced pressure and the residue was purified by column chromatography with hexane as the mobile-phase to give the title compound 230 mg (42.2%).

1H NMR (400 MHz, CDCl3) δ 8.48 (d, J=1.7 Hz, 1H), 8.42 (d, J=2.3 Hz, 1H), 7.68-7.66 (m, 1H), 0.19 (s, 9H).

3,4-Dichlorophenyl 2,4,6-tri-O-acetyl-3-deoxy-3-[4-(5-chloro-3-pyridyl)-1H-1,2,3-triazol-1-yl]-1-thio-α-D-galactopyranoside

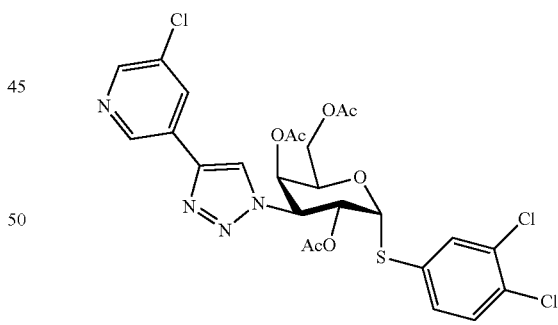

3,4-dichlorophenyl 2,4,6-tri-O-acetyl-3-azido-3-deoxy-1-thio-α-D-galactopyranoside (50 mg, 0.102 mmol) and 2-(5-chloro-3-pyridyl)ethynyl-trimethyl-silane (85 mg, 0.44 mmol) were dissolved in CH$_3$CN (5 ml). Then CsF (30.9 mg, 0.203 mmol), and DIEA (0.174 ml, 1.02 mmol) were added. The mixture was stirred at rt for 5 min. Copper(I) Iodide (5.80 mg, 0.0305 mmol) was added. The mixture was stirred at rt over night. Then the mixture was concentrated and purified by column chromatography (SiO$_2$/PE/EA 2:1=1:1) to give the title compound. 45.0 mg (70.3%).

1H NMR (400 MHz, CDCl3) δ 8.77 (d, J=1.8 Hz, 1H), 8.48 (d, J=2.3 Hz, 1H), 8.15 (t, J=2.1 Hz, 1H), 7.84 (s, 1H), 7.55 (d, J=2.1 Hz, 1H), 7.36 (d, J=8.4 Hz, 1H), 7.27 (dd, J=8.4, 2.1 Hz, 1H), 6.08 (d, J=5.6 Hz, 1H), 6.03 (dd, J=11.4, 5.6 Hz, 1H), 5.55 (d, J=2.1 Hz, 1H), 5.16 (dd, J=11.4, 3.1 Hz, 1H), 4.77 (t, J=6.3 Hz, 1H), 4.14-3.94 (m, 2H), 2.01 (s, 3H), 1.94 (s, 3H), 1.91 (s, 3H).

REFERENCES

Aits S, Kricker J, Liu B, Ellegaard A M, Hämälistö S, Tvingsholm S, Corcelle-Termeau E, Høgh S, Farkas T, Holm Jonassen A, Gromova I, Mortensen M, Jäättelä M. (2015) Sensitive detection of lysosomal membrane permeabilization by lysosomal galectin puncta assay Autophagy. 2015; 11(8):1408-24.

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. *Infect. Immun.* Vol. 69: 832-837.

Arthur C M, Baruffi M D, Cummings R D, Stowell S R. (2015) Evolving mechanistic insights into galectin functions. Methods Mol Biol. 1207:1-35.

Blanchard H, Yu X, Collins P M, Burn-Erdene K. (2014) Galectin-3 inhibitors: a patent review (2008-present). Expert Opin Ther Pat. 2014 October; 24(10):1053-65.

Blidner A G, Méndez-Huergo S P, Cagnoni A J, Rabinovich G A. (2015) Re-wiring regulatory cell networks in immunity by galectin-glycan interactions. FEBS Lett. 2015 Sep. 6. pii: S0014-5793(15)00807-8.

Chen, W.-S., Leffler H., Nilsson, U. J., Panjwani, N. (2012). Targeting Galectin-1 and Galectin-3 Attenuates VEGF-A-induced Angiogenesis; *Mol. Biol. Cell* (suppl), Abstract No. 2695.

Clare D K, Magescas J, Piolot T, Dumoux M, Vesque C, Pichard E, Dang T, Duvauchelle B, Poirier F, Delacour D. (2014) Basal foot MTOC organizes pillar MTs required for coordination of beating cilia. Nat Commun. 5:4888.

Cumpstey, I., Carlsson, S., Leffler, H. and Nilsson, U. J. (2005) Synthesis of a phenyl thio-ß-D-galactopyranoside library from 1,5-difluoro-2,4-dinitrobenzene: discovery of efficient and selective monosaccharide inhibitors of galectin-7. *Org. Biomol. Chem.* 3: 1922-1932.

Cumpstey, I., Sundin, A., Leffler, H. and Nilsson, U. J. (2005) $C_2$-Symmetrical thiodigalactoside bis-benzamido derivatives as high-affinity inhibitors of galectin-3: Efficient lectin inhibition through double arginine-arene interactions. *Angew. Chem. Int. Ed.* 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. *Chem. Eur. J.* 14: 4233-4245.

Delaine, T., Cumpstey, I., Ingrassia, L., Le Mercier, M., Okechukwu, P., Leffler, H., Kiss, R., and Nilsson, U. J. (2008). Galectin-Inhibitory Thiodigalactoside Ester Derivatives Have Anti-Migratory Effects in Cultured Lung and Prostate Cancer Cells. *J Med Chem* 51; 8109-8114.

Demotte, N., Wieers, G., van der Smissen, P., Moser, M., Schmidt, C., Thielemans, K., et al., (2010). Cancer Res. 70; 7476-7488.

Ebrahim A H, Alalawi Z, Mirandola L, Rakhshanda R, Dahlbeck S, Nguyen D, Jenkins M1, Grizzi F, Cobos E, Figueroa J A, Chiriva-Internati M (2014) Galectins in cancer: carcinogenesis, diagnosis and therapy. Ann Transl Med. 2014 September; 2(9):88.

Elola M T, Blidner A G, Ferragut F, Bracalente C, Rabinovich G A. (2015) Assembly, organization and regulation of cell-surface receptors by lectin-glycan complexes. Biochem J. 2015 Jul. 1; 469(1):1-16.

Farkas, I.; Szabó, I. F.; Bognar, R.; Anderle, D. Carbohydr. Res. 1976, 48, 136-138.

Funasaka T, Raz A, Nangia-Makker P. (2014) Nuclear transport of galectin-3 and its therapeutic implications. Semin Cancer Biol. 2014 August; 27:30-8.

Giguère, D.; Bonin, M.-A.; Cloutier, P.; Patnam, R.; St-Pierre, C.; Sato, S.; Roy, R. Bioorganic & Medicinal Chemistry 2008, 16, 7811-7823.

Giguère, D.; André, S.; Bonin, M.-A.; Bellefleur, M.-A.; Provencal, A.; Cloutier, P.; Pucci, B.; Roy, R.; Gabius, H.-J. Bioorganic & Medicinal Chemistry 2011, 19, 3280-3287

Giguere, D., Patnam, R., Bellefleur, M.-A., St.-Pierre, C., Sato, S., and Roy, R. (2006). Carbohydrate triazoles and isoxazoles as inhibitors of galectins-1 and -3. *Chem Commun:* 2379-2381.

Glinsky, G. V., Price, J. E., Glinsky, V. V., Mossine, V. V., Kiriakova, G., and Metcalf, J. B. (1996). *Cancer Res* 56: 5319-5324.

Synthetic Galectin-3 Inhibitor Increases Metastatic Cancer Cell Sensitivity to Taxol-Induced Apoptosis In Vitro and In Vivo. *Neoplasia* 11; 901-909.

Huflejt, M. E. and Leffler, H. (2004) Galectin-4 in normal tissues and cancer. *Glycoconj. J.* 20: 247-255.

Ingrassia et al. (2006) A Lactosylated Steroid Contributes in Vivo Therapeutic Benefits in Experimental Models of Mouse Lymphoma and Human Glioblastoma. *J. Med. CHem.* 49: 1800-1807.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast *Cancer. Clin. Cancer Res.* 9: 2374-2383.

Kouo, T., Huang, L., Pucsek, A. B., Cao, M., Solt, S., Armstrong, T., Jaffee, E. (2015) *Cancer Immonol. Res.* 3: 412-23

Leffler, H. and Barondes, S. H. (1986) Specificity of binding of three soluble rat lung lectins to substituted and unsubstituted mammalian beta-galactosides. J. Biol. Chem. 261:10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Lepur A, Salomonsson E, Nilsson U J, Leffler H. (2012) Ligand induced galectin-3 protein self-association. J Biol Chem. 2012 Jun. 22; 287(26):21751-6.

Li L C, Li J, Gao J. (2014) Functions of galectin-3 and its role in fibrotic diseases. J Pharmacol Exp Ther. 2014 November; 351(2):336-43.

MacKinnon, A. C., Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. *J. Immun.* 180; 2650-2658.

Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1 driven lung fibrosis by Galectin-3. *Am. J. Resp. Crit. Care Med.*, in press.

Massa, S. M., Cooper, D. N. W., Leffler, H., Barondes, S. H. (1993) L-29, an endogenous lectin, binds to glycoconjugate ligands with positive cooperativity. *Biochemistry* 32: 260-267.

Melero, I., Berman, D. M., Aznar, M. A., Korman, A. J., Gracia, J. L. P., Haanen, J. (2015) *Nature Reviews Cancer*, 15: 457-472

Partridge, E. A., Le Roy, C., Di Guglielmo, G. M., Pawling, J., Cheung, P., Granovsky, M., Nabi, I. R., Wrana, J. L., and Dennis, J. W. (2004). Regulation of cytokine receptors by Golgi N-glycan processing and endocytosis. *Science* 306: 120-124.

Pienta, K. J., Naik, H., Akhtar, A., Yamazaki, K., Reploge, T. S., Lehr, J., Donat, T. L., Tait, L., Hogan, V., and Raz, A. (1995). Inhibition of spontaneous metastasis in a rat prostate cancer model by oral administration of modified citrus pectin. *J Natl Cancer Inst* 87, 348-353.

Ramos-Soriano, J.; Niss, U.; Angulo, J.; Angulo, M.; Moreno-Vargas, A. J.; Carmona, A. T.; Ohlson, S.; Robina, I. *Chem. Eur. J.* 2013, 19, 17989-18003.

Ruvolo, P. P. *Biochim. Biophys Acta*. Molecular cell research (2015) E-pub ahead of print, title: Galectin-3 as a guardian of the tumor microenvironment, published on-line 8 Apr. 2015: [http://www.sciencedirect.com/science/article/pii/S0167488915002700], Salameh, B. A., Leffler, H. and Nilsson, U. J. (2005) *Bioorg. Med. Chem. Lett.* 15: 3344-3346.

Salameh, B. A., Cumpstey, I., Sundin, A., Leffler, H., and Nilsson, U. J. (2010). 1H-1,2,3-Triazol-1-yl thiodigalactoside derivatives as high affinity galectin-3 inhibitors. *Bioorg Med Chem* 18: 5367-5378.

Salomonsson, E., Larumbe, A., Tejler, J., Tullberg, E., Rydberg, H., Sundin, A., Khabut, A., Frejd, T., Lobsanov, Y. D., Rini, J. M., Nilsson, U. J., and Leffler, H (2010). Monovalent interactions of galectin-1. *Biochemistry* 49: 9518-9532.

Sörme, P., Qian, Y., Nyholm, P.-G., Leffler, H., Nilsson, U. J. (2002) Low micromolar inhibitors of galectin-3 based on 3'-derivatization of N-acetyllactosamine. *ChemBioChem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., Magnusson, B.-G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Thijssen V L, Heusschen R, Caers J, Griffloen A W. (2015) Galectin expression in cancer diagnosis and prognosis: A systematic review. Biochim Biophys Acta. 2015 April; 1855(2):235-47.

Toscano, M. A., Bianco, G. A., Ilarregui, J. M., Croci, D. O., Correale, J., Hernandez, J. D., Zwirner, N. W., Poirier, F., Riley, E. M., Baum, L. G., et al. (2007). Differential glycosylation of TH1, TH2 and TH-17 effector cells selectively regulates susceptibility to cell death. *Nat Immunol* 8: 825-834.

Viguier M, Advedissian T, Delacour D, Poirier F, Deshayes F. (2014) Galectins in epithelial functions. Tissue Barriers. 2014 May 6; 2:e29103.

We claim:
1. A D-galactopyranose compound of formula (1)

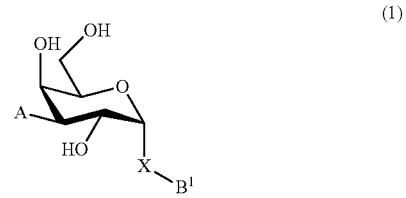

wherein
the pyranose ring is α-D-galactopyranose,
A is selected from

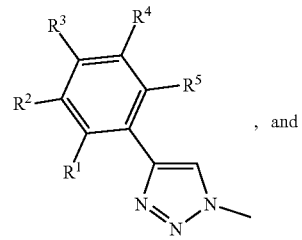
, and

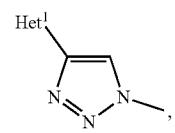
, wherein Het$^1$ is selected from a pyridinyl, optionally substituted with a group selected from H, CN, Br, Cl, I, F, methyl optionally substituted with a F, OCH$_3$ optionally substituted with a F, and SCH$_3$ optionally substituted with a F; or a pyrimidyl, optionally substituted with a group selected from H, CN, Br, Cl, I, F, methyl optionally substituted with a F, OCH$_3$ optionally substituted with a F, and SCH$_3$ optionally substituted with a F;

wherein R$^1$-R$^5$ are independently selected from a group consisting of H, CN, Br, Cl, I, F, methyl optionally substituted with a F, OCH$_3$ optionally substituted with a F, and SCH$_3$ optionally substituted with a F;

X is selected from S, SO, and SO$_2$;

B$^1$ is selected from a) a C$_{1-6}$ alkyl or branched C$_{3-6}$ alkyl substituted with a five or six membered heteroaromatic ring, optionally substituted with a substituent selected from CN, a halogen, methyl optionally substituted with a F, OCH$_3$ optionally substituted with a F, OCH$_2$CH$_3$ optionally substituted with a F, OH, and R$^{14}$—CONH— wherein R$^{14}$ is selected from C$_{1-3}$ alkyl and cyclopropyl; or a C$_{1-6}$ alkyl substituted with a phenyl, optionally substituted with a substituent selected from CN, a halogen, methyl optionally substituted with a F, OCH$_3$ optionally substituted with a F, OCH$_2$CH$_3$ optionally substituted with a F, OH, and R$^{15}$—CONH— wherein R$^{15}$ is selected from C$_{1-3}$ alkyl and cyclopropyl; b) an aryl, optionally substituted with a group selected from a halogen; CN; —COOH; —CONR$^{22}$R$^{23}$, wherein R$^{22}$ and R$^{23}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{28}R^{29}$, wherein $R^{28}$ and $R^{29}$ are independently selected from H, $C_{1-3}$ alkyl and isopropyl; OH; and $R^{16}$—CONH— wherein $R^{16}$ is selected from $C_{1-3}$ alkyl and cyclopropyl; c) a $C_{5-7}$ cycloalkyl, optionally substituted with a substituent selected from a halogen, CN, methyl optionally substituted with a F, $OCH_3$ optionally substituted with a F, $OCH_2CH_3$ optionally substituted with a F, OH, and $R^{17}$—CONH— wherein $R^{17}$ is selected from $C_{1-3}$ alkyl and cyclopropyl; and d) a heterocycle, optionally substituted with a group selected from a halogen; CN; —COOH; —$CONR^{24}R^{25}$, wherein $R^{24}$ and $R^{25}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{30}R^{31}$, wherein $R^{30}$ and $R^{31}$ are independently selected from H, $C_{1-3}$ alkyl and isopropyl; OH; and $R^{18}$—CONH— wherein $R^{18}$ is selected from $C_{1-3}$ alkyl and cyclopropyl; e) a $C_{1-6}$ alkyl or branched $C_{3-6}$ alkyl; or a pharmaceutically acceptable salt or solvate thereof.

2. The compound of claim 1, wherein A is selected from formula 2 wherein $R^1$-$R^5$ are independently selected from H, halogen, CN, methyl optionally substituted with a F, and $OCH_3$ optionally substituted with a F.

3. The compound of claim 1, wherein A is selected from formula 2 wherein $R^1$ and $R^5$ are selected from H and $R^2$-$R^4$ are selected from F, Cl, Br, CN, $CH_3$ and $CF_3$.

4. The compound of claim 1, wherein A is selected from formula 2 wherein $R^1$ and $R^5$ are selected from H and $R^2$ and $R^4$ are selected from F and $R^3$ is selected from Br, Cl, CN, $CH_3$ and $CF_3$.

5. The compound of claim 1, wherein A is selected from formula 2 wherein $R^1$ and $R^5$ are selected from H and $R^2$ is selected from F, and $R^3$-$R^4$ are selected from Cl.

6. The compound of claim 1, wherein A is selected from formula 2 wherein $R^1$, $R^2$ and $R^5$ are selected from H and $R^3$ and $R^4$ are selected from F and Cl.

7. The compound of claim 1, wherein A is selected from formula 3 wherein $Het^1$ is a pyridinyl optionally substituted with a group selected from Br, F, and Cl.

8. The compound of claim 1, wherein A is selected from formula 3 wherein $Het^1$ is a pyridinyl substituted with a group selected from F and Cl.

9. The compound of claim 1, wherein X is selected from S.

10. The compound of claim 1, wherein $B^1$ is selected from an aryl, optionally substituted with a group selected from a halogen; CN; methyl optionally substituted with a F; $OCH_3$ optionally substituted with a F; $OCH_2CH_3$ optionally substituted with a F; OH; $R^{16}$—CONH— wherein $R^{16}$ is selected from $C_{1-3}$ alkyl and cyclopropyl; —COOH; $NR^{28}R^{29}$, wherein $R^{28}$ and $R^{29}$ are independently selected from H, $C_{1-3}$ alkyl and isopropyl; and —$CONH_2$.

11. The compound of claim 1, wherein $B^1$ is selected from a phenyl or phenyl substituted with one, two or three substituents selected from halogen.

12. The compound of claim 1, wherein $B^1$ is selected from a phenyl substituted with two substituents selected from halogen.

13. The compound of claim 1, wherein $B^1$ is selected from a heterocycle, optionally substituted with a group selected from a halogen; CN; methyl optionally substituted with a F; $OCH_3$ optionally substituted with a F; $OCH_2CH_3$ optionally substituted with a F; OH; $CONH_2$; $NR^{30}R^{31}$, wherein $R^{30}$ and $R^{31}$ are independently selected from H, $C_{1-3}$ alkyl and isopropyl; and $R^{18}$—CONH— wherein $R^{18}$ is selected from $C_{1-3}$ alkyl and cyclopropyl.

14. The compound of claim 1, wherein $B^1$ is selected from a pyridinyl substituted with a group selected from halogen and CN.

15. The compound of claim 1 selected from:
4-Bromo-5-cyano-2-pyridyl 3-deoxy-3-[4-(3,4,5-trifluorophenyl)-1H-1,2,3-triazol-1-yl]-1-thio-α-D-galactopyranoside;
4-Chloro-5-cyano-2-pyridyl 3-deoxy-3-[4-(3,4,5-trifluorophenyl)-1H-1,2,3-triazol-1-yl]-1-thio-α-D-galactopyranoside;
2-Chloro-4-pyridyl 3-deoxy-3-[4-(3,4,5-trifluorophenyl)-1H-1,2,3-triazol-1-yl]-1-thio-α-D-galactopyranoside;
5-Chloro-2-cyano-3-pyridyl 3-deoxy-3-[4-(3,4,5-trifluorophenyl)-1H-1,2,3-triazol-1-yl]-1-thio-α-D-galactopyranoside;
5-Bromo-6-cyano-3-pyridyl 3-deoxy-3-[4-(3,4,5-trifluorophenyl)-1H-1,2,3-triazol-1-yl]-1-thio-α-D-galactopyranoside;
5-Bromo-2-cyano-3-pyridyl 3-deoxy-3-[4-(3,4,5-trifluorophenyl)-1H-1,2,3-triazol-1-yl]-1-thio-α-D-galactopyranoside;
4-Chloro-2-pyridyl 3-deoxy-3-[4-(3,4,5-trifluorophenyl)-1H-1,2,3-triazol-1-yl]-1-thio-α-D-galactopyranoside;
5-Bromo-3-pyridyl 3-deoxy-3-[4-(4-chloro-3,5-difluorophenyl)-1H-1,2,3-triazol-1-yl]-1-thio-α-D-galactopyranoside;
5-Chloro-3-pyridyl 3-deoxy-3-[4-(4-chloro-3,5-difluorophenyl)-1H-1,2,3-triazol-1-yl]-1-thio-α-D-galactopyranoside;
5-Chloro-6-cyano-3-pyridyl 3-deoxy-3-[4-(4-chloro-3,5-difluorophenyl)-1H-1,2,3-triazol-1-yl]-1-thio-α-D-galactopyranoside;
5-Bromo-2-cyano-3-pyridyl 3-deoxy-3-[4-(4-chloro-3,5-difluorophenyl)-1H-1,2,3-triazol-1-yl]-1-thio-α-D-galactopyranoside;
5-Bromo-6-cyano-3-pyridyl 3-deoxy-3-[4-(4-chloro-3,5-difluorophenyl)-1H-1,2,3-triazol-1-yl]-1-thio-α-D-galactopyranoside;
5-Chloro-2-cyano-3-pyridyl 3-deoxy-3-[4-(4-chloro-3,5-difluorophenyl)-1H-1,2,3-triazol-1-yl]-1-thio-α-D-galactopyranoside;
5-Chloro-3-pyridyl 3-deoxy-3-[4-(4-cyano-3,5-difluorophenyl)-1H-1,2,3-triazol-1-yl]-1-thio-α-D-galactopyranoside;
5-Chloro-3-pyridyl 3-deoxy-3-[4-(3,5-difluoro-4-trifluoromethyl-phenyl)-1H-1,2,3-triazol-1-yl]-1-thio-α-D-galactopyranoside;
5-Chloro-3-pyridyl 3-deoxy-3-[4-(3,5-difluoro-4-methylphenyl)-1H-1,2,3-triazol-1-yl]-1-thio-α-D-galactopyranoside;
5-Chloro-3-pyridyl 3-deoxy-3-[4-(4-bromo-3,5-difluorophenyl)-1H-1,2,3-triazol-1-yl]-1-thio-α-D-galactopyranoside;
5-Chloro-3-pyridyl 3-deoxy-3-[4-(3,4-dichloro-5-fluorophenyl)-1H-1,2,3-triazol-1-yl]-1-thio-α-D-galactopyranoside;

5-Chloro-3-pyridyl 3-deoxy-3-[4-(4-chloro-3-fluorophenyl)-1H-1,2,3-triazol-1-yl]-1-thio-α-D-galactopyranoside;

3,4-Dichlorophenyl 3-deoxy-3-[4-(5-fluoro-3-pyridyl)-1H-1,2,3-triazol-1-yl]-1-thio-α-D-galactopyranoside;

5-Chloro-3-pyridyl 3-deoxy-3-[4-(3,4-dichlorophenyl)-1H-1,2,3-triazol-1-yl]-1-thio-α-D-galactopyranoside; and 3,4-Dichlorophenyl 3-deoxy-3-[4-(5-chloro-3-pyridyl)-1H-1,2,3-triazol-1-yl]-1-thio-α-D-galactopyranoside.

16. A pharmaceutical composition comprising the compound of claim 1 and a pharmaceutically acceptable additive.

17. A method for treating a disorder relating to the binding of a galectin-3 to a ligand in a mammal, comprising the administration of the therapeutically effective amount pharmaceutical composition according to claim 16 to a mammal in need of said treatment.

18. The compound for use according to claim 17, wherein said disorder is selected from the group consisting of inflammation; fibrosis; scarring; keloid formation; aberrant scar formation; surgical adhesions; septic shock; cancer; metastasising cancers; autoimmune diseases; metabolic disorders; heart disease; heart failure; pathological angiogenesis; and eye diseases; atherosclerosis; metabolic diseases; asthma and other interstitial lung diseases, including Hermansky-Pudlak syndrome, mesothelioma; liver disorders.

19. A method for treatment of a disorder relating to the binding of a galectin-3 to a ligand in a mammal, wherein a therapeutically effective amount of at least one compound according to claim 1 is administered to a mammal in need of said treatment.

20. The method of claim 19, wherein said disorder is selected from the group consisting of inflammation; fibrosis; scarring; keloid formation; aberrant scar formation; surgical adhesions; septic shock; cancer; metastasising cancers; autoimmune diseases; metabolic disorders; heart disease; heart failure; pathological angiogenesis; and eye diseases; atherosclerosis; metabolic diseases; asthma and other interstitial lung diseases, including Hermansky-Pudlak syndrome, mesothelioma; liver disorders.

\* \* \* \* \*